United States Patent
Tsuji et al.

(10) Patent No.: US 11,674,180 B2
(45) Date of Patent: Jun. 13, 2023

(54) METHOD AND KIT FOR DETERMINING HYPEREXCITABILITY IN SUBJECT

(71) Applicant: The University of Tokyo, Tokyo (JP)

(72) Inventors: Shoji Tsuji, Tokyo (JP); Hiroyuki Ishiura, Tokyo (JP)

(73) Assignee: The University of Tokyo, Tokyo (JP)

( * ) Notice: Subject to any disclaimer, the term of this patent is extended or adjusted under 35 U.S.C. 154(b) by 0 days.

(21) Appl. No.: 16/968,369

(22) PCT Filed: Feb. 12, 2019

(86) PCT No.: PCT/JP2019/004916
§ 371 (c)(1),
(2) Date: Aug. 7, 2020

(87) PCT Pub. No.: WO2019/156257
PCT Pub. Date: Aug. 15, 2019

(65) Prior Publication Data
US 2021/0047690 A1 Feb. 18, 2021

Related U.S. Application Data

(60) Provisional application No. 62/628,324, filed on Feb. 9, 2018.

(51) Int. Cl.
C12Q 1/6883 (2018.01)
(52) U.S. Cl.
CPC ..... *C12Q 1/6883* (2013.01); *C12Q 2600/156* (2013.01)
(58) Field of Classification Search
None
See application file for complete search history.

(56) References Cited

U.S. PATENT DOCUMENTS 6,582,908 B2 * 6/2003 Fodor ................. B01J 19/0046
435/288.3

OTHER PUBLICATIONS

Valenti et al. Atherosclerosis. 1999. 147: 17-24 (Year: 1999).*
Ishiura et al Nature Genetics. Published online Mar. 5, 2018. 50: 581-590 and Supplementary Information, 50 pages total. (Year: 2018).*
Ishiura et al J Neurological Sciences. 2017. 381, abstract 95, WCN17-1414, p. 346) (Year: 2017).*
Cen et al Brain. Jun. 23, 2018. 141:2280-2288 and Supplementary Tables 1-4 (Year: 2018).*
Mori et al J Human Genetics. 2011. 56: 742-747 (Year: 2011).*
Striano, P. Feb. 2012. "Benign adult familial myoclonic epilepsy", at Orpanet, available via URL: < orpha.net/consor/cgi-bin/OC_Exp.php?Lng=GB&Expert=86814#:~:text=Management%20and%20treatment&text=Valproate%2C%20levetiracetam%2C%20and%20benzodiazepines%20are,may%20be%20difficult%20to%20treat> (Year: 2012).*

Amato et al., "Childhood-onset oculopharyngodistal myopathy with chronic intestinal pseudo-obstruction," Muscle Nerve, 18:842-847 (1995).
Ameur et al., "Total RNA sequencing reveals nascent transcription and widespread co-transcriptional splicing in the human brain," Nat Struct Mol Biol, 18(12):1435-1440 (2011).
Arcot et al., "Alu repeats: a source for the genesis of primate microsatellites," Genomics, 29:136-144 (1995).
Bahlo et al., "Recent advances in the detection of repeat expansions with short-read next-generation sequencing," F1000Res, 7(F1000 Faculty Rev):736, 11 pages (2018).
Beck et al., "Large C9orf72 hexanucleotide repeat expansions are seen in multiple neurodegenerative syndromes and are more frequent than expected in the UK population," Am J Hum Genet, 92:345-353 (2013).
Benson, "Tandem repeat finder: a program to analyze DNA sequences," Nucleic Acids Res, 27(2):573-580 (1999).
Brais et al., "Short GCG expansions in the PABP2 gene cause oculopharyngeal muscular dystrophy," Nat Genet, 18:164-167 (1998).
Buxton et al., "Detection of an unstable fragment of DNA specific to individuals with myotonic dystrophy," Nature, 355:547-548 (1992).
Cen et al., "Fine mapping and whole-exome sequencing of a familial cortical myoclonic tremor with epilepsy family," Am J Med Genet Part B, 168B:595-599 (2015).
Charlet-B. et al., "Loss of the muscle-specific chloride channel in type 1 myotonic dystrophy due to misregulated alternative splicing," Mol Cell, 10, 45-53 (2002).
Coffey et al., "Expanded clinical phenotype of women with the FMR1 premutation," Am J Med Genet A, 146A(8):1009-1016 (2008).
Dejesus-Hernandez et al., "Expanded GGGGCC hexanucleotide repeat in noncoding region of C9ORF72 causes chromosome 9p-linked FTD and ALS," Neuron, 72(2):245-256 (2011).
Depienne et al., "Familial cortical myoclonic tremor with epilepsy: the third locus (FCMTE3) maps to 5p," Neurology, 74:2000-2003 (2010).
Data Supplement of Depienne et al., "Familial cortical myoclonic tremor with epilepsy: the third locus (FCMTE3) maps to 5p," Neurology, 74:2000-2003 (2010); 2 pages.
Dobin et al., "STAR: ultrafast universal RNA-seq aligner," Bioinformatics, 29(1):15-21 (2013).
Doi et al., "Rapid detection of expanded short tandem repeats in personal genomics using hybrid sequencing," Bioinformatics, 30(6):815-822 (2014).
Durmus et al., "Oculopharyngodistal myopathy is a distinct entity: clinical and genetic features of 47 patients," Neurology, 76:227-235 (2011).

(Continued)

*Primary Examiner* — Carla J Myers
(74) *Attorney, Agent, or Firm* — Finnegan, Henderson, Farabow, Garrett & Dunner, LLP

(57) ABSTRACT

A method for determining a hyperexcitability in a subject comprising detecting a repeat expansion of TTTCA, TTTTA, or a complementary sequence thereof in a nucleic acid sample from the subject.

6 Claims, 47 Drawing Sheets
Specification includes a Sequence Listing.

(56) References Cited

OTHER PUBLICATIONS

Fiddes et al., "Human-specific NOTCH2NL genes affect Notch signaling and cortical neurogenesis," Cell, 173:1356-1369 (2018).
Fratta et al., "Screening a UK amyotrophic lateral sclerosis cohort provides evidence of multiple origins of the C9orf72 expansion," Neurobiol Aging, 36:546.e1-546.e7 (2015).
Frey et al., "PCR-amplification of GC-rich regions: 'slowdown PCR'," Nat Protoc, 3(8):1312-1317 (2008).
Fukuda et al., "SNP HiTLink: a high-throughput linkage analysis system employing dense SNP data," BMC Bioinformatics, 10:121, 9 pages (2009).
Gudbjartsson et al., "Allegro version 2," Nat Genet, 37(10):1015-1016 (2005).
Guerrini et al., "Autosomal dominant cortical myoclonus and epilepsy (ADCME) with complex partial and generalized seizures: a newly recognized epilepsy syndrome with linkage to chromosome 2p11.1-q12.2," Brain, 124:2459-2475 (2001).
Haeusler et al., "C9orf72 nucleotide repeat structures initiate molecular cascades of disease," Nature, 507:195-200 (2014).
Hagerman et al., "Intention tremor, parkinsonism, and generalized brain atrophy in male carriers of fragile X," Neurology, 57:127-130 (2001).
Haltia et al., "Neuronal intranuclear inclusion disease in identical twins," Ann Neurol, 15:316-321 (1984).
Henden et al., "Identity by descent fine mapping of familial adult myoclonus epilepsy (FAME) to 2p11.2-2q11.2," Hum Genet, 135:1117-1125 (2016).
Hitomi et al., "Clinical anticipation in Japanese families of benign adult familial myoclonus epilepsy," Epilepsia 53(2):e33-36 (2012).
Hitomi et al., "Increased clinical anticipation with maternal transmission in benign adult familial myoclonus epilepsy in Japan," Epileptic Disord, 15(4):428-432 (2013).
Hitomi et al., "Increased cortical hyperexcitability and exaggerated myoclonus with aging in benign adult familial myoclonus epilepsy," Mov Disord, 26(8):1509-1514 (2011).
Hunsaker et al., "Widespread non-central nervous system organ pathology in fragile X premutation carriers with fragile X-associated tremor/ataxia syndrome and CGG knock-in mice," Acta Neuropathol, 122(4):467-479 (2011).
Ikeda et al., "Cortical tremor: a variant of cortical reflex myoclonus," Neurology, 40:1561-1565 (1990).
Inazuki et al., "Familial Disease with Myoclonus and Epilepsy—The Nosological Place of Familial Essential Myoclonus and Epilepsy (FEME)," Psych Neurol Jpn, 92(1):1-21 (1990); an English translation of the title, abstract, and keywords included.
Ishiura et al., "Expansions of intronic TTTCA and TTTTA repeats in benign adult familial myoclonic epilepsy," Nat Genet 50:581-590 (2018).
Jacquemont et al., "Penetrance of the fragile X-associated tremor/ataxia syndrome in a premutation carrier population," JAMA, 291(4):460-469 (2004).
Jin et al., "Pur alpha binds to rCGG repeats and modulates repeat-mediated neurodegeneration in a *Drosophila* model of fragile X tremor/ataxia syndrome," Neuron, 55(4):556-564 (2007).
Kent, "BLAT—the blast-like alignment tool," Genome Res, 12(4):656-664 (2002).
Kim et al., "TopHat2: accurate alignment of transcriptomes in the presence of insertions, deletions, and gene fusions," Genome Biol, 14:R36 (2013), 13 pages.
Kimber et al., "Familial neuronal intranuclear inclusion disease with ubiquitin positive inclusions," J Neurol Sci, 160:33-40 (1998).
Koren et al., "Canu: scalable and accurate long-read assembly via adaptive k-mer weighting and repeat separation," Genome Res, 27:722-736 (2017).
Kurosaki et al., "Alu-mediated acquisition of unstable ATTCT pentanucleotide repeats in the human ATXN10 gene," Mol Biol Evol, 26(11):2573-2579 (2009).
Larkin et al., "Clustal Wand Clustal X version 2.0," Bioinformatics, 23(21):2947-2948 (2007).
Li et al., "Fast and accurate short read alignment with Burrows-Wheeler transform," Bioinformatics, 25(14):1754-1760 (2009).
Li et al., "The sequence alignment/map format and SAMtools," Bioinformatics, 25(16):2078-2079 (2009).
Li, "Minimap and miniasm: fast mapping and de novo assembly for noisy long sequences," Bioinformatics, 32(14):2103-2110 (2016).
Li, "Minimap2: pairwise alignment for nucleotide sequences," Bioinformatics, 34(18):3094-3100 (2018).
Lindenberg et al., "A light and electron microscopy study of an unusual widespread nuclear inclusion body disease—A possible residuum of an old herpesvirus infection," Acta Neuropathol, 10:54-73 (1968).
Loureiro et al., "Unstable repeat expansions in neurodegenerative diseases: nucleocytoplasmic transport emerges on the scene," Neurobiol Aging, 39:174-183 (2016).
Mankodi et al., "Expanded CUG repeats trigger aberrant splicing of ClC-1 chloride channel pre-mRNA and hyperexcitability of skeletal muscle in myotonic dystrophy," Mol Cell, 10:35-44 (2002).
Matsuura et al., "Large expansion of the ATTCT pentanucleotide repeat in spinocerebellar ataxia type 10," Nat Genet, 26:191-194 (2000).
Mikami et al., "Localization of a gene for benign adult familial myoclonic epilepsy to chromosome 8q23.3-8q24.1," Am J Hum Genet, 65:745-751 (1999).
Mitsuhashi et al., "Tandem-genotypes: robust detection of tandem repeat expansions from long DNA reads," Genome Biol, 20:58, 17 pages (2019).
Miyake et al., "Biallelic TBCD mutations cause early-onset neurodegenerative encephalopathy," Am J Hum Genet, 99:950-961 (2016).
Mori et al., "Remapping and mutation analysis of benign adult familial myoclonic epilepsy in a Japanese pedigree," J Hum Genet, 56:742-747 (2011).
Nakano et al., "PML nuclear bodies are altered in adult-onset neuronal intranuclear hyaline inclusion disease," J Neuropathol Exp Neurol, 76(7):585-594 (2017).
Plaster et al., "Genetic localization of the familial adult myoclonic epilepsy (FAME) gene to chromosome 8q24," Neurology, 53:1180-1183 (1999).
Regan et al., "A rapid molecular approach for chromosomal phasing," PLoS One 10(3):e0118270 (2015), 15 pages.
Renton et al., "A hexanucleotide repeat expansion in C9ORF72 is the cause of chromosome 9p21-linked ALS-FTD," Neuron, 72(2):257-268 (2011).
Robinson et al., "Integrative Genomic Viewer," Nat Biotechnol, 29(1):24-26 (2011).
Sanpei et al., "Identification of the spinocerebellar ataxia type 2 gene using a direct identification of repeat expansion and cloning technique, DIRECT," Nat Genet, 14:277-284 (1996).
Sato et al., "Spinocerebellar ataxia type 31 is associated with 'inserted' penta-nucleotide repeats containing (TGGAA)n," Am J Hum Genet, 85:544-557 (2009).
Satoyoshi et al., "Oculopharyngodistal myopathy,"Arch Neurol, 34:89-92 (1977).
Satoyoshi, "Distal myopathy," Tohoku J Exp Med, 161 Suppl:1-19 (1990).
Schuffler et al., "A familial neuronal disease presenting as intestinal pseudoobstruction," Gastroenterology, 75:889-898 (1978).
Seltzer et al., "Prevalence of CGG expansions of the FMR1 gene in a US population-based sample," Am J Med Genet B Neuropsychiatr Genet, 159(5):589-597 (2012).
Sofola et al., "RNA-binding proteins hnRNP A2/B1 and CUGBP1 suppress fragile X CGG premutation repeat-induced neurodegeneration in a *Drosophila* model of FXTAS," Neuron, 55(4):565-571 (2007).
Sone et al., "Clinicopathological features of adult-onset neuronal intranuclear inclusion disease," Brain, 139:3170-3186 (2016).
Sone et al., "Neuronal intranuclear hyaline inclusion disease showing motor-sensory and autonomic neuropathy," Neurology, 65:1538-1543 (2005).
Sone et al., "Neuronal intranuclear inclusion disease cases with leukoencephalopathy diagnosed via skin biopsy," J Neurol Neurosurg Psychiatry, 85:354-356 (2014).

(56) References Cited

OTHER PUBLICATIONS

Sone et al., "Skin biopsy is useful for the antemortem diagnosis of neuronal intranuclear inclusion disease," Neurology, 76:1372-1376 (2011).
Sugiyama et al., "MR imaging features of the cerebellum in adult-onset neuronal intranuclear inclusion disease: 8 cases," Am J Neuroradiol, 38(11):2100-2104 (2017).
Suzuki, "Clinical genetics and linkage analysis of familial essential myoclonus and epilepsy (FEME)," Niigata Med J, 116:535-545 (2002); an English translation of the title, abstract, and keywords included.
Suzuki et al., "Human-specific NOTCH2NL genes expand cortical neurogenesis through Delta/Notch regulation," Cell, 173:1370-1384 (2018).
Sznajder et al., "Intron retension induced by microsatellite expansions as a disease biomarker," Proc Natl Acad Sci U. S. A., 115(16):4234-4239 (2018).
Takahashi-Fujigasaki et al., "Adult-onset neuronal intranuclear hyaline inclusion disease is not rare in older adults," Geriatr Gerontol Int, 16 (Suppl 1):51-56 (2016).
Takumida et al., "Case of a 78-year-old woman with a neuronal intranuclear inclusion disease," Geriatr Gerontol Int, 17(12):2623-2625 (2017).
Taneja et al., "Foci of trinucleotide repeat transcripts in nuclei of myotonic dystrophy cells and tissues," J Cell Biol, 128(6):995-1002 (1995).
Thevathasan et al., "Oculopharyngodistal myopathy—a possible association with cardiomyopathy," Neuromuscul Disord, 21:121-125 (2011).
Todd et al., "CGG repeat-associated translation mediates neurodegeneration in fragile X tremor ataxia syndrome," Neuron, 78(3):440-455 (2013).
Trapnell et al., "Transcript assembly and quantification by RNA-Seq reveals unannotated transcripts and isoform switching during cell differentiation," Nat Biotechnol, 28(5), 511-515 (2010).
Uhlén et al., "Tissue-based map of the human proteome," Science, 347(6220):1260419 (2015), 11 pgs.
Uyama et al., Familial adult myoclonic epilepsy (FAME). Adv neurol, 95:281-288 (2005).
Uyama et al., "Autosomal recessive oculopharyngodistal myopathy in light of distal myopathy with rimmed vacuoles and oculopharyngeal muscular dystrophy," Neuromuscul Disord, 8:119-125 (1998).
Van der Sluijs et al., "Autosomal recessive oculopharyngodistal myopathy: a distinct phenotypical, histological, and genetic entity," J Neurol Neurosurg Psychiatr, 75:1499-1501 (2004).
Vandepoele et al., "A novel gene family NBPF: intricate structure generated by gene duplication during primate evolution," Mol Biol Evol, 22(11):2265-2274 (2005).
Yamaguchi et al., "An autopsy case of familial neuronal intranuclear inclusion disease with dementia and neuropathy," Intern Med, 57(23):3459-3462 (2018).
Yasuda, "Benign adult familial myoclonic epilepsy (BAFME)," Kawasaki Med J, 17(1-4):1-13 (1991).
Yeetong et al., "A newly identified locus for benign adult familial myoclonic epilepsy on chromosome 3q26.32-3q28," Eur J Hum Genet, 21:225-228 (2013).
Yoshida et al., "Distinctive feature of degenerating Purkinje cells in spinocerebellar ataxia type 31," Neuropathology, 34:261-267 (2014).
Zhao et al., "Clinical and muscle imaging findings in 14 mainland Chinese patients with oculopharyngodistal myopathy," PLoS One, 10(6):e0128629 (2015), 12 pages.
Zheng et al., "Haplotyping germline and cancer genomes with high-throughput linked-read sequencing," Nat Biotechnol, 34(3):303-311 (2016).
Zu et al., "Non-ATG-initiated translation directed by microsatellite expansions," Proc Natl Acad Sci U S A, 108(1):260-265 (2011).

\* cited by examiner

[Fig. 1]
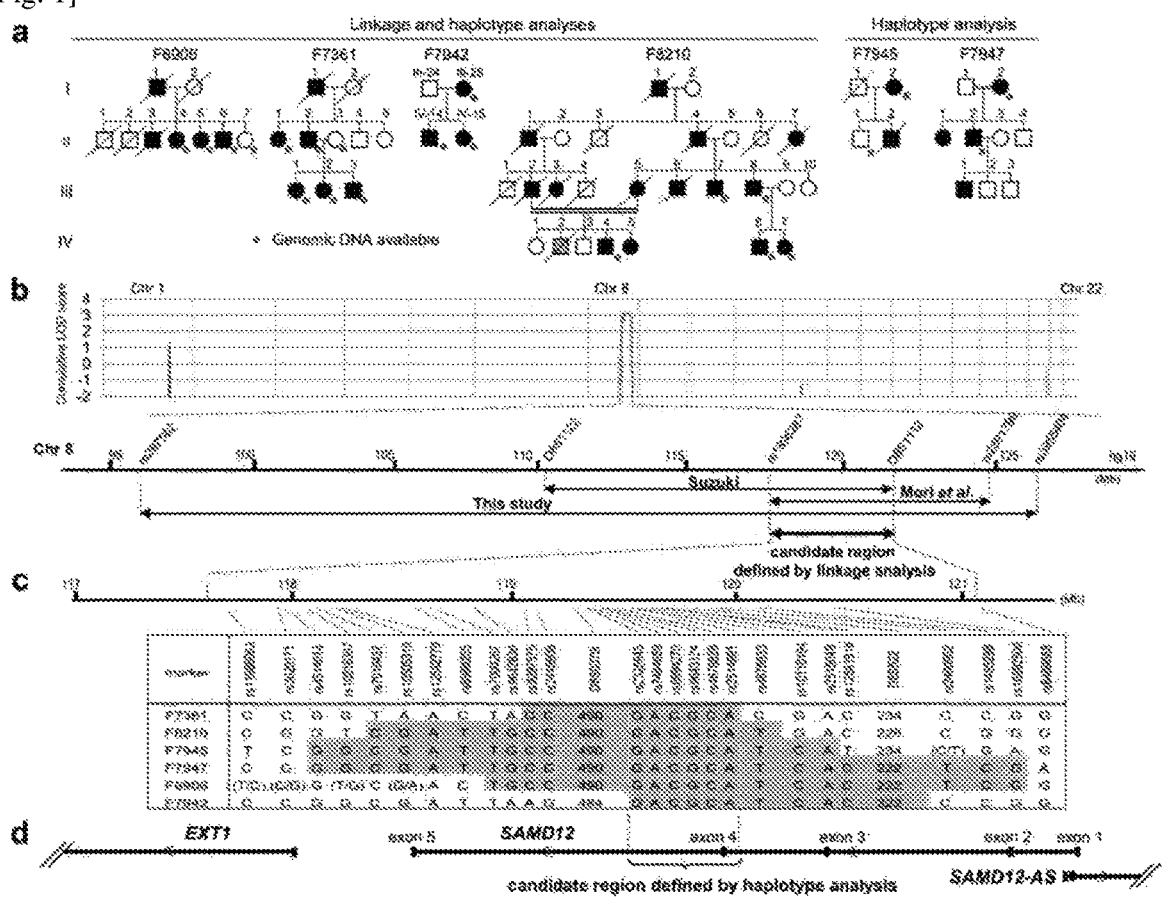

[Fig. 2D]
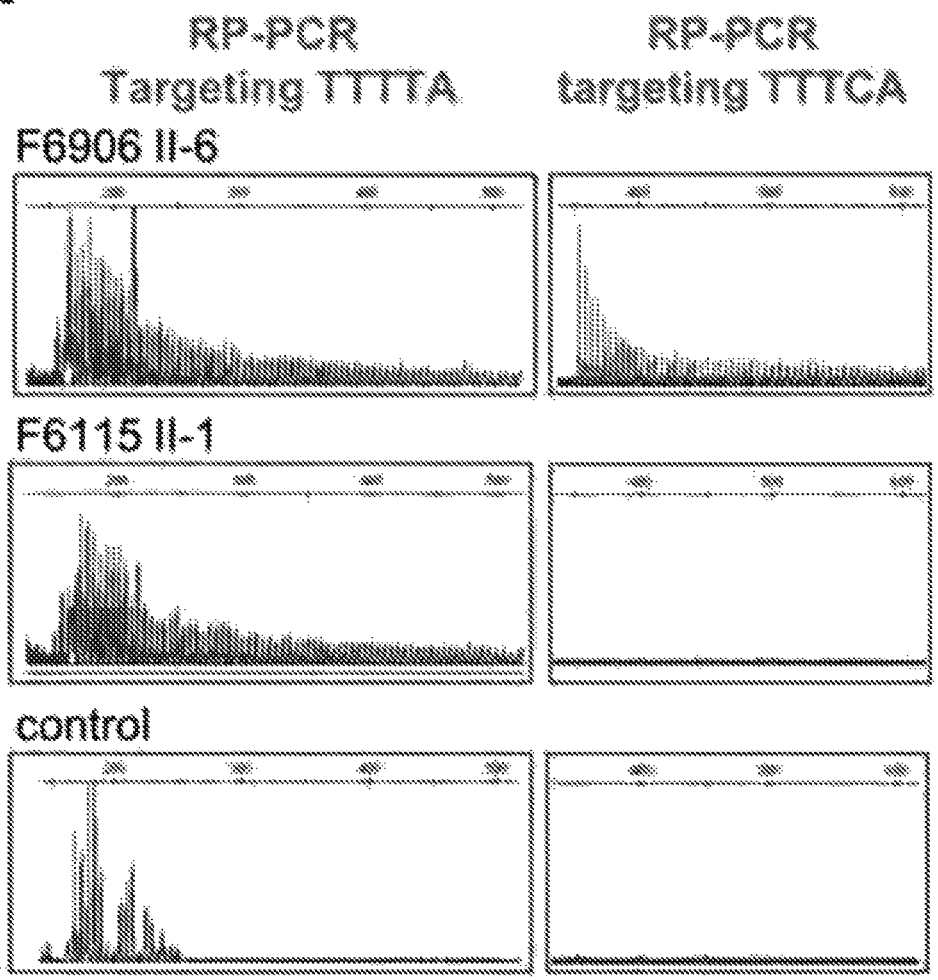

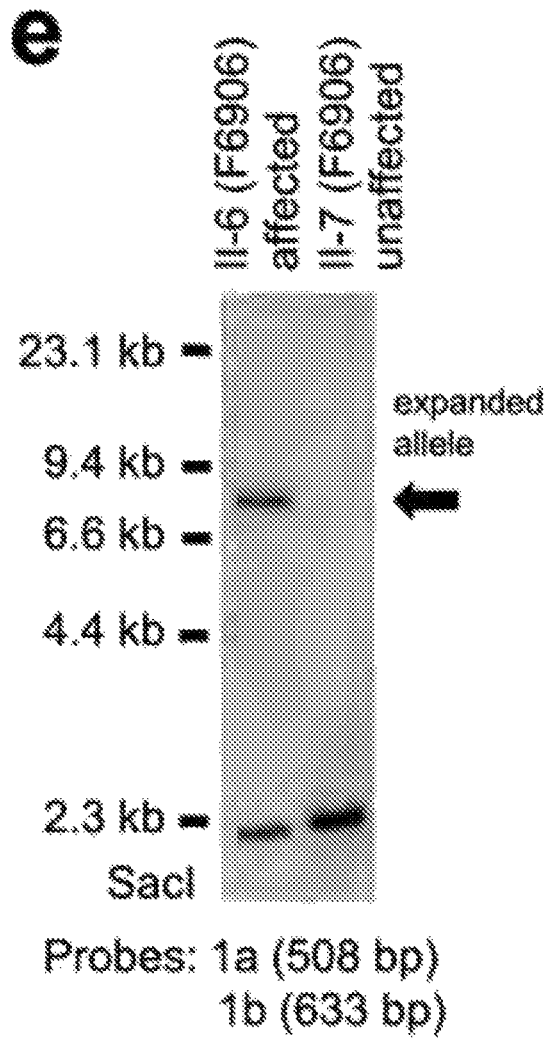

[Fig. 2F]
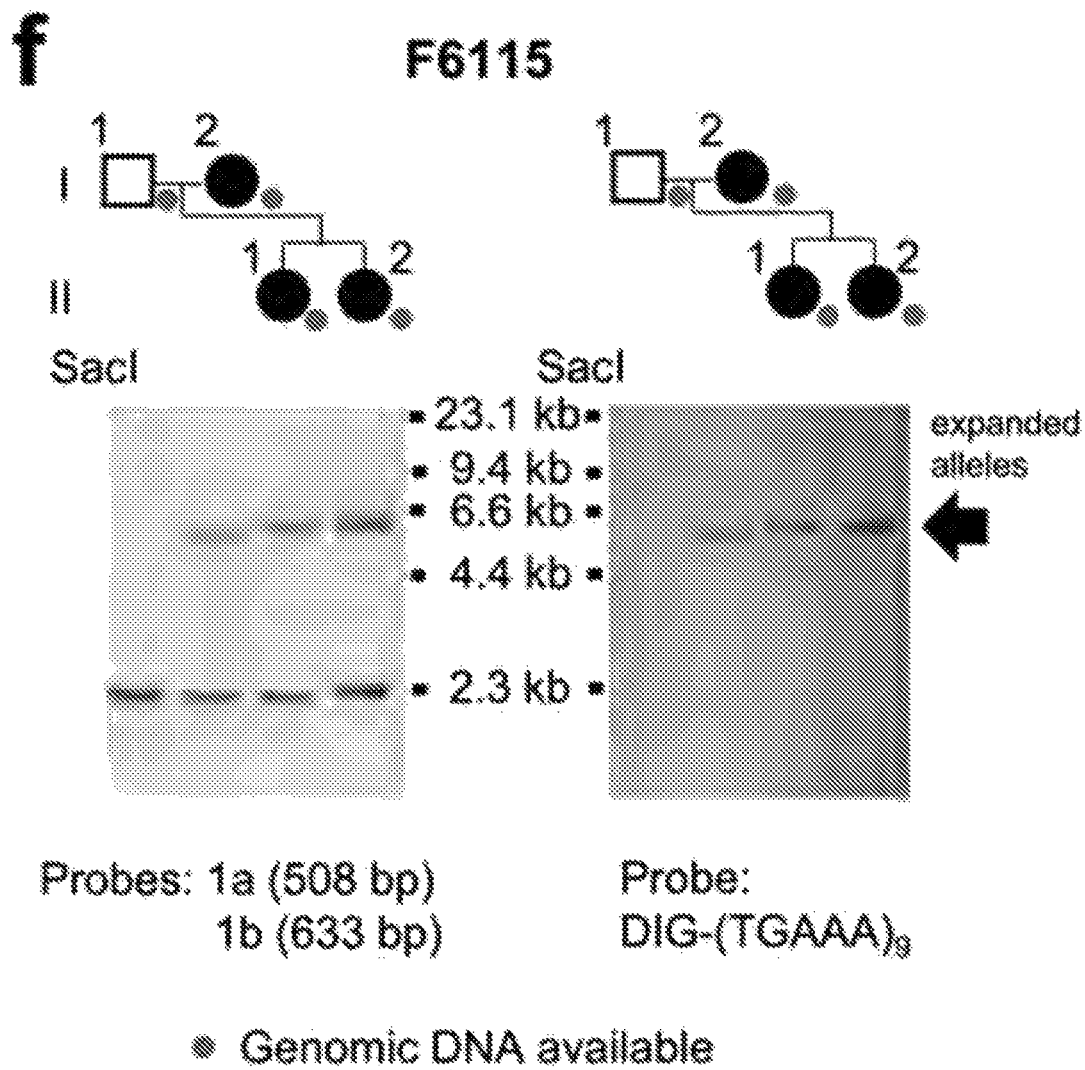

a

Reference genome 5'-GTTCAT-(TTTTA)$_7$(TTA)(TTTTA)$_{13}$-TTTGA

F6906 (II-6) 5'-GTTCAT-(TTTTA)$_2$TTTTTTTA(TTTTA)$_{104}$TTA(TTTTA)$_3$TTTA(TTTTA)$_{10}$(TTTCA)$_{66}$-TTGA

F6115 (I-2) 5'-GTTCAT-(TTTTA)$_3$TTTTTTTA(TTTTA)$_{80}$(TTTCA)$_{61}$(TTTTA)$_{73}$TTTATTTTA-TTTGA

*Fig. 3a*

[Fig. 4A]
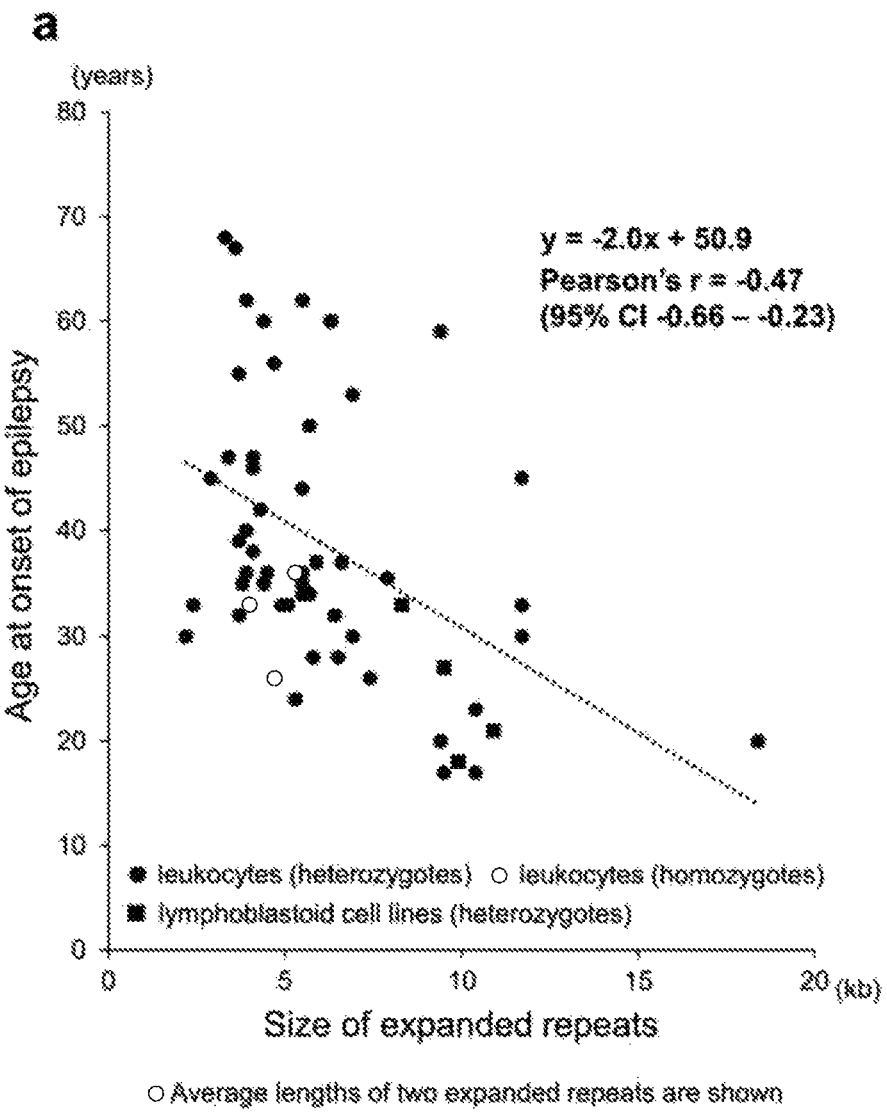

[Fig. 4B]
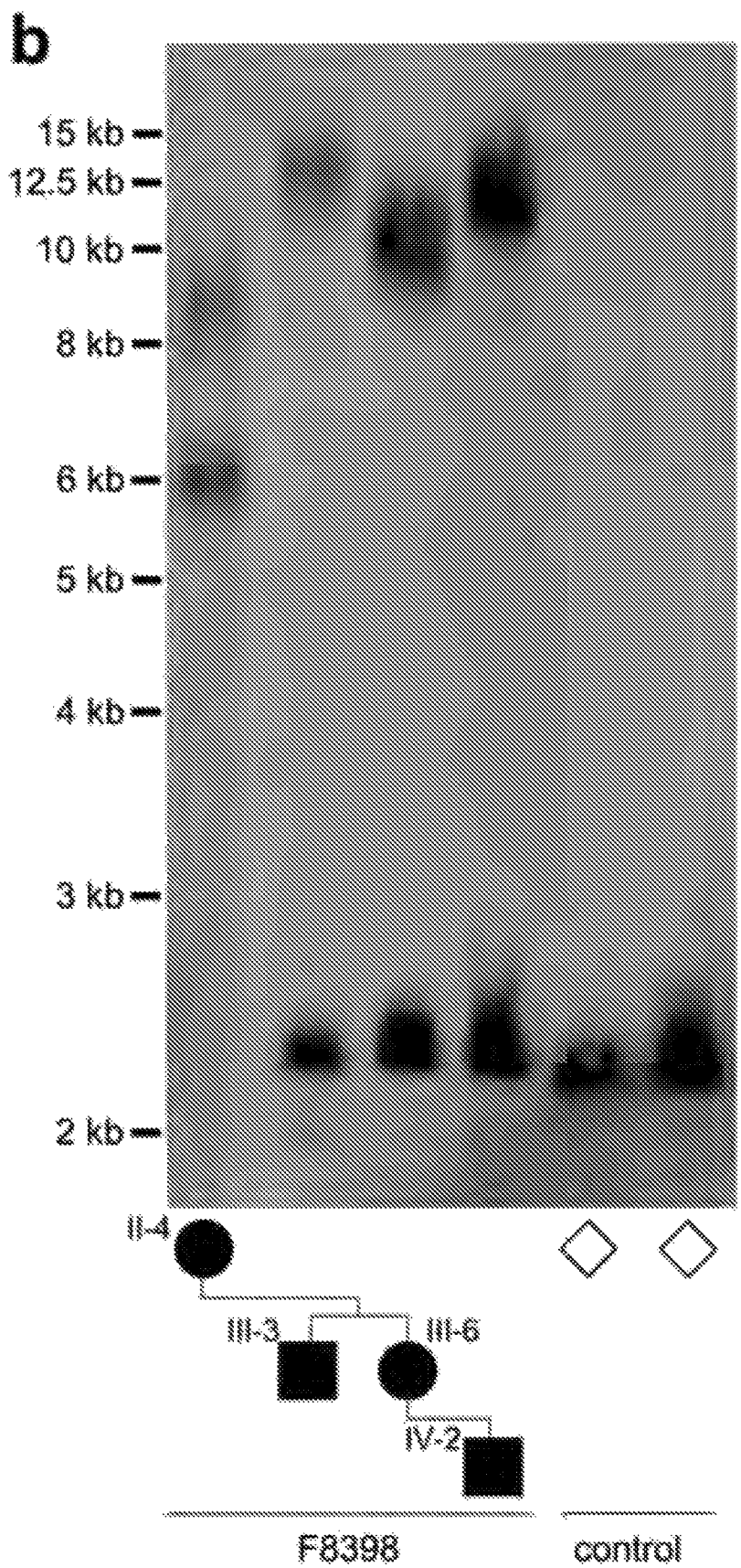

[Fig. 5]
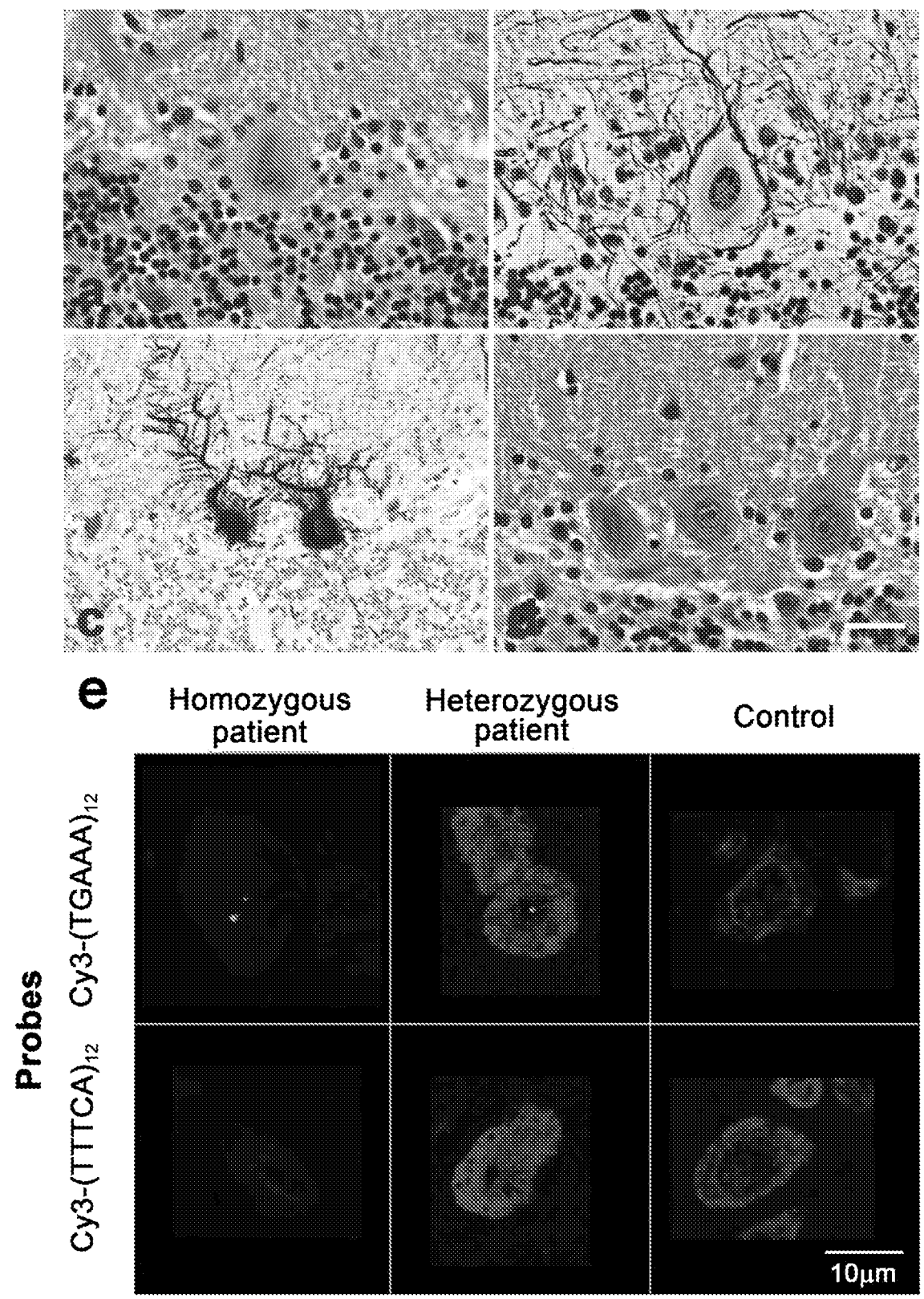

[Fig. 6B]
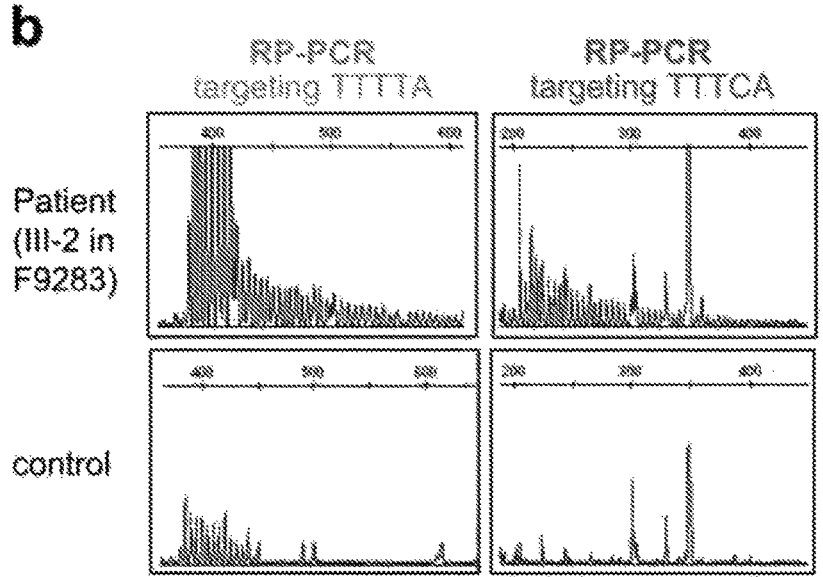
[Fig. 6C]
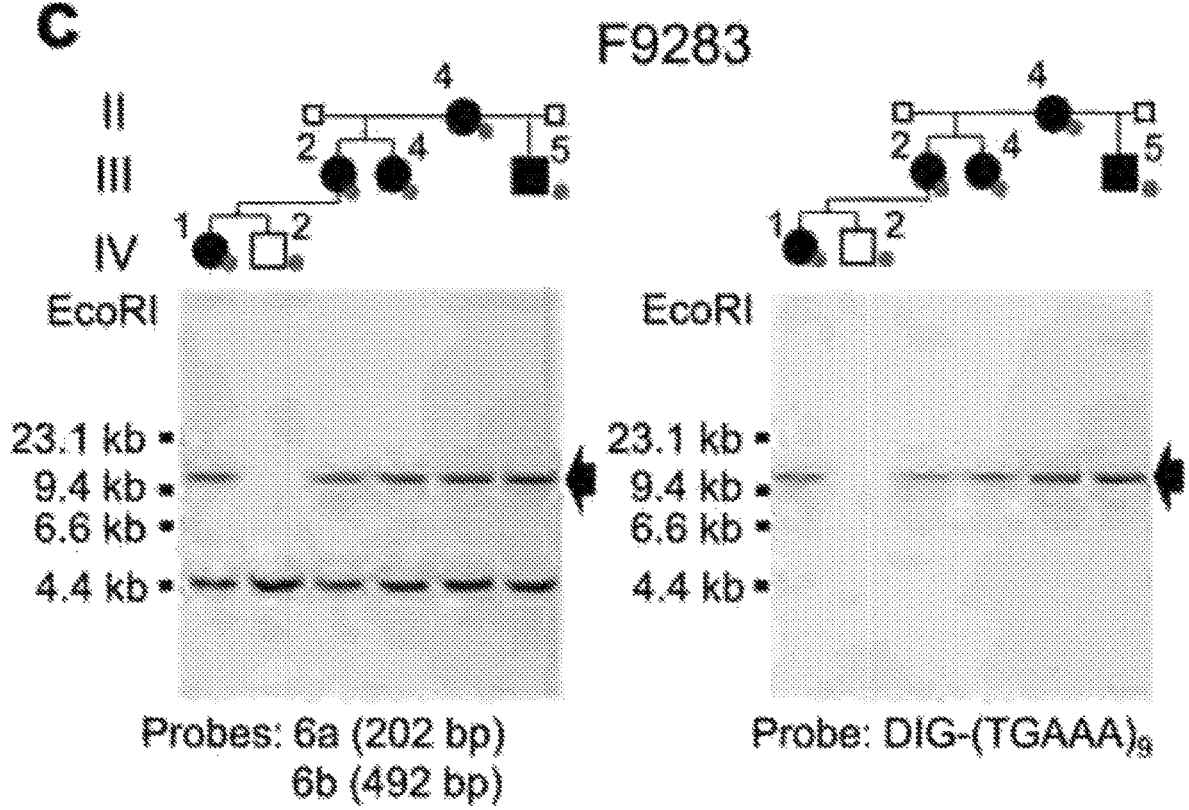

[Fig. 6E]
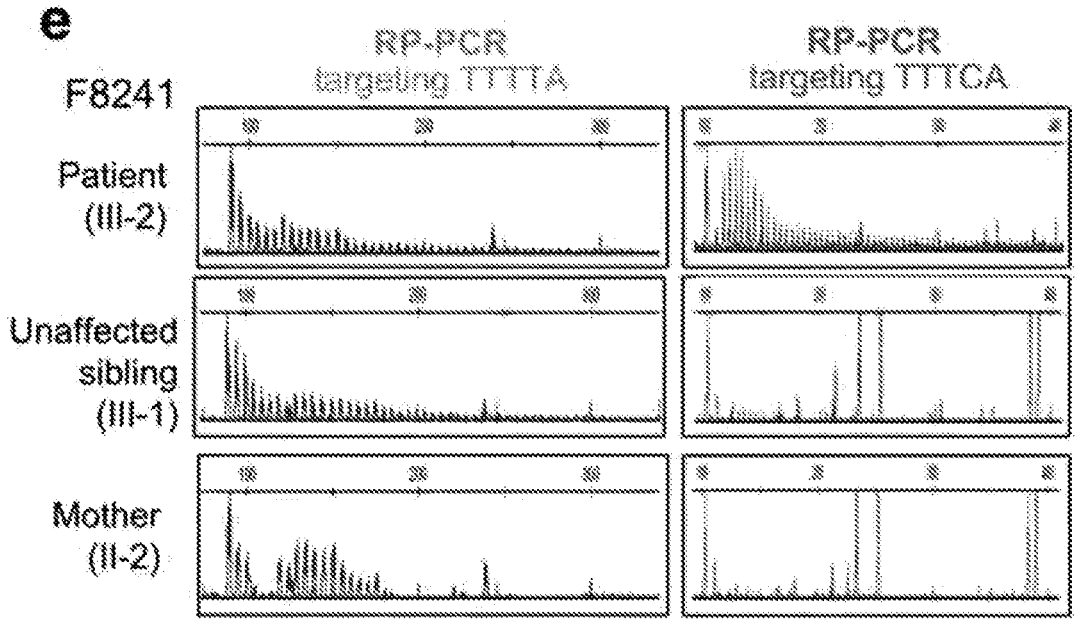
[Fig. 6F]
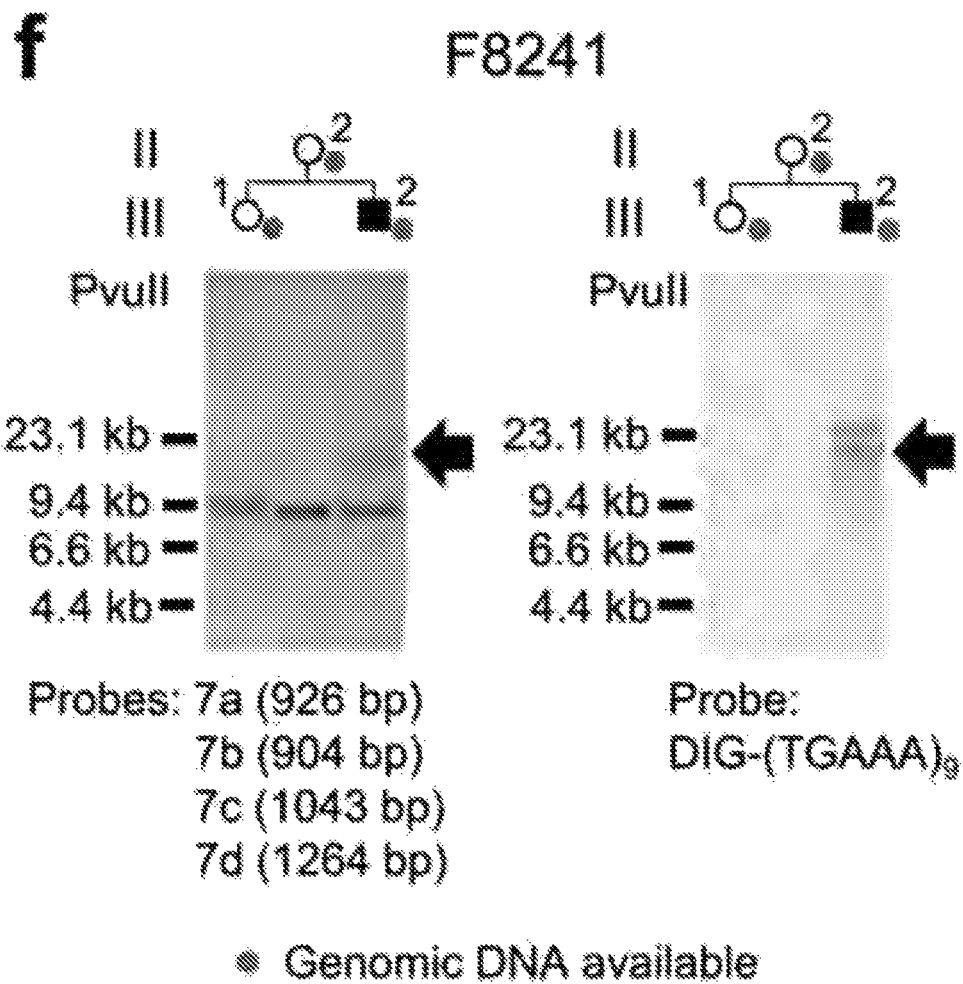

[Fig. 7]

| | |
|---|---|
| Reference genome | ...TATCCCCCTTTTCATTTTGTTCATTTTATTTTATTTT---ATTTTATTTTATTTTATTTTA... |
| Short read (mutant allele, II-6 in F6906) | ...TATCCCCCTTTTCATTTTGTTCATTTTATTTTATTTTTTATTTTATTTTA |
| Short read (mutant allele, II-3 in F8135) | ...TATCCCCCTTTTCATTTTGTTCATTTTATTTTATTTTTTATTTTATTTTA (TTTTA)₁₆TTT |

TTTTA repeat expansion

SAMD12 — exon 4 — (TTTTA)₇(TTA)(TTTTA)₁₃ — exon 5

| | |
|---|---|
| Short read (mutant allele, II-6 in F6906) | (TTTCA)₆TTTCATTTCATTTCATTTCATTTCATT-GAGACAGAGTTTCACTCTTGTTGCCCAGG... |
| | TTTCA repeat expansion |
| Reference genome | ...TTTTATTTTATTTTATTTTATTTTATTTTATTTGAGACAGAGTTTCACTCTTGTTGCCCAGG... |

Short read aligned to upstream region of repeat in SAMD12 showing TTTTA repeat expansion

*SAMD12*  ← Direction of transcription 2.2 kb

SacI — Chr8:119,379,052-119,379,172 — SacI 119,378,387 — 119,379,369-119,379,876 — 119,380,625

Probe 1a (508 bp)

119,379,992-119,380,624

Probe 1b (633 bp)

Schematic representations of the positions of the repeat, the probes used for Southern blot analysis, and the restriction sites

*TNRC6A*  → Direction of transcription 4.4 kb

EcoRI — Chr16:24,624,761-24,624,850 — EcoRI 24,621,269 — repeat — 24,625,715

24,622,448-24,622,649
Probe 6a (202 bp)

24,622,628-24,623,119
Probe 6b (492 bp)

Schematic representations of the positions of the repeat, the probes used for Southern blot analysis, and the restriction sites

[Fig. 8C]
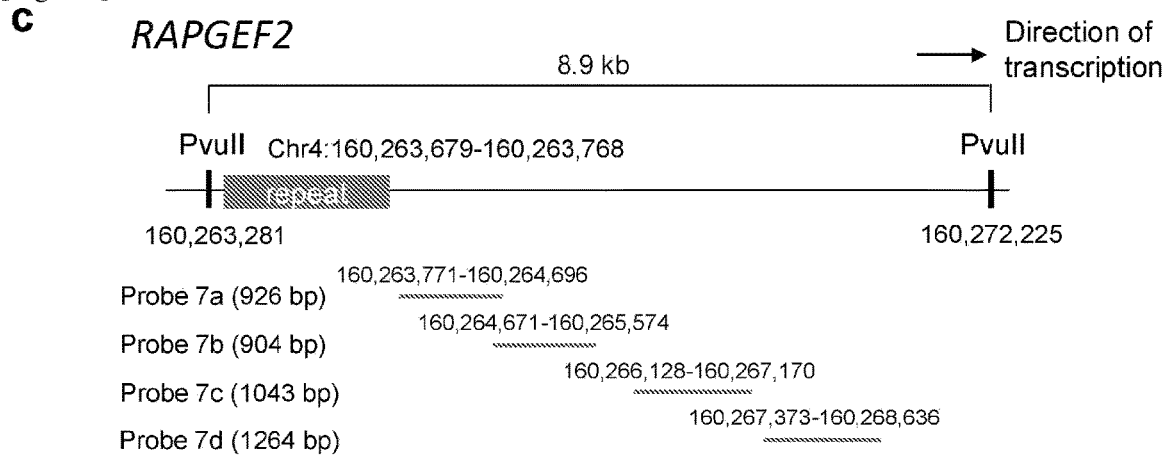
Schematic representations of the positions of the repeat, the probes used for Southern blot analysis, and the restriction sites
[Fig. 8D]
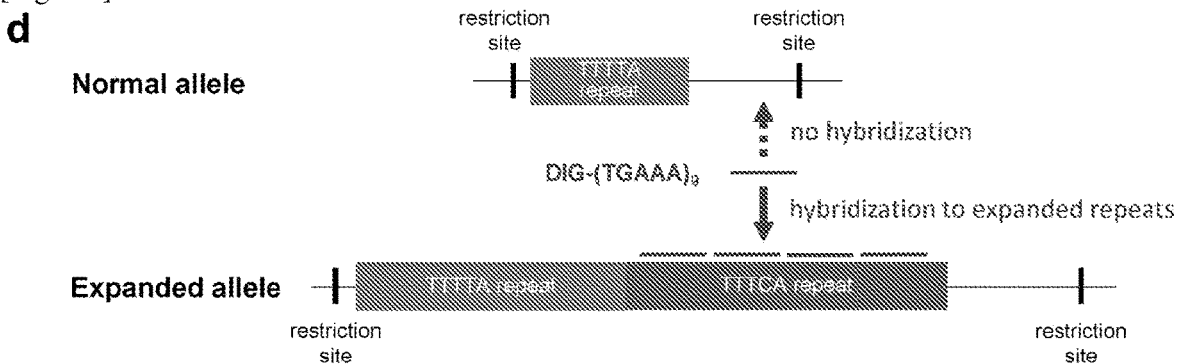
Schematic representations of the positions of the repeat, the probes used for Southern blot analysis, and the restriction sites

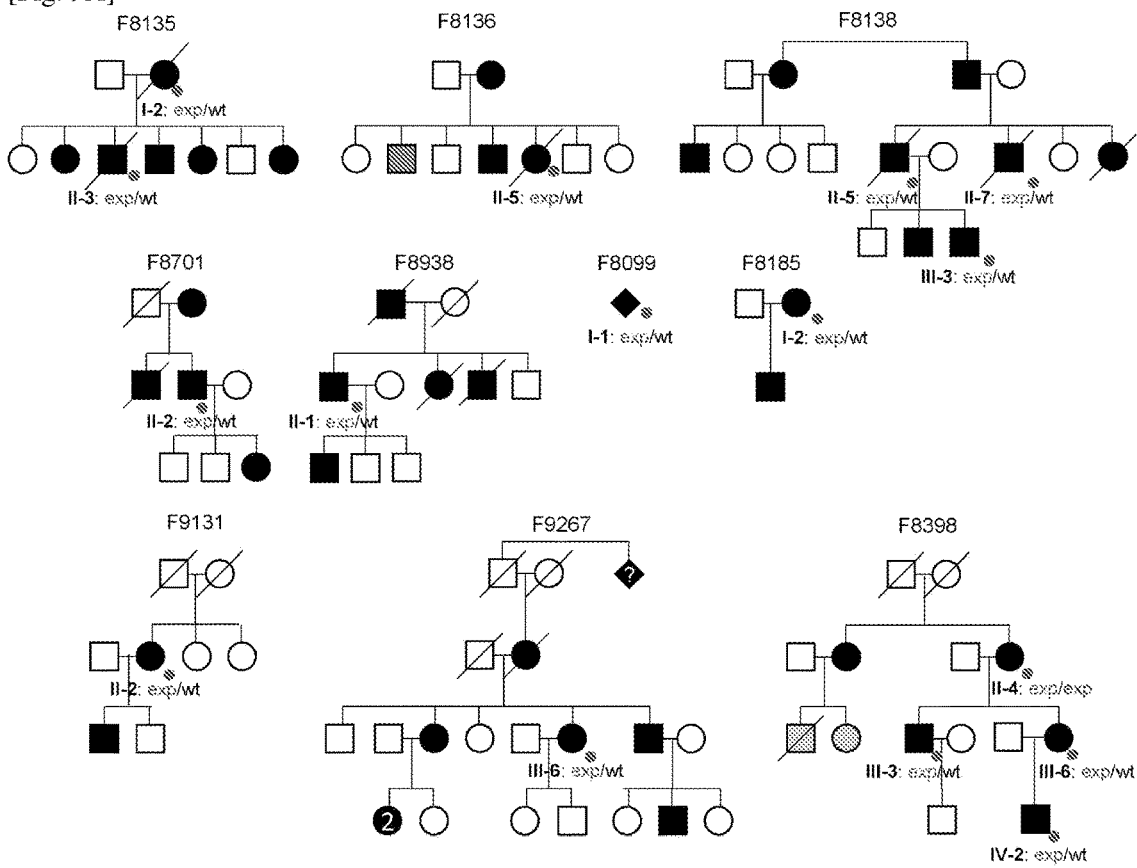
Families with repeat expansion mutations in *SAMD12* (repeat configuration 1)
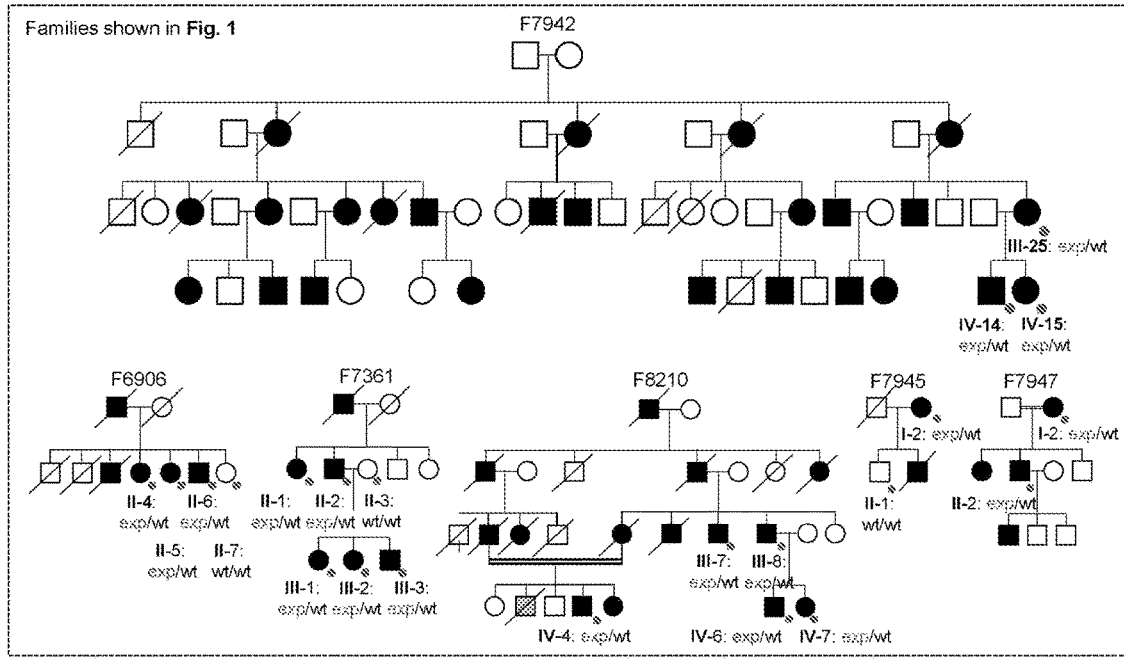
Families with repeat expansion mutations in *SAMD12* (repeat configuration 1)

[Fig. 9C]
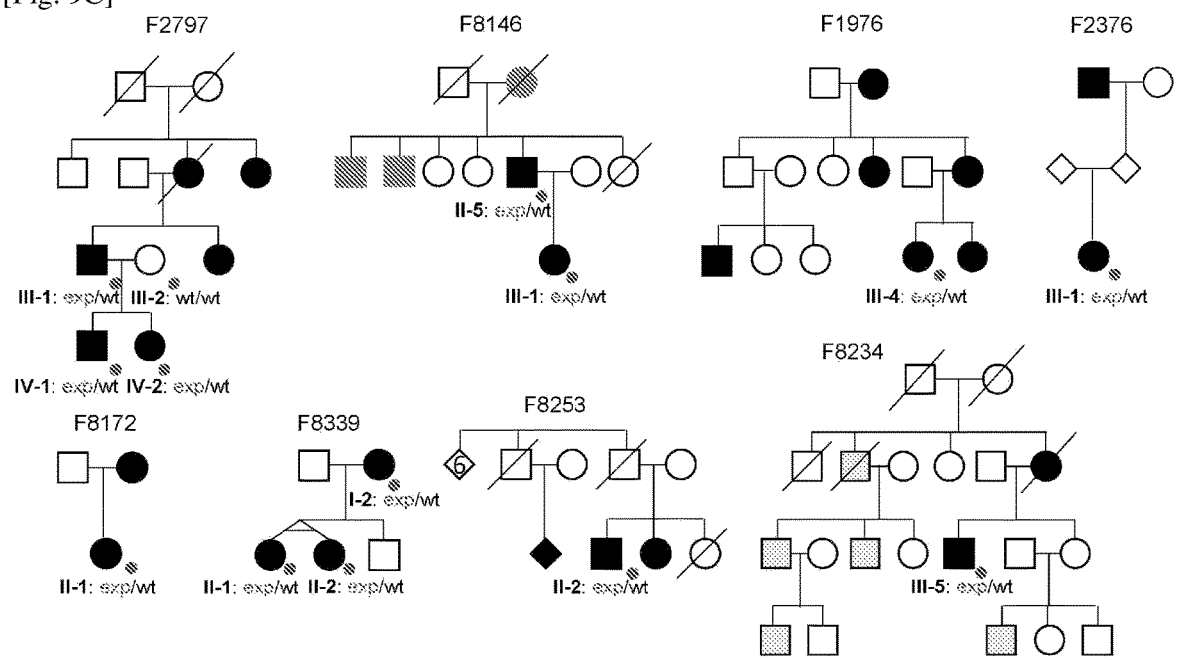
**Families with repeat expansion mutations in *SAMD12* (repeat configuration 1)**
[Fig. 9D]
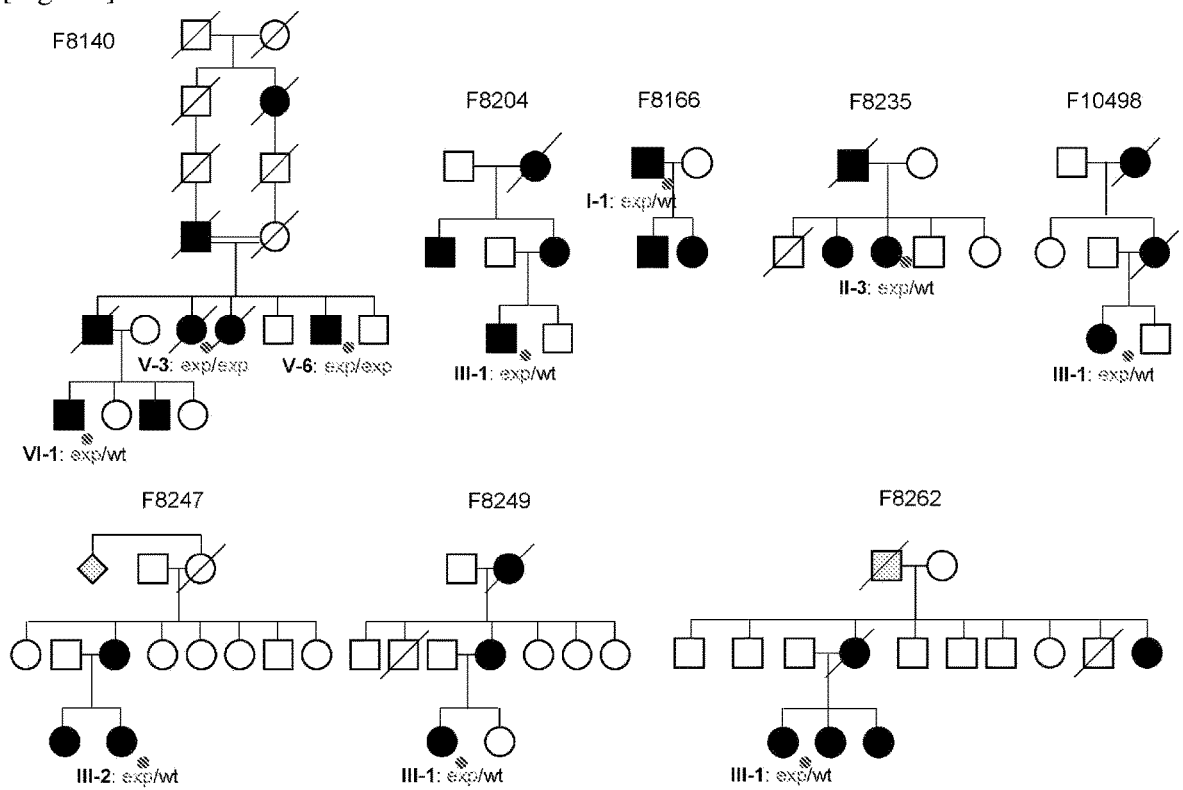
**Families with repeat expansion mutations in *SAMD12* (repeat configuration 1)**

[Fig. 9E]

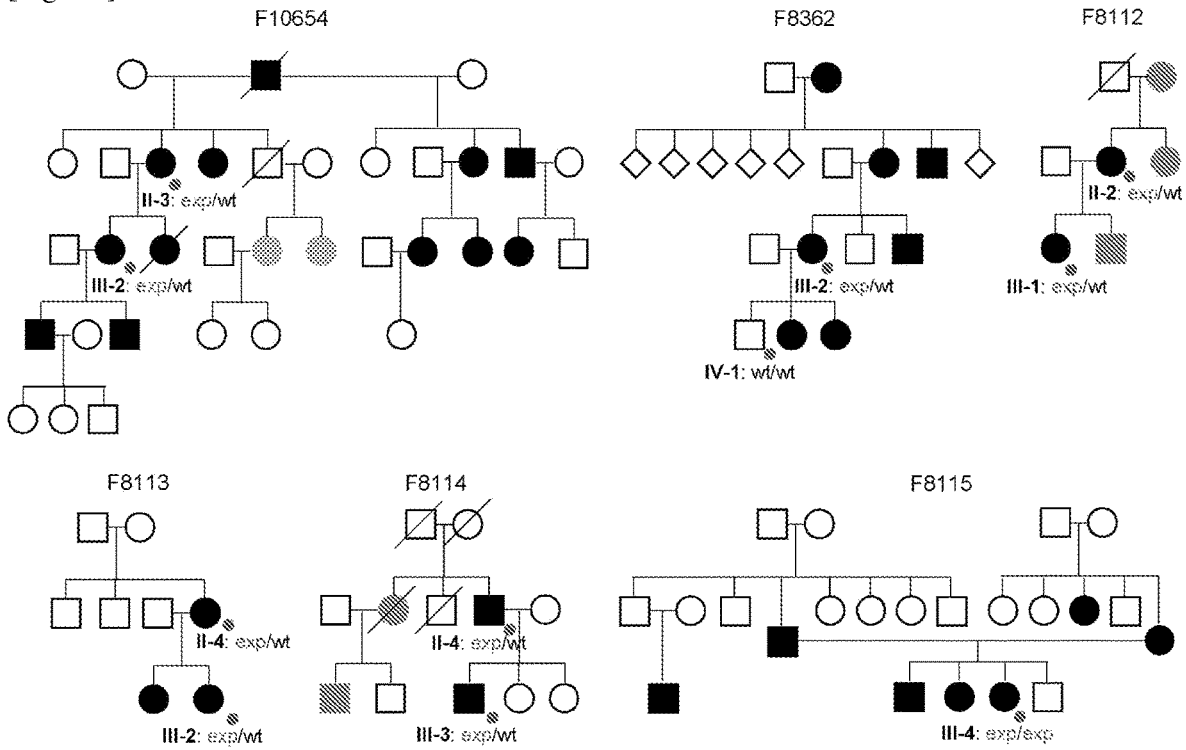

Families with repeat expansion mutations in *SAMD12* (repeat configuration 1)

[Fig. 9F]

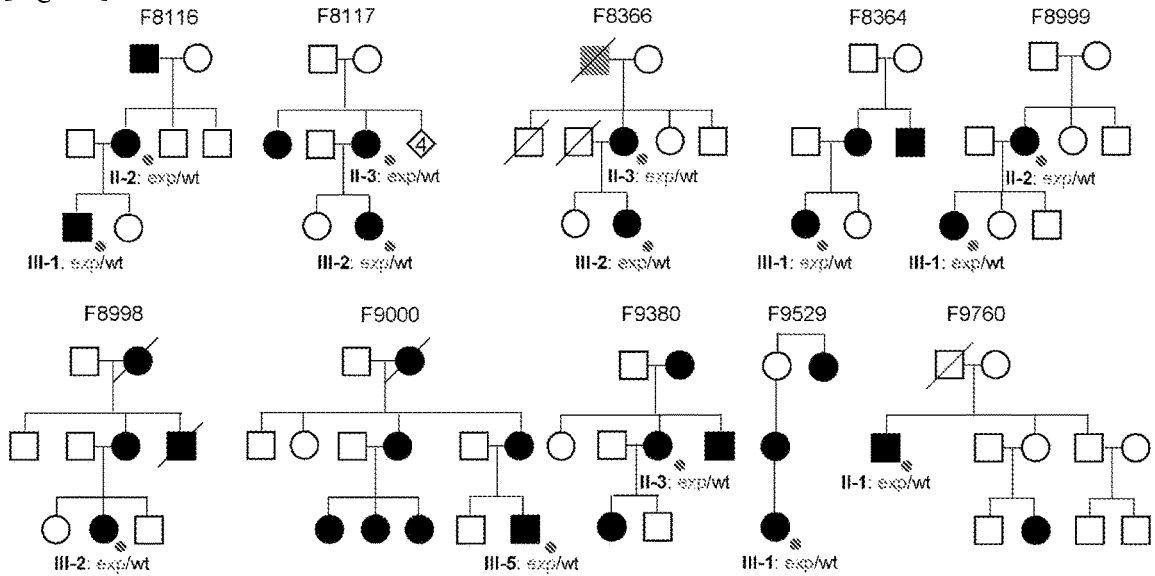

Families with repeat expansion mutations in *SAMD12* (repeat configuration 1)

Affected individuals are indicated by filled symbols. A diagonal line through a symbol indicates a deceased individual. Symbols with red dots represents individuals whose genomic DNA samples were available.

[Fig. 10]

| Marker | Physical position (hg19) | Haplotype of F6906 (repeat configuration 1) | Haplotype of F6115 (repeat configuration 2) | Minor allele frequency |
|---|---|---|---|---|
| rs4637872 | 119,293,911 | G | A | A: 0.60, G: 0.40 |
| rs3900767 | 119,307,293 | G | A | G: 0.82, A: 0.18 |
| rs7464659 | 119,332,157 | A | A | A: 0.83, G: 0.17 |
| rs59797347 | 119,333,061 | T | T | not registered in 1kJPN |
| rs2450222 | 119,343,669 | A | A | G: 0.21, A: 0.79 |
| rs6994270 | 119,348,495 | G | G | C: 0.88, G: 0.12 |
| rs2514941 | 119,349,285 | G | G | A: 0.32, G: 0.68 |
| rs34200541 | 119,349,531-119,349,532 | TG | TG | not registered in 1kJPN |
| rs2450315 | 119,350,656 | C | C | T: 0.30, C: 0.70 |
| rs2450203 | 119,352,278 | A | A | C: 0.31, A: 0.69 |
| rs111553876 | 119,354,490-119,354,491 | delCA | delCA | not registered in 1kJPN |
| rs764446520 | 119,354,532 | insAAA | insAAA | not registered in 1kJPN |
| - | 119,355,641 | insG | insG | not registered in dbSNP |
| rs2515029 | 119,356,466 | C | C | T: 0.14, C: 0.86 |
| rs2515028 | 119,357,221 | C | C | G: 0.14, C: 0.86 |
| rs17828843 | 119,368,718 | G | G | G: 0.85, A: 0.15 |
| rs9643124 | 119,376,989 | G | G | G: 0.84, T: 0.16 |
| 3' end of the repeat | 119,379,054 | - | A | |
| Mutation | 119,379,055-119,379,157 | - (TGAAA)$_{exp}$ (TAAAA)$_{exp}$ | (TAAAA)$_{exp}$ (TGAAA)$_{exp}$ (TAAAA)$_{exp}$ | |
| rs10086119 | 119,389,854 | G | G | A: 0.14, G: 0.86 |
| rs12678322 | 119,394,878 | A | A | A: 0.86, G: 0.14 |
| rs5894426 | 119,399,723 | insTAA | insTAA | not registered in 1kJPN |
| rs4876820 | 119,403,640 | T | T | T: 0.71, C: 0.29 |
| rs9297585 | 119,405,199 | A | A | A: 0.71, G: 0.29 |
| rs12546245 | 119,407,926 | G | G | not registered in 1kJPN |
| rs62533397 | 119,418,994 | C | T | C: 0.86, T: 0.14 |
| rs7827332 | 119,424,808 | A | G | A: 0.83, G: 0.17 |

**Disease haplotypes of families with repeat configurations 1 and 2 in *SAMD12***

[Fig. 11A]
a
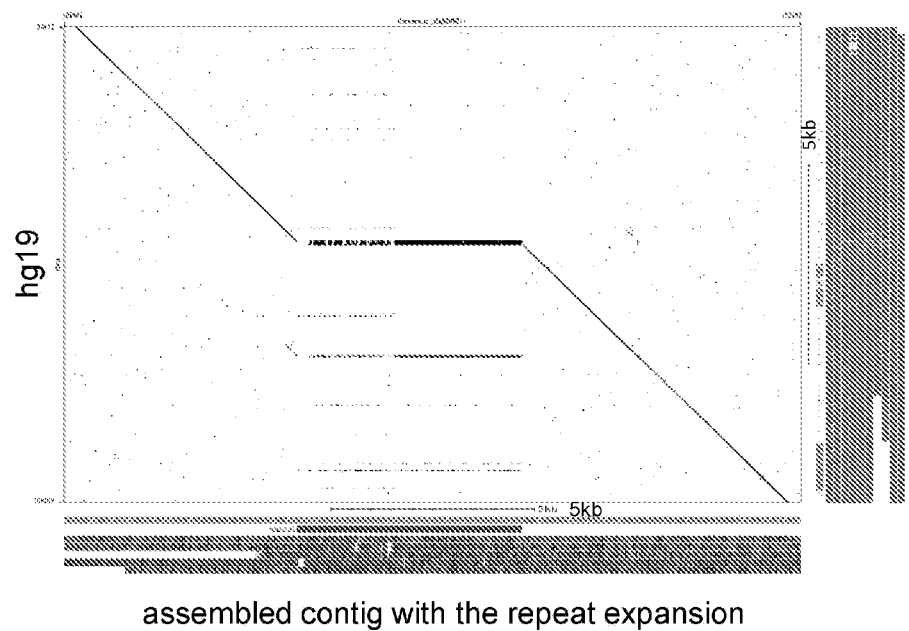
assembled contig with the repeat expansion
Dot plot of assembled Nanopore reads indicating the repeat expansion
[Fig. 11B]
b
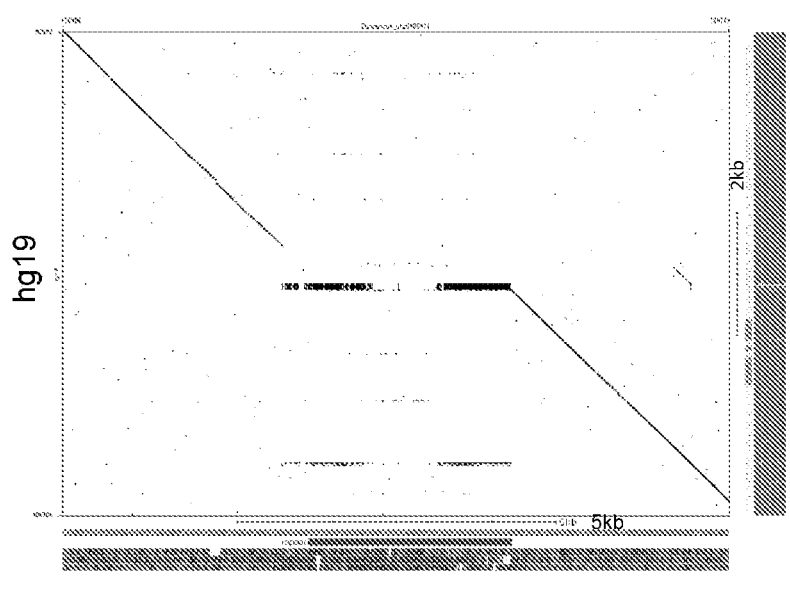
assembled contig with the repeat expansion
Dot plot of assembled Nanopore reads indicating the repeat expansion

[Fig. 12A]

a   II-6 in F6906 (repeat configuration 1)

*[Nanopore sequencing read consisting of many lines of TTTTA-like repeats followed by TTTCA-like repeats. The upper block is annotated "Mainly TTTTA repeats" and the lower block "Mainly TTTCA repeats".]*

Nanopore reads indicating the repeat expansion in *SAMD12* using 1D² technology

[Fig. 12B]

b   (TTTTA)$_{598}$ (TTTCA)$_{458}$

**Nanopore reads indicating the repeat expansion in *SAMD12* using 1D² technology**

[Fig. 12C]

| c | Match ratio |
|---|---|
| Observed read (part 1) vs pure TTTTA repeat | 87% |
| Observed read (part 2) vs pure TTTCA repeat | 91% |

**Nanopore reads indicating the repeat expansion in *SAMD12* using 1D² technology**

[Fig. 12D]

d II-1 in F6115 (repeat configuration 2)

```
TTTTATTTTATTTTATTTTATTTTATTTTATTTATTTTATTTTATTTTATTTTATTTTATTTTATTTTATTTTATTTTATTTTATTT
TATTTTATTTTATTTATTTTATTTTATTTTATTTTATTTTATTTATTTTATTTTATTTTATTTTATTTTATTTTATTTTATTTTATTT
TATTTTATTTTATTTTATTTTATTTTATTTTATTTTATTTTATTTTATTTATTTTATTTTATTTGTTTTATTTTGTTTTGATT
TTATTTTATTTTATTTTATTTTATTTTATTTGTTTTGTTTTATTTATTTTATTTTATTTGTTTTATTTTATTTATTTTGTTT
ATTTTATTTTATTTTATTTTATTTTATTTTATTTTATTTTATTTTATTTTATTTTATTTATTTTATTTTGTTTATTTTATT
TTTATTTTGTTTATTTTATTTTATTTTATTTGTTTATTTTATTTTATTTTATTTTATTTTATTTTATTTTATTTTATTTTATTTT
ATTTATTTTATTTTATTTTATTTTATTTTATTTATTTTATTTTATTTTATTTTATTTCAATTTTATTTTATTTTATTTTGATTT
TATTTTATTTTATTTTATTTTATTTTATTTGTTTTATTTTATTTTATTTGTTTATTTTATTTTATTTATTTTATTTTGTTT
TCATTTCTTGTTTTATTTTATTTTATTTTATTTTATTTATTTTATTCATTTTATTTTATTTTATTTGTTTTATTTTATTTTATTTT
GTTTATTTTATTTTGTTTGATTTTATTTTATTTTATTTTATTTTATTTTATTTTATTTTATTTGTTTCATTTTATTTTATTTTATT
TTATTTTATTTTAATTTTATTTTATTTTATTTTATTTTATTTTATTTTATTTTATTTTTATTTTATTTTGTTTTATTTTATTTT
GTTTATTTTATTTATTTTATTTTATTTTATTTTATTTTATTTTATTTTTATTTTTATTTGTTTATTTATTTTATTTTATTTT
ATTTTATTTTATTTTATTTTATTTTGTTTTATTTTATTTTATTTTATTTATTTTATTTTATTTTATTTTATTTTATTTTATTT
TATTTATTTTATTTATTTA
TTTCATTTCATTTATCATTCATTTCATTTGTTTCATTTCATTTCATTTCATTTCATTTCATTTCATTCATTTCATTTCAT
TTCATTTCATTTCATTTATTTCATTTCATTTTCATTTATTTCGTTTCATTTCATTTCATTTCATTTCATTTTATTTCATTT
CATTTCATTTCATTTCATTTCATTTCATTTCATTTCATTTCATTTCATTTTCATTTCATTTCATTTCATTTCATTT
CATTTCATTTCATTCATTTCATTTATTTCATTTCATTTCATTTATTTCATTTCATTTTCATTCATTTTCATTTCATTCATT
TCAGCTGTTTCATTTCATTTCATTTCTATTTCATTTCATTTCATTTCATTTCATTTCATTTCATTTCATTTCATTTATTC
ATTTCATTTCATTTCATTTCATTTCATTTATTTCATTTCATTTTATTTCATTTCATTTTATTTCATTTCATTTCTA
TTTCATTTCATTTCATTTTATTTCATTTCATTTATTTCATTCGTTTCATTTCATTTCATTTCATTTCATTTCATTTCATT
TTCATTTCATTTCATTTCATTTCATTTCATTTCATTTCATTTCATTTCATTTCATTTCATTTCATTTCATTTCATTTCATT
TCATTTCATTCATTTCATTTCATTTCAAGTTTCATTTCATTTCATTTCATTTCATTTCATTTCATTTCATTTCATT
TCATTTCATTTCATTTCATTTCATTTCATTTCATTTCATTTCATTTCGTTTCATTTCATTTTATTTCATTTCATTT
CATTTCATTTCATTTCATTTCATTTATTTCGTTTCATTTCATTTATTTCATTCATTTCATTTCATTTCATTTCATTTCATT
TCATTTCATTTCATTTCATTTCATTTGTTTCATTTCATTTATTTCATTCATTTCTCTATTTTCATTTCATTTCATTCATT
TCATTTATTCATTTCATTTTATTTCATTTATTTCATTTCATTTCTTTTCATTTCATTTCATTTCATTTCATTTCATTTCAT
TTCATTTCATTTCATTTCATTTCATTTCATTTCATTTCATTTCTCATTTCATTTTCATTTCGACTTTCA
TTTTATTTTATTTATTTTATTTTATTTTATTTGTTTATTTTATTTTATTTTATTTTATTTTATTTTATTTTATTTTATTTTATT
TGTTTATTTTATTTATTTTATTTTATTTTATTTTATTTTATTTTATTTTATTTTATTTTATTTTATTTTATTTTATTTTATTTT
ATTTTATTTTATTTTATTTTATTTTATTTTATTTTATTTTATTTTATTTTATTTTATTTTATTTTATTTTATTTTATTTTATTTTA
TTTTATTTATTTTATTTTATTTTATTTTATTTTGATGATTTTATTTTATTTTATTTTATTTTATTTTATTTTATTTTATTT
TATTTTATTTTATTTTATTTTATTTTATTTTATTTTATTTTGTTTTATTTTTATTTTGTTTTA
```

Mainly TTTTA repeats

Mainly TTTCA repeats

Mainly TTTTA repeats

**Nanopore reads indicating the repeat expansion in *SAMD12* using 1D² technology**

[Fig. 12E]

e  $(TTTTA)_{221} (TTTCA)_{225} (TTTTA)_{81}$

**Nanopore reads indicating the repeat expansion in *SAMD12* using 1D² technology**

[Fig. 12F]
| | Match ratio |
|---|---|
| Observed read (part 3) vs pure TTTTA repeat | 88% |
| Observed read (part 4) vs pure TTTCA repeat | 89% |
| Observed read (part 5) vs pure TTTTA repeat | 90% |
**Nanopore reads indicating the repeat expansion in *SAMD12* using 1D² technology**
[Fig. 13A]
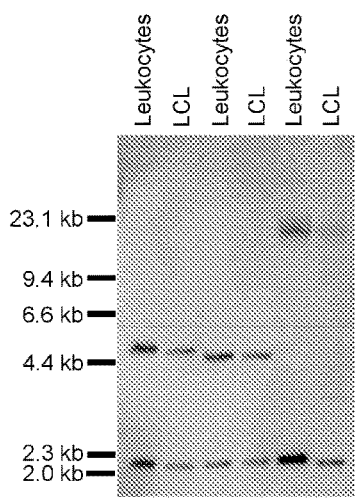
**Somatic instability of the repeat expansion in *SAMD12* in various tissues/cells**

[Fig. 13B]
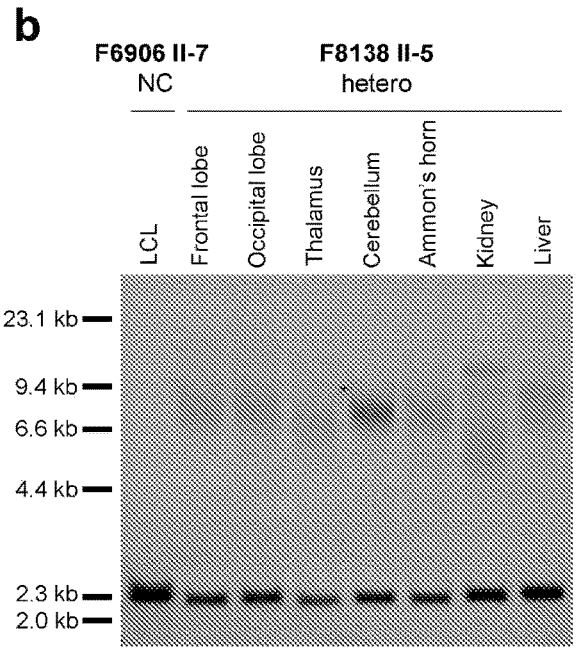
Somatic instability of the repeat expansion in *SAMD12* in various tissues/cells
[Fig. 13C]
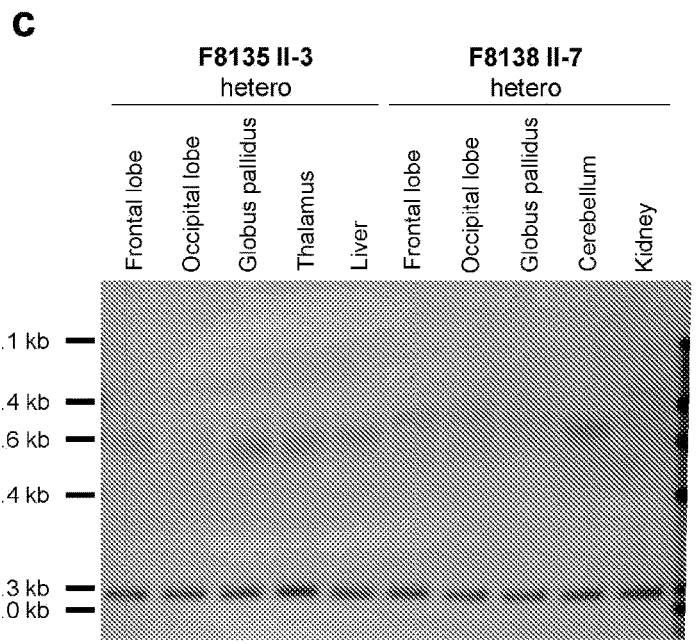
Somatic instability of the repeat expansion in *SAMD12* in various tissues/cells

[Fig. 13D]
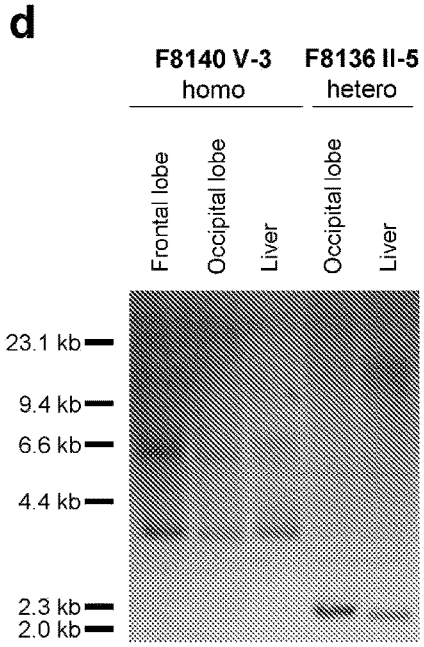
Somatic instability of the repeat expansion in *SAMD12* in various tissues/cells
[Fig. 14A]
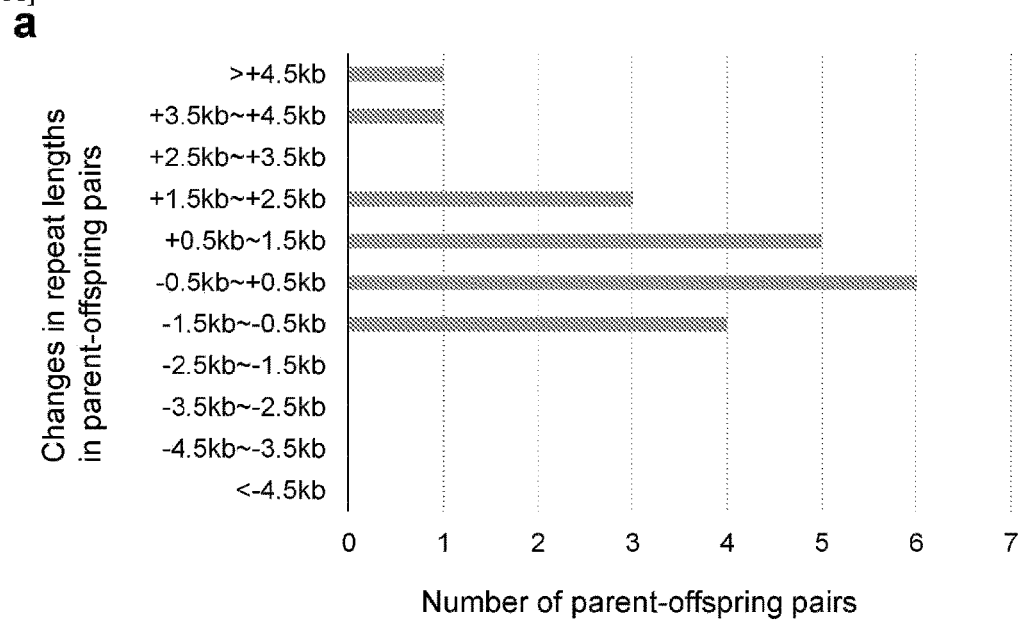
Intergenerational instability of repeat lengths in *SAMD12*

[Fig. 14B]
b
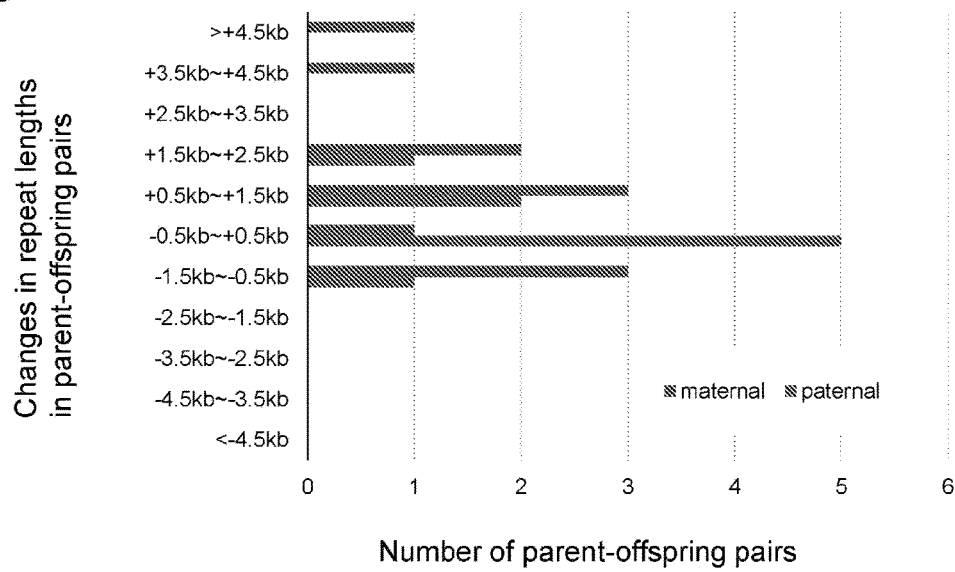
Intergenerational instability of repeat lengths in *SAMD12*
[Fig. 15]
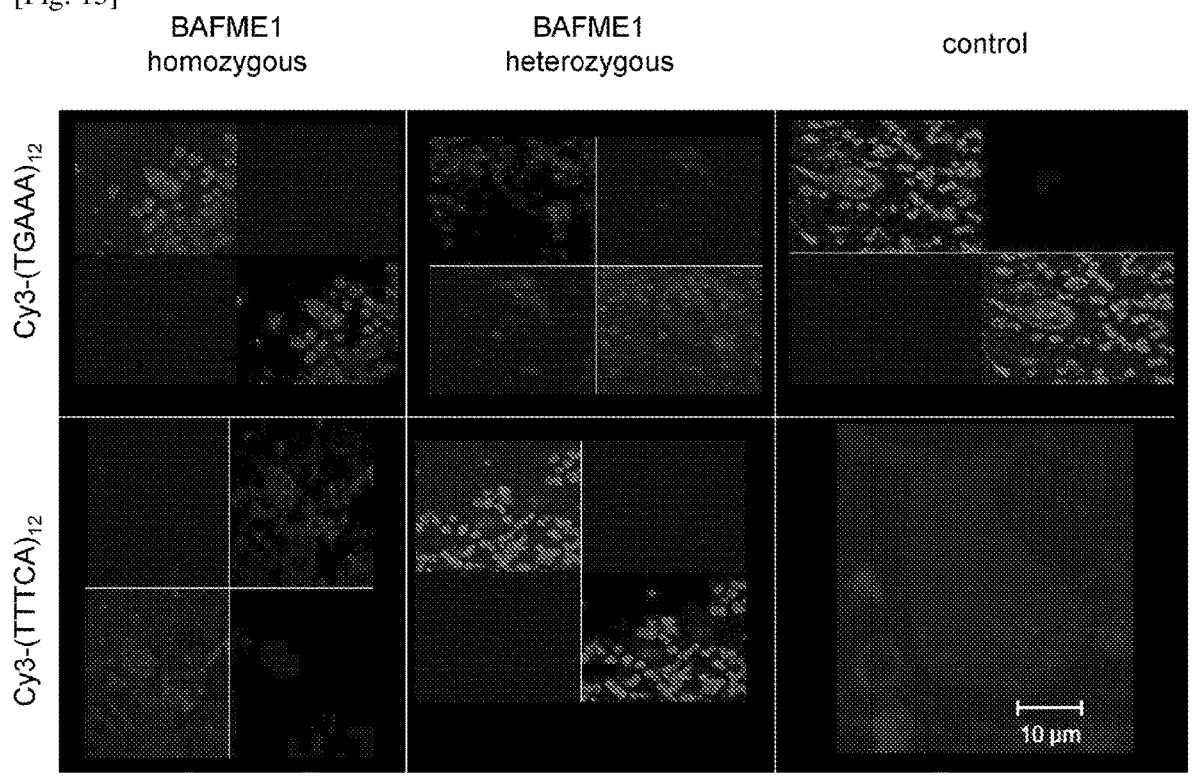
RNA foci observed in cerebella of patients carrying expanded repeats in homozygous or heterozygous state

[Fig. 16A]
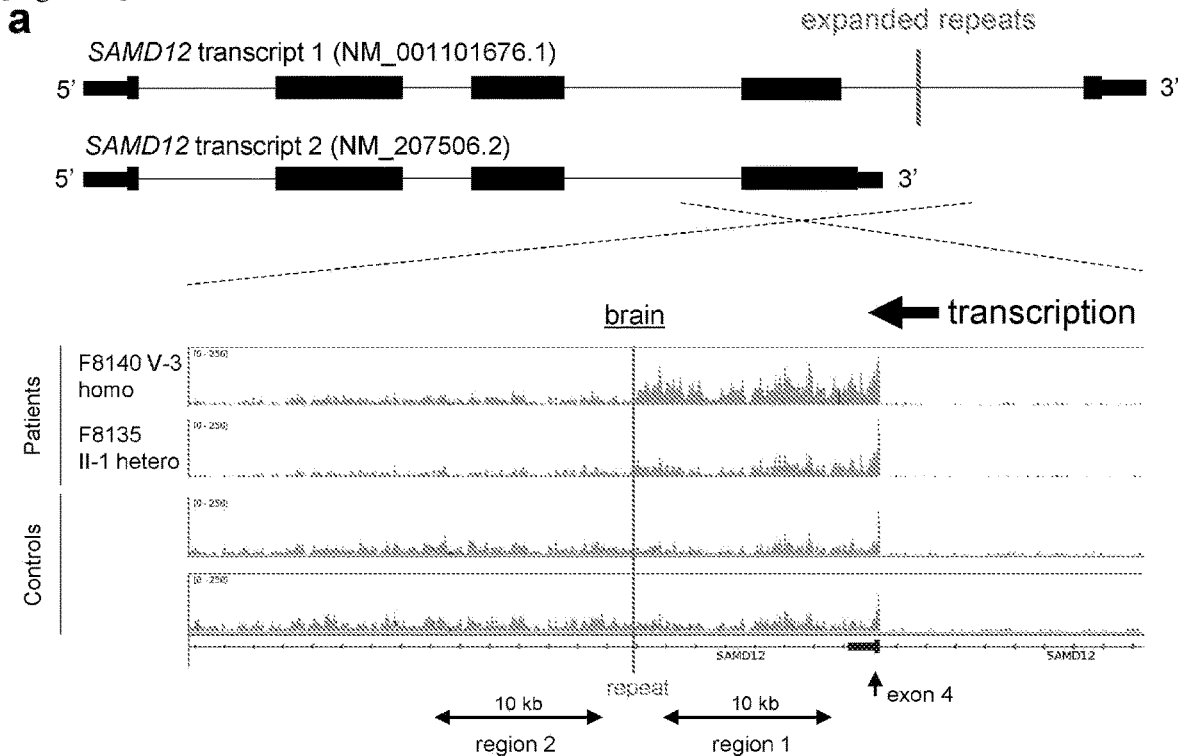
Abortive transcription in the brain was suggested by RNA-seq analysis
[Fig. 16B]
Abortive transcription in the brain was suggested by RNA-seq analysis
[Fig. 16C]
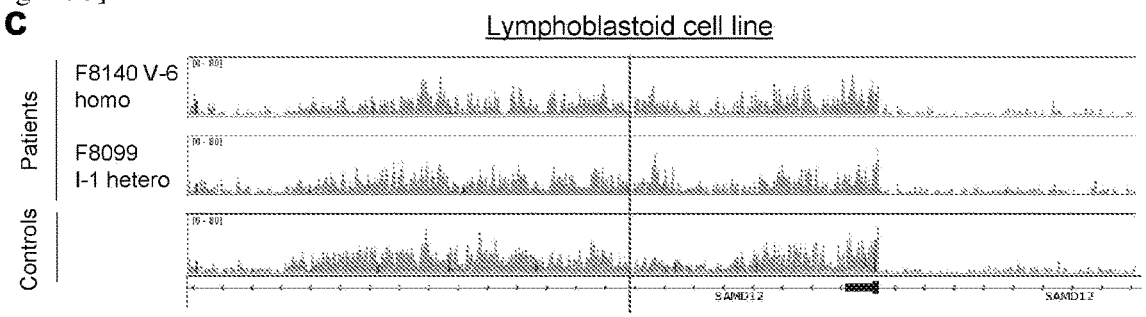
Abortive transcription in the brain was suggested by RNA-seq analysis

[Fig. 16D]
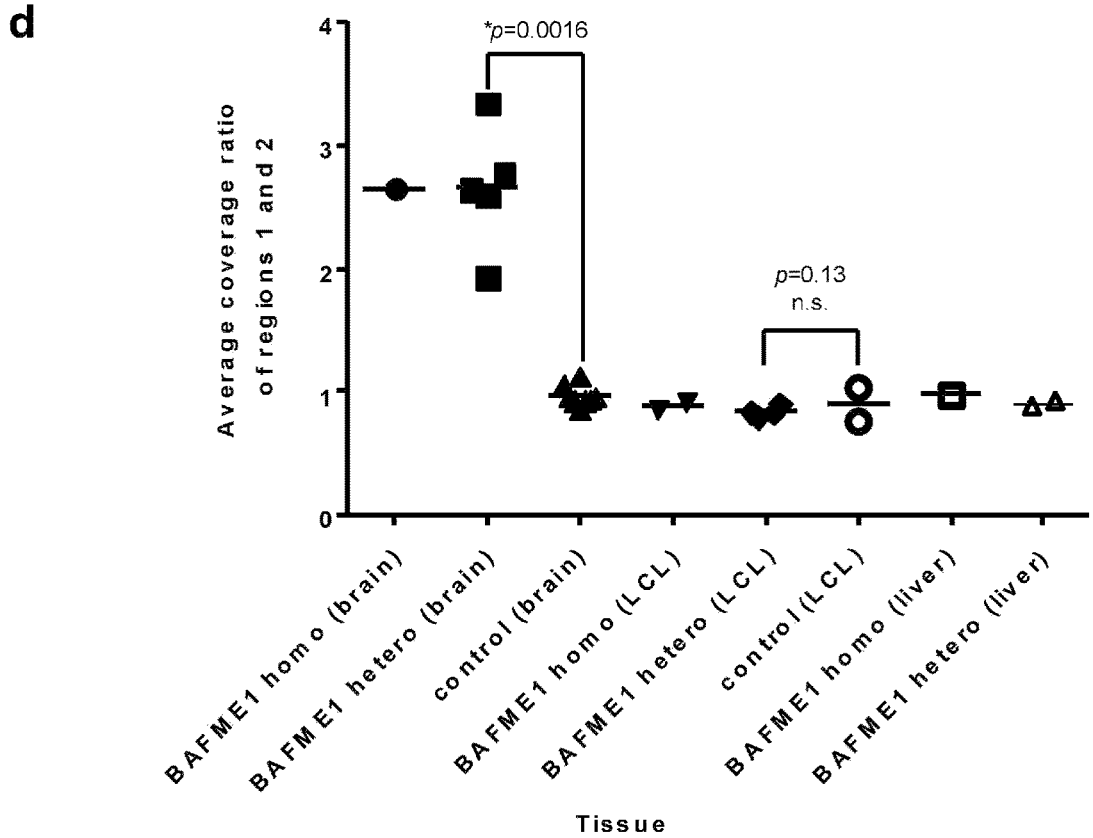
Abortive transcription in the brain was suggested by RNA-seq analysis
[Fig. 16E]
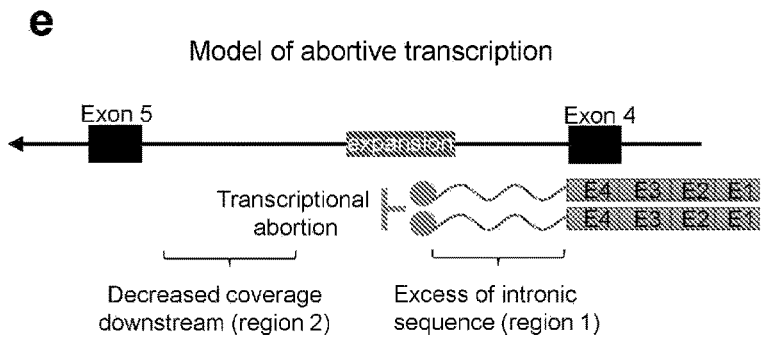
Abortive transcription in the brain was suggested by RNA-seq analysis

[Fig. 16F]
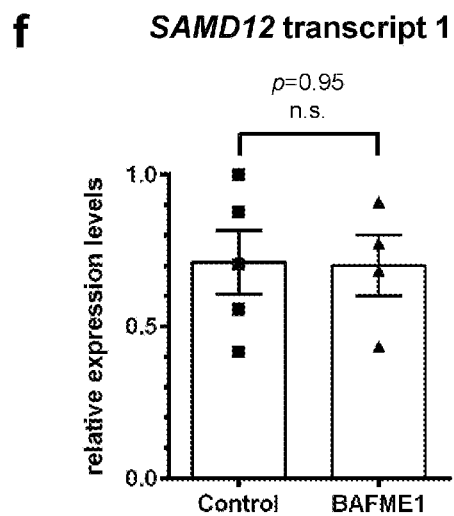
Abortive transcription in the brain was suggested by RNA-seq analysis
[Fig. 17A]
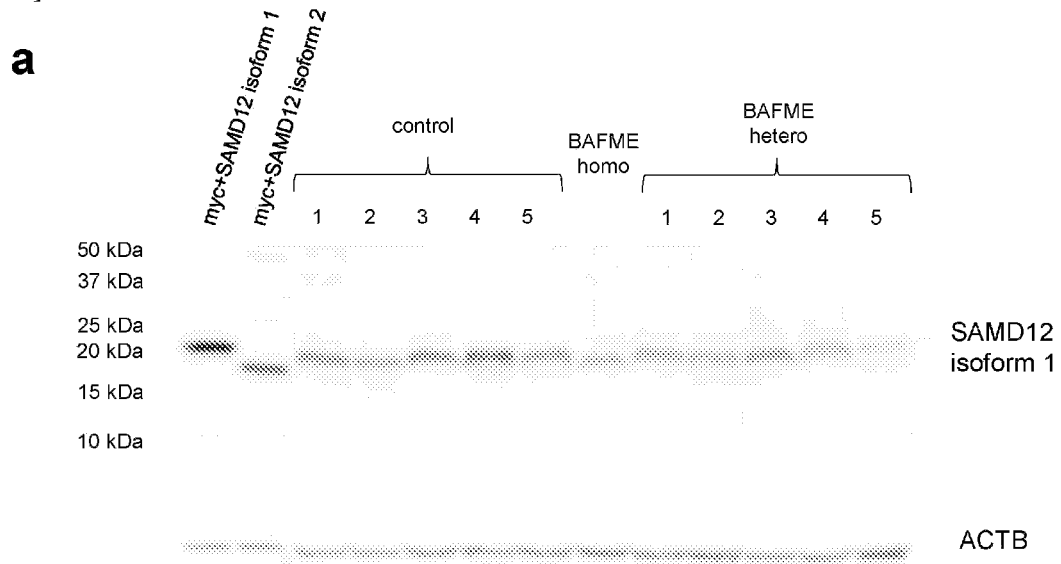
Expression levels of SAMD12 protein in brains

[Fig. 17B]
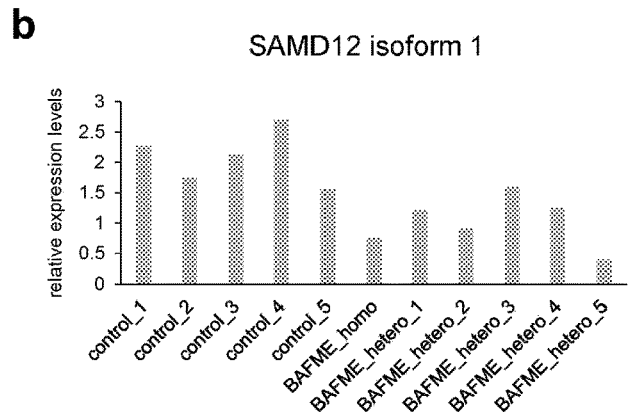
[Fig. 17C]
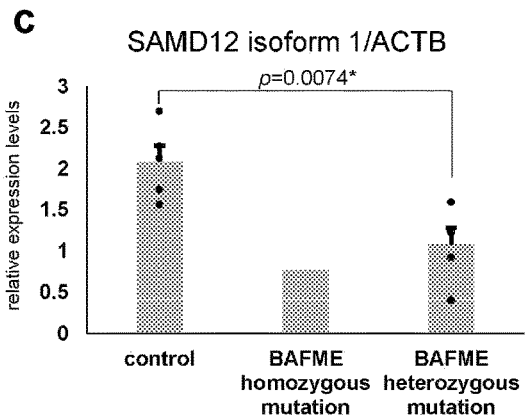
Expression levels of SAMD12 protein in brains
[Fig. 18]
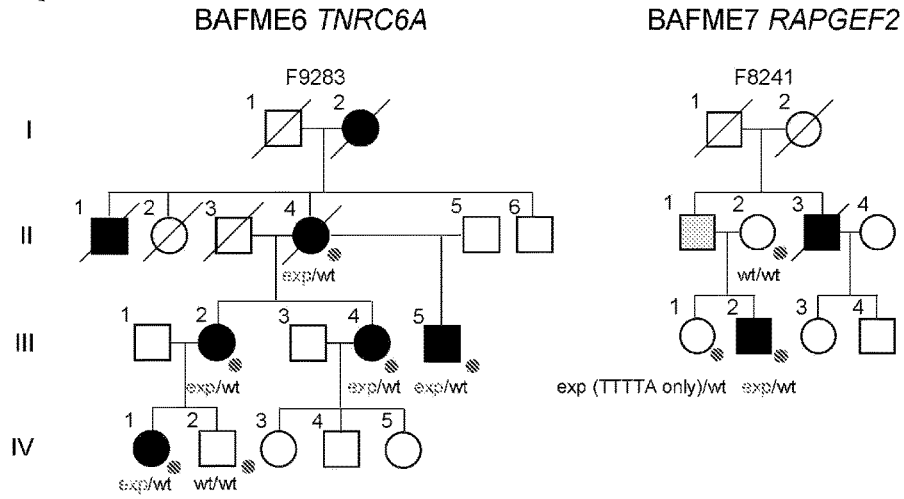
**TTTCA repeat expansions are identified in *TNRC6A* and *RAPGEF2* in F9283 and F8241, respectively**

[Fig. 19]
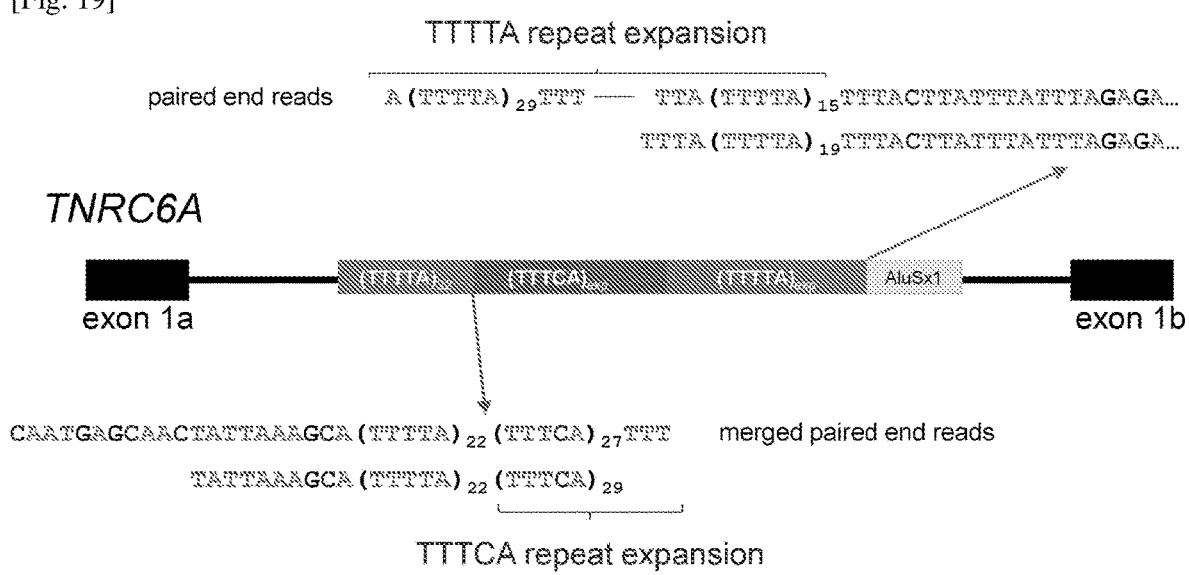
TTTCA and TTTTA repeat expansion in *TNRC6A*

[Fig. 20A]
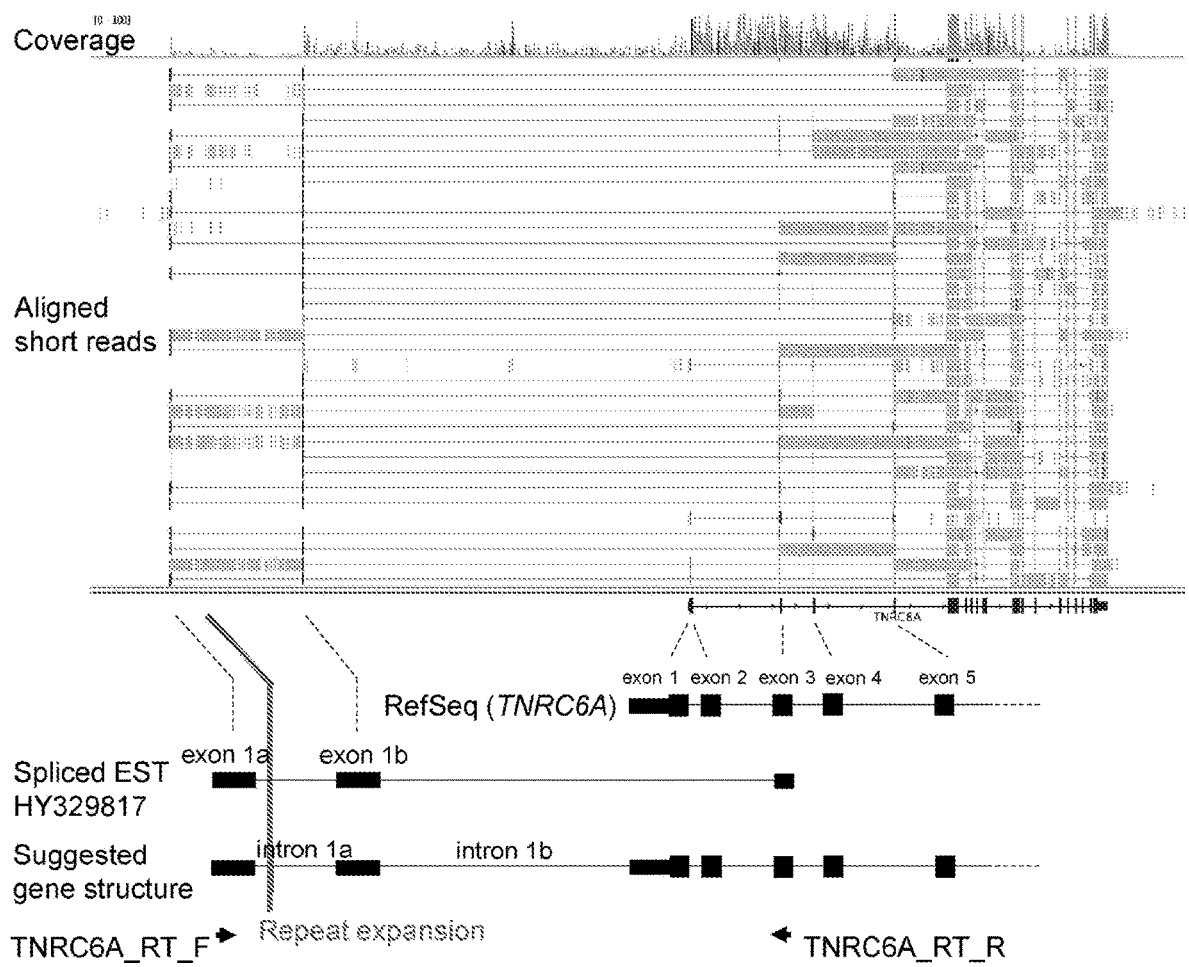
Localization of expanded TTTCA repeats in *TNRC6A*
[Fig. 20B]
Localization of expanded TTTCA repeats in *TNRC6A*

[Fig. 21A]
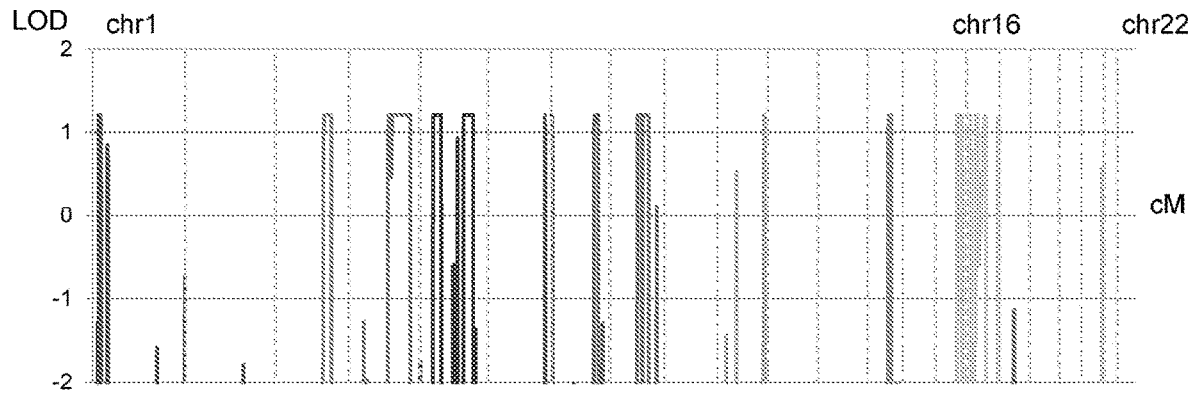
Parametric linkage analysis of BAFME6 family
[Fig. 21B]
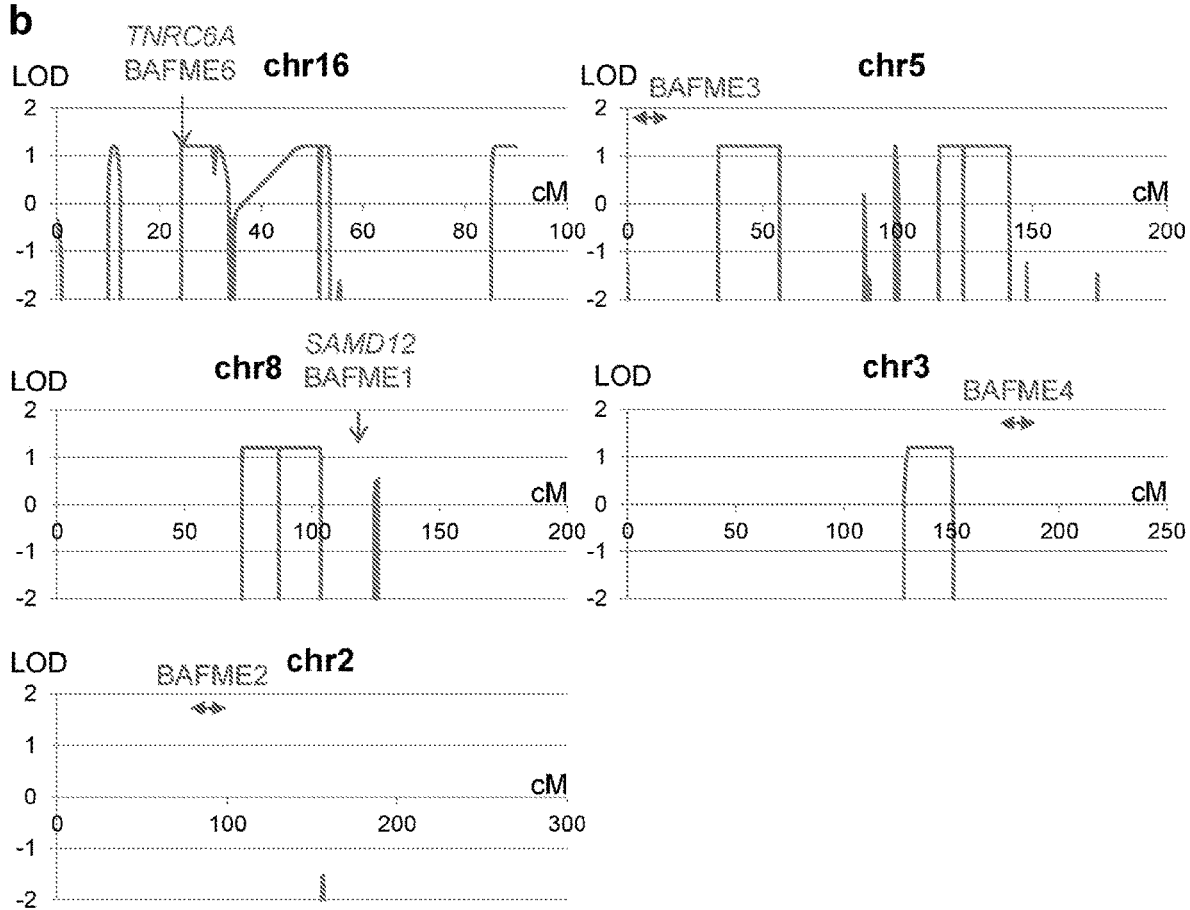
Parametric linkage analysis of BAFME6 family

[Fig. 22]
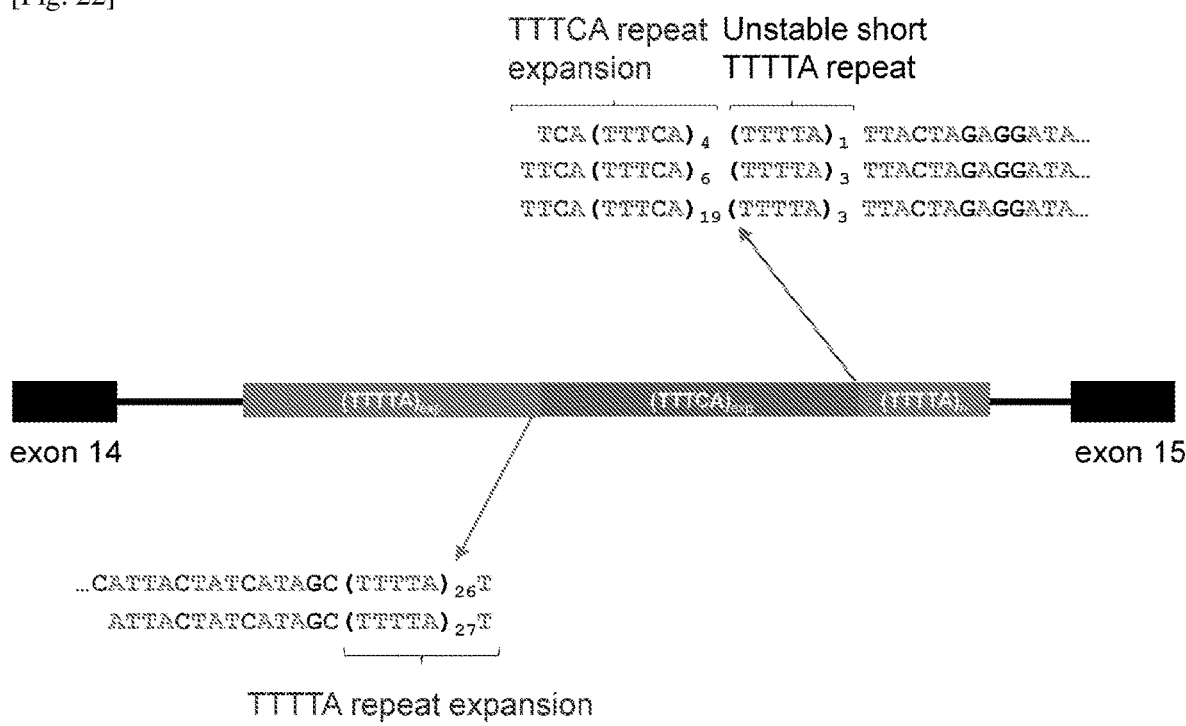
**TTTCA and TTTTA repeat expansion in *RAPGEF2***

[Fig. 23A]
a
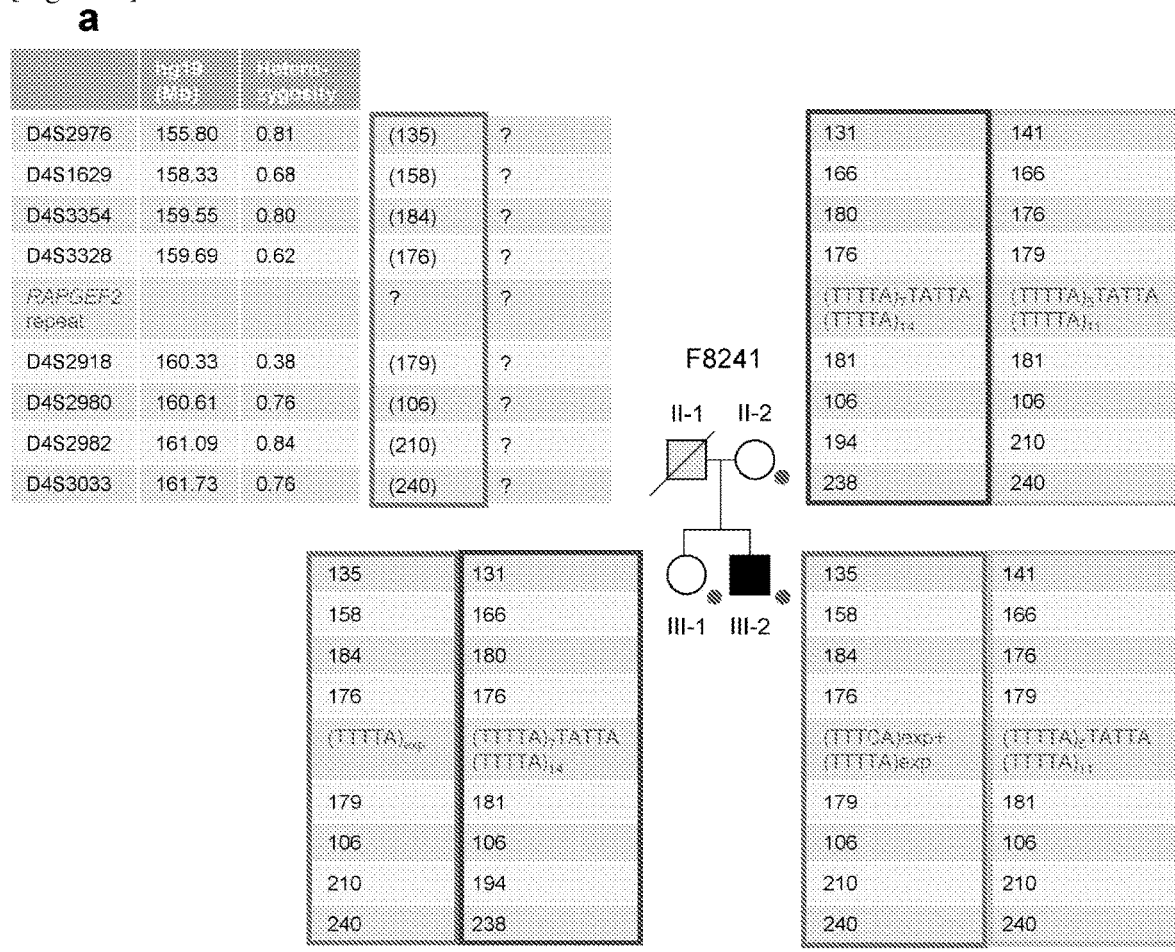
Haplotype analysis of F8241
[Fig. 23B]
b
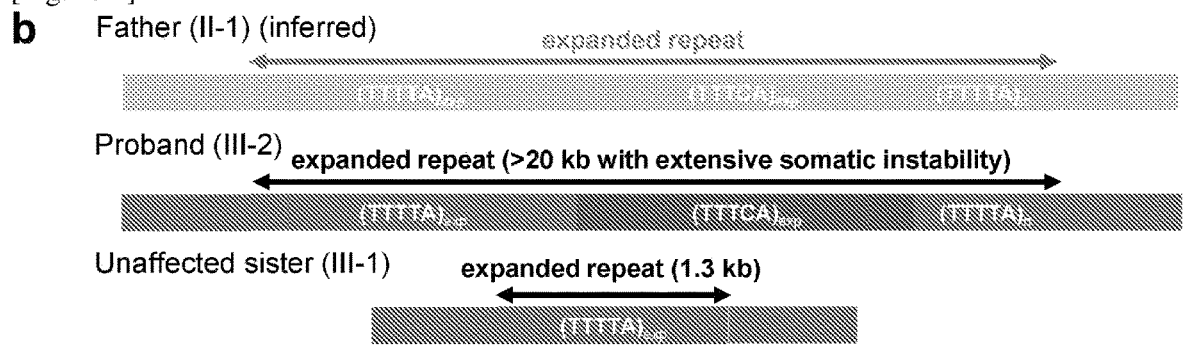
Haplotype analysis of F8241

[Fig. 24]

| Primers | Sequence |
|---|---|
| D8S1171i | |
| M13(-21)-D8S1171i-F | 5'-TGTAAAACGACGGCCAGTCAGTTCAAAGTGCGTAAAGTAC-3' |
| D8S1171i-R | 5'-CAAGTAGAGCTCACGATTAGTAAC-3' |
| Fam-M13(-21) | 5'-fam-TGTAAAACGACGGCCAGT-3' |
| D8S0379i | |
| M13(-21)-D8S0379i-F | 5'-TGTAAAACGACGGCCAGTATAAATGGCTGCATGCTAG-3' |
| D8S0379i-R | 5'-CTCAGATAATGGAATGAAGACTAA-3' |
| Fam-M13(-21) | 5'-fam-TGTAAAACGACGGCCAGT-3' |
| D8S522 | |
| M13(-21)-D8S522-F | 5'-TGTAAAACGACGGCCAGTGAAAACAAAACAGGCTCC-3' |
| D8S522-R | 5'-TGACCAAACAACTAGACACC-3' |
| Fam-M13(-21) | 5'-fam-TGTAAAACGACGGCCAGT-3' |
| D4S2976 | |
| M13(-21)-D4S2976F | 5'-TGTAAAACGACGGCCAGTTTCCACCCCCAAAAGA-3' |
| D4S2976R | 5'-CAAAGGTTTTTAACATCCCA-3' |
| Fam-M13(-21) | 5'-fam-TGTAAAACGACGGCCAGT-3' |
| D4S1629 | |
| M13(-21)-D4S1629F | 5'-TGTAAAACGACGGCCAGTTGGTTCTGCTTTTTCTCTCC-3' |
| D4S1629R | 5'-TTTAACAGACAAATGACAAATCTG-3' |
| Fam-M13(-21) | 5'-fam-TGTAAAACGACGGCCAGT-3' |
| D4S3354 | |
| M13(-21)-D4S3354F | 5'-TGTAAAACGACGGCCAGTGGTGACATAGGCATCACACA-3' |
| D4S3354R | 5'- TCTCCAATTCAGAGAGCTGC-3' |
| Fam-M13(-21) | 5'-fam-TGTAAAACGACGGCCAGT-3' |
| D4S3328 | |
| M13(-21)-D4S3328F | 5'- TGTAAAACGACGGCCAGTCCAAGATCACACTACTGCCC-3' |
| D4S3328R | 5'- AGCCTCCTCTGTCAAGGAGT-3' |
| Fam-M13(-21) | 5'-fam-TGTAAAACGACGGCCAGT-3' |
| D4S2918 | |
| M13(-21)-D4S2918F | 5'- TGTAAAACGACGGCCAGTGCAGAAGCCTGGTCAT-3' |
| D4S2918R | 5'- TCAGCCCCTTAATCACA-3' |
| Fam-M13(-21) | 5'-fam-TGTAAAACGACGGCCAGT-3' |
| D4S2980 | |
| M13(-21)-D4S2980F | 5'-TGTAAAACGACGGCCAGTCCTCAAGGTATCAGGCTGC-3' |
| D4S2980R | 5'-TTAAGTACATGGTCCGTCCC-3' |
| Fam-M13(-21) | 5'-fam-TGTAAAACGACGGCCAGT-3' |
| D4S2982 | |
| M13(-21)-D4S2982F | 5'-TGTAAAACGACGGCCAGTCCAGTCAACCCCAACAC-3' |
| D4S2982R | 5'-GAAATGAAACATGATGACACC-3' |
| Fam-M13(-21) | 5'-fam-TGTAAAACGACGGCCAGT-3' |
| D4S3033 | |
| M13(-21)-D4S3033F | 5'-TGTAAAACGACGGCCAGTTGCCTTTAAGAATGCAATG-3' |
| D4S3033R | 5'-TGGTGTCAACGCAGTAAAT-3' |
| Fam-M13(-21) | 5'-fam-TGTAAAACGACGGCCAGT-3' |

[Fig. 25]

| Primer | Sequence |
|---|---|
| **(1) Repeat-primed PCR analysis of *SAMD12* targeting TTTTA** | |
| P1, Fam-SAMD12_R | 5'-fam-CTTGAGCCCCAGACAAGAAT-3' |
| P2, M13R-AAAAT4 | 5'-CAGGAAACAGCTATGACC(AAAAT)$_4$-3' |
| P2anchor, M13R | 5'-CAGGAAACAGCTATGACC-3' |
| **(2) Repeat-primed PCR analysis of *SAMD12* targeting TTTCA** | |
| P3, Fam-SAMD12_F | 5'-fam-TGCTACTGTAAAAAGATAAACAAAATG-3' |
| P4, M13R-TTTCA5 | 5'-CAGGAAACAGCTATGACC(TTTCA)$_5$-3' |
| P4anchor, M13R | 5'-CAGGAAACAGCTATGACC-3' |
| **(3) Repeat-primed PCR analysis of *TNRC6A* targeting TTTCA** | |
| P5, TNRC6A_F | 5'-TGTGGAGCTCCAAAGCCCTG-3' |
| P6, M13(-21)-TGAAA5 | 5'-TGTAAAACGACGGCCAGT(TGAAA)$_5$-3' |
| P6anchor, Fam-M13(-21) | 5'-fam-TGTAAAACGACGGCCAGT-3' |
| **(4) Repeat-primed PCR analysis of *TNRC6A* targeting TTTTA** | |
| P7, TNRC6A_R | 5'-CCAAGTATGCTCCTTCCCTACTT-3' |
| P8, M13(-21)-TTTTA5 | 5'-TGTAAAACGACGGCCAGT(TTTTA)$_5$-3' |
| P8anchor, Fam-M13(-21) | 5'-fam-TGTAAAACGACGGCCAGT-3' |
| **(5) Repeat-primed PCR analysis of *RAPGEF2* targeting TTTTA** | |
| P9, RAPGEF2_intron14_F | 5'-TTAGTCATTTTCTCTGTCTGGGAG-3' |
| P10, M13(-21)-TAAAA5 | 5'-TGTAAAACGACGGCCAGT(TAAAA)$_5$-3' |
| P11anchor, Fam-M13(-21) | 5'-fam-TGTAAAACGACGGCCAGT-3' |
| **(6) Repeat-primed PCR analysis of *RAPGEF2* targeting TTTCA** | |
| P11, RAPGEF2_intron14_R | 5'-GCAGTATGTACACATAGCAGTGC-3' |
| P12, M13(-21)-TTTCA5 | 5'-TGTAAAACGACGGCCAGT(TTTCA)$_5$-3' |
| P12anchor, Fam-M13(-21) | 5'-fam-TGTAAAACGACGGCCAGT-3' |

[Fig. 26A]

a RNA-seq

| ID | Disease | Source | Number of reads | Read length | Number of reads filled with 5'-TTTCA or 5'TGAAA motif | Number of reads filled with 5'-CTTCA or 5'-TGAAG motif | Number of reads filled with 5'-GTTCA or 5'-TGAAC motif |
|---|---|---|---|---|---|---|---|
| F8136 I-1 | BAFME1 | liver | 155,503,230 | 101PE | 23 | 0 | 0 |
| F8140 V-3 | BAFME1 hom | liver | 156,933,316 | 101PE | 16 | 0 | 0 |
| F8135 II-1 | BAFME1 | liver | 137,428,560 | 101PE | 12 | 0 | 0 |
| F8140 V-6 | BAFME1 hom | LCL | 131,550,452 | 101PE | 23 | 0 | 0 |
| F8398 II-4 | BAFME1 hom | LCL | 139,338,450 | 101PE | 38 | 0 | 0 |
| F8398 III-3 | BAFME1 | LCL | 159,131,286 | 101PE | 67 | 0 | 0 |
| F8146 III-1 | BAFME1 | LCL | 155,302,968 | 101PE | 3 | 0 | 0 |
| F2376 III-1 | BAFME1 | LCL | 141,962,356 | 101PE | 40 | 0 | 0 |
| F8099 I-1 | BAFME1 | LCL | 140,966,042 | 101PE | 12 | 0 | 0 |
| F6115 I-1 | unaffected | LCL | 149,959,512 | 101PE | 0 | 0 | 0 |
| F6906 II-7 | unaffected | LCL | 150,014,140 | 101PE | 0 | 0 | 0 |

BAFME1; benign adult familial myoclonic epilepsy caused by TTTCA pentanucleotide repeat expansion in *SAMD12*,
BAFME6; benign adult familial myoclonic epilepsy caused by TTTCA pentanucleotide repeat expansion in *TNRC6A*,
BAFME7; benign adult familial myoclonic epilepsy caused by TTTCA pentanucleotide repeat expansion in *RAPGEF2*,
hom; homozygous, LCL; lymphoblastoid cell line, PE; paired end

DNA-seq

| ID | Disease | Source | Number of reads | Read length | Number of reads filled with 5'-TTTCA or 5'TGAAA motif | Number of reads filled with 5'-CTTCA or 5'-TGAAG motif | Number of reads filled with 5'-GTTCA or 5'-TGAAC motif |
|---|---|---|---|---|---|---|---|
| F6906 II-6 | BAFME1 | blood | 1,523,327,112 | 100PE | 400 | 0 | 0 |
| F8136 I-1 | BAFME1 | brain | 1,144,146,288 | 101PE | 1,112 | 10 | 1 |
| F8135 II-1 | BAFME1 | brain | 1,112,108,282 | 150PE | 323 | 9 | 0 |
| F8140 V-3 | BAFME1 hom | brain | 904,833,992 | 150PE | 526 | 3 | 0 |
| F9283 III-2 | BAFME6 | blood | 1,146,555,396 | 150PE | 385 | 0 | 0 |
| F8241 III-2 | BAFME7 | blood | 1,325,596,586 | 150PE | 818 | 0 | 0 |

BAFME1; benign adult familial myoclonic epilepsy caused by TTTCA pentanucleotide repeat expansion in *SAMD12*,
BAFME6; benign adult familial myoclonic epilepsy caused by TTTCA pentanucleotide repeat expansion in *TNRC6A*,
BAFME7; benign adult familial myoclonic epilepsy caused by TTTCA pentanucleotide repeat expansion in *RAPGEF2*,
hom; homozygous, LCL; lymphoblastoid cell line, PE; paired end

[Fig. 27]

| | BAFME1 | BAFME1 | BAFME6 | BAFME7 | control | control | control | control | control | control | control |
|---|---|---|---|---|---|---|---|---|---|---|---|
| Family | F8135 | F8140 | F9283 | F8241 | 5763_1 | 5764_1 | 4303_2 | 5765_1 | 6071_1 | 5766_1 | 5767_1 |
| Individual | II-1 | V-3 | III-2 | III-2 | | | | | | | |
| Average coverage | 44.1X | 32.8X | 47.7X | 55.0X | 71.0X | 83.1X | 49.2X | 53.1X | 50.8X | 36.9X | 40.5X |
| Repeat motif | | | | | | | | | | | |
| C | 14223 | 19902 | 32241 | 18794 | 58408 | 71353 | 36671 | 33797 | 15309 | 26468 | 20690 |
| AACCCT | 25236 | 32227 | 10564 | 6196 | 23133 | 13819 | 8681 | 7322 | 9092 | 8175 | 7298 |
| A | 2520 | 3922 | 5038 | 3176 | 6072 | 6343 | 5364 | 4161 | 1735 | 3425 | 2812 |
| AAAGG | 124 | 192 | 456 | 158 | 240 | 483 | 211 | 131 | 198 | 143 | 118 |
| AAAG | 160 | 187 | 425 | 330 | 331 | 512 | 203 | 199 | 410 | 218 | 251 |
| AAATG | 323 | 536 | 385 | 818 | 0 | 0 | 0 | 0 | 0 | 0 | 0 |
| AAAAT | 253 | 145 | 285 | 200 | 122 | 247 | 105 | 149 | 26 | 192 | 86 |
| AATGG | 67 | 80 | 142 | 16 | 33 | 115 | 7 | 102 | 189 | 24 | 15 |
| AAG | 108 | 116 | 70 | 142 | 72 | 103 | 220 | 49 | 70 | 71 | 61 |
| AATAG | 35 | 62 | 67 | 6 | 4 | 0 | 29 | 25 | 7 | 35 | 2 |
| AT | 47 | 65 | 47 | 4 | 171 | 358 | 54 | 60 | 21 | 36 | 208 |
| AAAAG | 70 | 14 | 35 | 116 | 124 | 38 | 52 | 11 | 146 | 72 | 78 |
| AGC | 0 | 2 | 8 | 0 | 0 | 4 | 10 | 0 | 9 | 0 | 9 |
| AACAT | 0 | 0 | 18 | 0 | 10 | 0 | 0 | 7 | 0 | 0 | 0 |
| AAAGGATGAGGG | 11 | 9 | 14 | 10 | 24 | 6 | 7 | 14 | 15 | 4 | 6 |
| AG | 5 | 4 | 11 | 2 | 5 | 3 | 2 | 1 | 7 | 5 | 6 |
| AAGAG | 9 | 4 | 9 | 6 | 13 | 12 | 6 | 4 | 3 | 0 | 1 |
| ATCC | 0 | 4 | 4 | 0 | 4 | 10 | 4 | 4 | 2 | 6 | 1 |
| AAACC | 14 | 10 | 2 | 4 | 15 | 4 | 9 | 4 | 2 | 0 | 5 |
| AGCAT | 0 | 7 | 0 | 98 | 11 | 0 | 0 | 0 | 2 | 0 | 57 |
| ACC | 7 | 12 | 2 | 4 | 1 | 1 | 0 | 0 | 1 | 5 | 1 |
| AATATATATATG | 1 | 0 | 1 | 10 | 0 | 0 | 0 | 3 | 0 | 0 | 0 |
| AATAC | 17 | 0 | 0 | 18 | 0 | 0 | 5 | 10 | 20 | 10 | 0 |
| AAGGAG | 30 | 2 | 0 | 0 | 0 | 2 | 1 | 0 | 0 | 2 | 0 |
| AAGAGG | 0 | 0 | 0 | 0 | 0 | 29 | 0 | 0 | 0 | 0 | 0 |
| AAGAC | 0 | 0 | 0 | 0 | 96 | 0 | 0 | 0 | 0 | 0 | 0 |
| AAAGTTCATGGT | 4 | 4 | 0 | 16 | 23 | 0 | 0 | 0 | 0 | 0 | 3 |
| AAACT | 0 | 0 | 0 | 0 | 0 | 0 | 0 | 10 | 0 | 0 | 0 |

The number of reads containing various repeat motifs shown by whole-genome sequence analysis using TRhist.

|  | (TTTCA)>9/(TGAAA)>9 repeat | (TTTTA)>9/(TAAAA)>9 repeat |
|---|---|---|
| In the reference sequence (hg19) | 6 | 711 |
| In the candidate region of BAFME2 on chromosome 2p | 0 | 3 |
| Those located in intron | 0 | 1 |
| In the candidate region of BAFME3 on chromosome 5p | 0 | 2 |
| Those located in intron | 0 | 2 |
| In the candidate region of BAFME4 on chromosome 3q | 0 | 0 |
| Those located in intron | 0 | 0 |

TTTCA/TGAAA or TTTTA/TAAAA repeats in the reference sequence (hg19)

| Repeat motif (in the transcriptional direction) | Gene | Physical position (hg19) | Repeat sequence in the reference sequence in the transcriptional direction |
|---|---|---|---|
| TTTCA | MED12L | chr3:151,086,478-151,086,539 | A(TTTCA)$_{12}$T |
|  | ZDHHC14 | chr6:157,955,566-157,955,632 | A(TTTCA)$_{12}$T |
| TGAAA | GNAQ | chr9:80,263,486-80,263,539 | AAA(TGAAA)$_{10}$T |
| TTTTA | MUSK | chr9:113,463,975-113,464,207 | TTTA(TTTTA)$_{46}$TTT |
| TAAAA | KCNIP4 | chr4:21,716,410-21,716,715 | AAA(TAAAA)$_{60}$TAA |

TTTCA/TGAAA or TTTTA/TAAAA repeats in the reference sequence (hg19)

| Locus | Gene | Physical position (hg19) | Repeat sequence in the reference sequence in the transcriptional direction |
|---|---|---|---|
| BAFME2 candidate region | STARD7 | chr2:96,862,805-96,862,862 | TTTA(TTTTA)$_{10}$TTTT |
| BAFME3 candidate region | MARCH6 | chr5:10,356,456-10,356,523 | TTTA(TTTTA)$_{12}$TTTT |
| BAFME3 candidate region | TRIO | chr5:14,421,337-14,421,394 | TTTA(TTTTA)$_{10}$TTTT |

TTTCA/TGAAA or TTTTA/TAAAA repeats in the reference sequence (hg19)

[Fig. 29]

| Primers | Restriction enzyme | Lengths of the probe | Sequences |
|---|---|---|---|
| SAMD12 (BAFME1) | SacI | | |
| SAMD12-probe-F2 | | 508 bp | 5'-TACAGGGGTTTTTGCCAGAC-3' |
| SAMD12-probe-R3 | | | 5'-CCAACCTCAAATGCATTGACCAC-3' |
| SAMD12-probe-F3 | | 633 bp | 5'-GGATCATTCCTGATAGAAAAAGTCC-3' |
| SAMD12-probe-extremeR | | | 5'-AGCGGCTAATGGTAGATAAGG-3' |
| TNRC6A (BAMFE6) | EcoRI | | |
| TNRC6A-probe-F | | 202 bp | 5'-ATTCACATACCTTTCTGTCTCCC-3' |
| TNRC6A-probe-R2 | | | 5'-GCATTCTACACTGTCTTAGTGA-3' |
| TNRC6A-probe-F2 | | 492 bp | 5'-TCACTAAGACAGTGTAGAATGC-3' |
| TNRC6A-probe-R | | | 5'-TCACAATTCACATTTGGCTTCC-3' |
| RAPGEF2 (BAFME7) | PvuII | | |
| RAPGEF2-long-F1 | | 946 bp | 5'-ACTAGAGGATATTTGCTCAGTCGG-3' |
| RAPGEF2-long-R1 | | | 5'-GGTGATTCTCAGCACATCCTACTATA-3' |
| RAPGEF2-long-F2 | | 904 bp | 5'-TATAGTAGGATGTGCTGAGAATCACC-3' |
| RAPGEF2-long-R2 | | | 5'-TTTAATTGCACAACTTTTCCCTTC-3' |
| RAPGEF2-long-F3 | | 1043 bp | 5'-AACTTTACTCACTGGAATGAGGC-3' |
| RAPGEF2-long-R3 | | | 5'-ACAGCATCCTGGGTAAATCTAATAATC-3' |
| RAPGEF2-long-F4 | | 1264 bp | 5'-TATTGTCCTAAATTGCTTTGCC-3' |
| RAPGEF2-long-R4 | | | 5'-GGAAAGATGAAGTGTAATTTAGCTCC-3' |

Primers used for generation of digoxigenin-labeled probes used in Southern blot hybridization analysis.

[Fig. 30]

| Primer | Direction | Sequence |
|---|---|---|
| centromeric primer | Forward | 5'- CACATCTTGCTAACTAATAGCTGG-3' |
| | Reverse | 5'- CCCAGCCCTCATTTTGTTTATC-3' |
| telomeric primer | Forward | 5'- TGCTGGCTAGAGGAACCATT-3' |
| | Reverse | 5'- TCCTTAAGATTTCCCCCGAC-3' |

Primer sequences used for BAC cloning

[Fig. 31]

| ID | Age at death | Sex | Cause of death |
|---|---|---|---|
| F8135 I-2 (het) | 77 | F | pneumonia |
| F8136 II-5 (het) | 46 | F | ovarian cancer |
| F8135 II-3 (het) | 66 | F | gastric cancer |
| F8138 II-7 (het) | 78 | M | drowning in bathtub |
| F8138 II-5 (het) | 83 | M | myocardial infarction |
| F8140 V-3 (hom) | 71 | F | pneumonia | het, heterozygote; hom, homozygote

The ages at death and the causes of death of autopsied patients

[Fig. 32]

| Transcript | Direction | Location | Sequence |
|---|---|---|---|
| SAMD12 transcript 1 | Forward | Exon 4/5 junction | 5'- CACACAAGCATCATCTGAGGG-3' |
|  | Reverse | Exon 5 | 5'- GCAGTGCCATGGGTTAGTCT-3' |
| RPL13A | Forward | Exon 1 | 5'- AACCTCCTCCTTTTCCAAGC -3' |
|  | Reverse | Exon 2 | 5'- GCAGTACCTGTTTAGCCACGA -3' |
| TNRC6A | Forward | Exon 1a | 5'-GGTGCCCCATCATTTTGCAGC-3' |
|  | Reverse | Exon 3 | 5'-CAACTGTTCTTCTTCTTGCACTAAATCC-3' |

Primer sequences used for RT-PCR

| Gene/Loc | Gene Description | Position (hg19) | Sample 1 | Sample 2 | status | value 1 | value 2 | log2(fold change) | test stat | p value | q value | Significant |
|---|---|---|---|---|---|---|---|---|---|---|---|---|
| - | - | chr13:111642301-111642729 | BAFME | control | OK | 0 | 0.390255 | inf | -nan | 5.00E-05 | 0.018161 | yes |
| LGALS17/ galectin 14 pseudogene | | chr19:40170013-40187109 | BAFME | control | OK | 0 | 0.308938 | inf | -nan | 5.00E-05 | 0.018161 | yes |
| - | - | chr20:26189932-26190044 | BAFME | control | OK | 0 | 2080.02 | inf | -nan | 5.00E-05 | 0.018161 | yes |
| - | - | chr4:9193321-9193479 | BAFME | control | OK | 0 | 7.07996 | inf | -nan | 5.00E-05 | 0.018161 | yes |
| SFN | stratifin | chr1:27189632-27190947 | BAFME | control | OK | 0.084123 | 2.00168 | 4.57257 | 2.96715 | 5.00E-05 | 0.018161 | yes |
| NPAS4 | neuronal PAS domain protein 4 | chr11:66188474-66194177 | BAFME | control | OK | 0.036886 | 0.77142 | 4.38639 | 2.82591 | 0.0001 | 0.031998 | yes |
| GPR64 | G protein-coupled receptor 64 | chrX:19007424-19140755 | BAFME | control | OK | 0.137005 | 1.864 | 3.7661 | 3.09598 | 5.00E-05 | 0.018161 | yes |
| OR7A5 | olfactory receptor, family 7, subfamily A, member 5 | chr19:14937138-14946015 | BAFME | control | OK | 0.081489 | 0.623599 | 2.93594 | 2.10925 | 5.00E-05 | 0.018161 | yes |
| CCL2 | chemokine (C-C motif) ligand 2 | chr17:32582295-32584220 | BAFME | control | OK | 1.95106 | 11.3437 | 2.53956 | 2.18362 | 5.00E-05 | 0.018161 | yes |
| ELK2AP | ELK2A, member of ETS oncogene family, pseudogene | chr14:1061099413-106331637 | BAFME | control | OK | 1.05236 | 4.71074 | 2.16232 | 2.03282 | 0.00015 | 0.046341 | yes |
| NMUR2 | neuromedin U receptor 2 | chr5:151745383-152109359 | BAFME | control | OK | 1.00849 | 4.15608 | 2.04302 | 2.36883 | 5.00E-05 | 0.018161 | yes |
| LRP2 | low density lipoprotein receptor-related protein 2 | chr2:169983618-170219122 | BAFME | control | OK | 0.627602 | 2.53268 | 2.01274 | 3.45597 | 5.00E-05 | 0.018161 | yes |
| ANKRD26 | ankyrin repeat domain 26 pseudogene 3 | chr13:19830441-19919174 | BAFME | control | OK | 0.188675 | 0.640105 | 1.7624 | 1.91967 | 5.00E-05 | 0.018161 | yes |
| GBP1 | guanylate binding protein 1, interferon-inducible | chr1:89517986-89531506 | BAFME | control | OK | 1.32778 | 4.24668 | 1.67731 | 2.12172 | 5.00E-05 | 0.018161 | yes |
| TNC | tenascin C | chr3:170556179-170577418 | BAFME | control | OK | 0.130931 | 0.403741 | 1.62462 | 2.19974 | 5.00E-05 | 0.018161 | yes |
| SERPINA | serpin peptidase inhibitor, clade A (alpha-1 antiproteinase, antitry | chr14:95078713-95090691 | BAFME | control | OK | 0.567099 | 1.68318 | 1.56951 | 2.22769 | 5.00E-05 | 0.018161 | yes |
| - | - | chr4:1591199565-1592007847 | BAFME | control | OK | 12.2672 | 34.5214 | 1.49269 | 2.38016 | 5.00E-05 | 0.018161 | yes |
| C11orf9 | myelin regulatory factor | chr11:61520097-61556425 | BAFME | control | OK | 0.375012 | 0.974821 | 1.3782 | 1.84902 | 5.00E-05 | 0.018161 | yes |
| PIEZO2 | piezo-type mechanosensitive ion channel component 2 | chr18:10669855-11149557 | BAFME | control | OK | 3.58711 | 9.09718 | 1.3426 | 2.56142 | 5.00E-05 | 0.018161 | yes |
| - | - | chr2:79547191-79565140 | BAFME | control | OK | 0.72041 | 1.74725 | 1.2782 | 2.00168 | 5.00E-05 | 0.018161 | yes |
| - | - | chr3:17042816469-170473277 | BAFME | control | OK | 0.286251 | 0.683593 | 1.25586 | 1.85894 | 5.00E-05 | 0.018161 | yes |
| - | - | chr2:79609911-79635925 | BAFME | control | OK | 0.415089 | 0.971278 | 1.22646 | 1.95422 | 0.0001 | 0.031998 | yes |
| - | - | chr2:113376046-1134122219 | BAFME | control | OK | 0.360322 | 0.839664 | 1.22052 | 2.03256 | 5.00E-05 | 0.018161 | yes |
| OAS3 | 2'-5'-oligoadenylate synthetase 3, 100kDa | chr1:44870959-45118792 | BAFME | control | OK | 1.16744 | 2.64493 | 1.17988 | 1.83861 | 5.00E-05 | 0.018161 | yes |
| RNF220 | ring finger protein 220 | chr2:79637990-79863950 | BAFME | control | OK | 1.07383 | 2.42282 | 1.17392 | 1.81124 | 5.00E-05 | 0.018161 | yes |
| - | - | chr12:214156048-21548371 | BAFME | control | OK | 0.34316 | 0.749795 | 1.12761 | 1.88127 | 5.00E-05 | 0.018161 | yes |
| SLCO1A2 | solute carrier organic anion transporter family, member 1A2 | chr2:79672003-79719330 | BAFME | control | OK | 3.38159 | 7.36204 | 1.1224 | 2.20882 | 5.00E-05 | 0.018161 | yes |
| - | - | chr10:128106789-128358946 | BAFME | control | OK | 0.314885 | 0.680482 | 1.11173 | 1.99722 | 5.00E-05 | 0.018161 | yes |
| - | - | - | BAFME | control | OK | 0.651499 | 1.39632 | 1.0998 | 1.81687 | 5.00E-05 | 0.018161 | yes |

RNA-seq analysis of four heterozygous BAFME patients with repeat expansion mutations in SAMD12 and eight control subjects.
All the data are calculated by Cufflinks, Cuffquant, and Cuffdiff (v2.2.1) with default settings (Trapnell, C. et al. Nat. Biotechnol. 28, 511–515 (2010)).

Fig. 33a

| Gene/Loc | Gene Description | Position (hg19) | Sample 1 | Sample 2 | status | value 1 | value 2 | log2(fold change) | test stat | p value | q value | Significant |
|---|---|---|---|---|---|---|---|---|---|---|---|---|
| F3 | coagulation factor III | chr1:94994731-95007413 | BAFME | control | OK | 20.9299 | 44.0299 | 1.07292 | 2.04463 | 5.00E-05 | 0.018161 | yes |
| MOBP | myelin-associated oligodendrocyte basic protein | chr3:39508627-39575896 | BAFME | control | OK | 21.6162 | 42.2417 | 0.966555 | 1.72173 | 5.00E-05 | 0.018161 | yes |
| TMEM144 | transmembrane protein 144 | chr4:159131400-159178053 | BAFME | control | OK | 19.9612 | 38.8116 | 0.95929 | 2.0033 | 5.00E-05 | 0.018161 | yes |
| SLC7A2 | solute carrier family 7 (cationic amino acid transporter, y+ system | chr8:17351840-17428077 | BAFME | control | OK | 4.72201 | 9.17956 | 0.959024 | 1.86645 | 5.00E-05 | 0.018161 | yes |
| HHIP | hedgehog interacting protein | chr4:145564067-145664013 | BAFME | control | OK | 4.29239 | 8.29859 | 0.951085 | 1.82357 | 5.00E-05 | 0.018161 | yes |
| ENPP2 | ectonucleotide pyrophosphatase/phosphodiesterase 2 | chr8:120569288-120686055 | BAFME | control | OK | 12.4296 | 24.0244 | 0.950713 | 1.95368 | 5.00E-05 | 0.018161 | yes |
| GPR37 | G protein-coupled receptor 37 | chr7:124382161-124406149 | BAFME | control | OK | 7.12064 | 13.5822 | 0.931641 | 1.70479 | 5.00E-05 | 0.018161 | yes |
| MOG | myelin oligodendrocyte glycoprotein | chr6:29624757-29640149 | BAFME | control | OK | 10.4586 | 19.876 | 0.926343 | 1.70701 | 0.0001 | 0.031998 | yes |
| SCD | stearoyl-CoA desaturase (delta-9-desaturase) | chr10:102106251-102124588 | BAFME | control | OK | 46.0848 | 84.563 | 0.875733 | 2.06047 | 5.00E-05 | 0.018161 | yes |
| TF | transferrin | chr3:133418893-133497856 | BAFME | control | OK | 29.7912 | 50.3276 | 0.758465 | 1.88265 | 0.0001 | 0.031998 | yes |
| PLP1 | proteolipid protein 1 | chrX:103031438-103047547 | BAFME | control | OK | 228.017 | 365.369 | 0.680212 | 1.64017 | 0.0001 | 0.031998 | yes |
| RPS4X | ribosomal protein S4, X-linked | chrX:71492452-71497141 | BAFME | control | OK | 182.656 | 111.321 | -0.714404 | -1.66431 | 5.00E-05 | 0.018161 | yes |
| B3GNT1 | UDP-GlcNAc:betaGal beta-1,3-N-acetylglucosaminyltransferase | chr11:66112842-66115161 | BAFME | control | OK | 61.2205 | 36.0685 | -0.763276 | -1.71216 | 0.0001 | 0.031998 | yes |
| OAZ1 | ornithine decarboxylase antizyme 1 | chr19:2269519-2273487 | BAFME | control | OK | 165.818 | 97.6238 | -0.764298 | -1.77825 | 0.0001 | 0.031998 | yes |
| RPS12 | ribosomal protein S12 | chr6:133135707-133138703 | BAFME | control | OK | 190.923 | 106.714 | -0.839241 | -1.7138 | 0.0001 | 0.031998 | yes |
| ICAM5 | intercellular adhesion molecule 5, telencephalin | chr19:10400116-10407454 | BAFME | control | OK | 16.8524 | 9.0632 | -0.894367 | -1.84081 | 5.00E-05 | 0.018161 | yes |
| APOE | apolipoprotein E | chr19:45409038-45412650 | BAFME | control | OK | 165.438 | 88.2652 | -0.906373 | -2.09126 | 5.00E-05 | 0.018161 | yes |
| RPPH1 | ribonuclease P RNA component H1 | chr14:20811229-20811570 | BAFME | control | OK | 28549 | 15212.8 | -0.908151 | -1.9332 | 0.00015 | 0.046341 | yes |
| RPS9 | ribosomal protein S9 | chr19:54704725-54711515 | BAFME | control | OK | 97.1966 | 50.905 | -0.9331 | -1.93793 | 5.00E-05 | 0.018161 | yes |
| HIST1H4C | histone cluster 1, H4c | chr6:26104175-26104565 | BAFME | control | OK | 132.332 | 68.7923 | -0.943839 | -1.69114 | 5.00E-05 | 0.018161 | yes |
| C3 | complement component 3 | chr19:6677845-6720662 | BAFME | control | OK | 22.9689 | 11.6495 | -0.979408 | -2.0045 | 5.00E-05 | 0.018161 | yes |
| HIST1H1E | histone cluster 1, H1d | chr6:26234439-26235216 | BAFME | control | OK | 18.3209 | 8.4545 | -1.1157 | -1.72142 | 0.0001 | 0.031998 | yes |
| CD74 | CD74 molecule, major histocompatibility complex, class II invariar | chr5:149781199-149792499 | BAFME | control | OK | 93.9471 | 42.7849 | -1.13475 | -2.32388 | 5.00E-05 | 0.018161 | yes |
| DNAJB1 | DnaJ (Hsp40) homolog, subfamily B, member 1 | chr19:14625578-14640073 | BAFME | control | OK | 38.1622 | 17.3191 | -1.13978 | -2.20488 | 5.00E-05 | 0.018161 | yes |
| CTSZ | cathepsin Z | chr20:57570241-57582309 | BAFME | control | OK | 24.4723 | 10.9789 | -1.15641 | -2.14078 | 5.00E-05 | 0.018161 | yes |
| C1QB | complement component 1, q subcomponent, B chain | chr1:22879881-22982058 | BAFME | control | OK | 45.5027 | 19.8907 | -1.19386 | -2.06086 | 5.00E-05 | 0.018161 | yes |
| LAMP5 | lysosomal-associated membrane protein family, member 5 | chr20:9490803-9511171 | BAFME | control | OK | 44.2278 | 19.0315 | -1.21656 | -2.29744 | 5.00E-05 | 0.018161 | yes |
| MS4A14 | membrane-spanning 4-domains, subfamily A, member 14/7 | chr11:60131288-60185228 | BAFME | control | OK | 5.58476 | 2.19726 | -1.3458 | -1.86746 | 0.0001 | 0.031998 | yes |
| C7 | complement component 7 | chr5:40909598-41071444 | BAFME | control | OK | 5.82797 | 2.12195 | -1.40722 | -2.07308 | 5.00E-05 | 0.018161 | yes |
| - | - | chr4:139364169-139381126 | BAFME | control | OK | 0.439317 | 0.164185 | -1.41994 | -1.76226 | 5.00E-05 | 0.018161 | yes |

RNA-seq analysis of four heterozygous BAFME patients with repeat expansion mutations in SAMD12 and eight control subjects.
All the data are calculated by Cufflinks, Cuffquant, and Cuffdiff (v2.2.1) with default settings (Trapnell, G. et al. Nat Biotechnol. 28, 511-515 (2010)).

*Fig. 33b*

| Gene/Loc | Gene Description | Position (hg19) | Sample 1 | Sample 2 | status | value 1 | value 2 | log2(fold change) | test stat | p value | q value | Significant |
|---|---|---|---|---|---|---|---|---|---|---|---|---|
| RNF149 | ring finger protein 149 | chr2:101869230-101925178 | BAFME | control | OK | 26.7791 | 9.77176 | -1.45442 | -2.83649 | 5.00E-05 | 0.018161 | yes |
| HLA-DMA | major histocompatibility complex, class II, DM alpha/beta | chr6:32902355-32921316 | BAFME | control | OK | 14.4437 | 5.07838 | -1.508 | -1.99711 | 5.00E-05 | 0.018161 | yes |
| CD14 | CD14 molecule | chr5:140002077-140013286 | BAFME | control | OK | 16.5315 | 5.63662 | -1.55231 | -2.28423 | 5.00E-05 | 0.018161 | yes |
| MS4A6A | membrane-spanning 4-domains, subfamily A, member 6A | chr11:59939079-59952139 | BAFME | control | OK | 8.39182 | 2.77194 | -1.59809 | -2.05646 | 5.00E-05 | 0.018161 | yes |
| C1QA | complement component 1, q subcomponent, A chain | chr1:22963111-22966175 | BAFME | control | OK | 22.1325 | 7.26228 | -1.60668 | -2.36855 | 5.00E-05 | 0.018161 | yes |
| TMEM215 | transmembrane protein 215 | chr9:32783496-32789199 | BAFME | control | OK | 1.43419 | 0.466438 | -1.62048 | -2.1487 | 5.00E-05 | 0.018161 | yes |
| FCGBP | Fc fragment of IgG binding protein | chr19:40353962-40456745 | BAFME | control | OK | 4.99424 | 1.60061 | -1.64165 | -3.00876 | 5.00E-05 | 0.018161 | yes |
| HLA-DRA | major histocompatibility complex, class II, DR alpha | chr6:32407618-32412826 | BAFME | control | OK | 64.0134 | 19.8974 | -1.6858 | -2.81458 | 5.00E-05 | 0.018161 | yes |
| WDR74 | WD repeat domain 74 | chr11:62600381-62609282 | BAFME | control | OK | 1359.33 | 420.875 | -1.69143 | -3.27218 | 5.00E-05 | 0.018161 | yes |
| HIST1H4F | histone cluster 1, H4f | chr6:26240653-26241021 | BAFME | control | OK | 26.8394 | 7.75657 | -1.79086 | -2.16742 | 5.00E-05 | 0.018161 | yes |
| HSPA1B | heat shock 70kDa protein 1B | chr6:31795511-31798031 | BAFME | control | OK | 59.6176 | 16.4792 | -1.85509 | -3.61975 | 5.00E-05 | 0.018161 | yes |
| MARCO | macrophage receptor with collagenous structure | chr2:119699744-119752236 | BAFME | control | OK | 1.98989 | 0.521805 | -1.91653 | -1.92767 | 0.00015 | 0.046341 | yes |
| GPNMB | glycoprotein (transmembrane) nmb | chr7:23286315-23314729 | BAFME | control | OK | 17.9397 | 4.68339 | -1.93753 | -2.95125 | 5.00E-05 | 0.018161 | yes |
| HSPA1A | heat shock 70kDa protein 1A | chr6:31783290-31791393 | BAFME | control | OK | 50.1338 | 13.0402 | -1.94281 | -3.76655 | 5.00E-05 | 0.018161 | yes |
| - | - | chr16:66453448-66460074 | BAFME | control | OK | 0.436284 | 0.110963 | -1.97518 | -2.10772 | 5.00E-05 | 0.018161 | yes |
| - | - | chr4:139405629-139412035 | BAFME | control | OK | 0.535437 | 0.128798 | -2.05561 | -2.10628 | 5.00E-05 | 0.018161 | yes |
| - | - | chr4:139412254-139417574 | BAFME | control | OK | 0.542382 | 0.12162 | -2.15693 | -2.06393 | 5.00E-05 | 0.018161 | yes |
| CCL5 | chemokine (C-C motif) ligand 5 | chr17:34198495-34207377 | BAFME | control | OK | 1.7822 | 0.393508 | -2.16096 | -1.92515 | 5.00E-05 | 0.018161 | yes |
| ST14 | suppression of tumorigenicity 14 (colon carcinoma) | chr11:130029691-130060257 | BAFME | control | OK | 0.777304 | 0.173561 | -2.16303 | -2.06502 | 5.00E-05 | 0.018161 | yes |
| FCGR2B | Fc fragment of IgG, low affinity IIb, receptor (CD32) | chr1:161632904-161646444 | BAFME | control | OK | 2.05437 | 0.4114 | -2.32006 | -2.13277 | 5.00E-05 | 0.018161 | yes |
| APOC1 | apolipoprotein C-I | chr19:45417284-45422606 | BAFME | control | OK | 20.8802 | 4.02133 | -2.37708 | -2.79462 | 5.00E-05 | 0.018161 | yes |
| LYZ | lysozyme | chr12:69742133-69748190 | BAFME | control | OK | 13.4836 | 1.39651 | -3.27131 | -3.47289 | 5.00E-05 | 0.018161 | yes |
| - | - | chr4:139189190-139213895 | BAFME | control | OK | 1.13783 | 0.111985 | -3.3449 | -2.73583 | 5.00E-05 | 0.018161 | yes |
| ACP5 | acid phosphatase 5, tartrate resistant | chr19:11685349-11689801 | BAFME | control | OK | 2.47519 | 0.215914 | -3.51901 | -3.08293 | 5.00E-05 | 0.018161 | yes |
| - | - | chr4:139181739-139187612 | BAFME | control | OK | 0.403558 | 0.031074 | -3.699 | -3.01706 | 5.00E-05 | 0.018161 | yes |
| - | - | chr17:4299949-4300673 | BAFME | control | OK | 0.403697 | 0 | -inf | -nan | | | |
| - | - | chr2:87410452-87411189 | BAFME | control | OK | 0.586928 | 0 | -inf | -nan | 5.00E-05 | 0.018161 | yes |
| - | - | chr2:87447668-87448254 | BAFME | control | OK | 0.728204 | 0 | -inf | -nan | 5.00E-05 | 0.018161 | yes |

RNA-seq analysis of four heterozygous BAFME patients with repeat expansion mutations in SAMD12 and eight control subjects.
All the data are calculated by Cufflinks, Cuffquant, and Cuffdiff (v2.2.1) with default settings (Trapnell, C. et al. Nat. Biotechnol. 28, 511-515 (2010)).

*Fig. 33c*

```
                         SEQUENCE LISTING

<160> NUMBER OF SEQ ID NOS: 135

<210> SEQ ID NO 1
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Repeat probe

<400> SEQUENCE: 1
tgaaatgaaa tgaaatgaaa tgaaatgaaa tgaaatgaaa tgaaa              45

<210> SEQ ID NO 2
<211> LENGTH: 508
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Probe 1a

<400> SEQUENCE: 2
tacaggggtt tttgccagac accgagaatt ggtggtcccc ccaaaaaagg ccacagagaa    60
attagttaat atgcaatatt agggacagaa gtcctaaagc acacagatgg catattttc   120 tgtttcttct tagaaaagcc agaacatctc agtgcatctc tgaaagtggc tttgatttct   180
tcttatccag tccacatgtc aatgttctaa atcaactgac tctctaaaaa tcccatagga   240
catttgaaca ccgcacatat tagactgtag ggtctatact tatcctcaag aataaaacca   300
atatcaattg ttgaaaacct gtaactcatc tttcttcaat gtaacattag taatttaaga   360
tccttcaaat ccacagtcaa gccacaaggt caaggtgaca taacaatgca accttatgac   420
catcttaaat tgtccaaaca agagatatca catatattgt ttcacctagt acatttaaat   480
gcaaagtggt caatgcattt gaggttgg                                     508

<210> SEQ ID NO 3
<211> LENGTH: 633
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Probe 1b

<400> SEQUENCE: 3
ggatcattcc tgatagaaaa agtccatatt agacaaataa tgtgtagaca tgtctcccat    60
```

```
atgctggcta gaggaaccat tagggycgct acaaaaggca gatattttc taccatgaac    120 aatgtaacag acaagaatca tgagtccatg tcaagcctta aacaaaactc cttcttggat    180
taaatgacct aatggattcc cagaataaaa acgaaacagg aaaagatgct aatcaggata    240
tacatctcat aattctaact gctactgata aactgacata tgattttaat aattccctca    300
aaaaacatgt cttttggcct ttaaatataa agctcattcc aaggagaatt tctctgatgg    360
cttaaagact tgataaaatt agaaatattc ctggccacaa catttctgca agggtgcgaa    420
gattttgaaa tgtgtcgggg gaaatcttaa ggaggtagca gttcgagaaa atgtggactt    480
ggaggaaatt gagaagggac acgtgattcg cagatcataa tcaaataagg ttgaatgaag    540
aagtagtaac aaaagaccct agctacagaa gaataatctg ttcagattcc tattaggtta    600
ctcatccaaa atccttatct accattagcc gct                                633
```

```
<210> SEQ ID NO 4
<211> LENGTH: 202
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Probe 6a

<400> SEQUENCE: 4
```

```
attcacatac ctttctgtct cccactgatt tttcttagga gttcctctca tcctctaacc    60
tcgcttttta aaattatttt tctggatacc tagattttg tcctttctgg ccagagcctg     120
aaagaacagc ttctaaggac ttggtgattg gaaatgtacc ttctaaaaaa aattcttttt    180
tcactaagac agtgtagaat gc                                            202
```

```
<210> SEQ ID NO 5
<211> LENGTH: 492
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Probe 6b

<400> SEQUENCE: 5
```

```
tcactaagac agtgtagaat gcccagttcc cgctgtgtgt acgtgcgtgc acatatgtgt    60
taaaggagat ggatacattg cttggggcca tcagaactgt ttcctgggag gtggtttctt    120
ggctccacac cccagctcag caagggaatg atcaagtgat aggaggcaca gttacagcag    180
tcaggagaca aggcactcgg accccaaacg tctgactctc tgtgggagaa accagggctc    240
aaagcaggag caaaaaatct agtgctggat gcgctcgggc atcgagaggc atctcgtaga    300
gctggctccg agtttgaggc cacacctttg cagaatgagg cagcatgtga gcgatttagt    360
tcaatgtaat tgcagtggag atggacaggg agaggacaga ttagaatgat gtttaaggga    420
tagaaataac aagtcttgca gatatattac atatattagt tgaaccatgg ggaagccaaa    480
tgtgaattgt ga                                                       492
```

```
<210> SEQ ID NO 6
<211> LENGTH: 926
<212> TYPE: DNA
<213> ORGANISM: Artificial Sequence
```

<220> FEATURE:
<223> OTHER INFORMATION: Description of Artificial Sequence: Synthetic
      polynucleotide
<220> FEATURE:
<223> OTHER INFORMATION: Probe 7a

<400> SEQUENCE: 6

```
actagaggat atttgctcag tcggttttat caaatggccg ctatgggcta agcactgcta     60
tgtgtacata ctgctgtgta tggaaacaaa gcatcaatac ttacattcag gtggttttac    120
tgatagtaaa cagatgaggt aggtctatac ggaagagaag agtaaaacgc cttggcttga    180
ccctgaccct acttccctgt gccatctcat tccccagaat tatcatgaac agtttcttat    240
gcagccttct gtaaattgtt atgcatataa agcataaaca tagagatgtt atatgtcaat    300
aaataatctg tacactattt tactttagtt gttataccat gtttcttttt ctcctctcag    360
tggcctaaac ctggcaccag tggcaagact gcgaacgacc tgggagaaac ttcccaataa    420
atacgaaaaa ctatttcaag atctccaaga cctgtttgat ccttccagaa acatggcaaa    480
atatcgtaat gttctcaata gtcaaaatct acaacctccc ataatccctc tattcccagt    540
tatcaaaaag gatctcacct tccttcacga aggtaaacat aaggcagagg gtttccatct    600
ttgcttgaag aagcacagaa taaatgccat gtgatttcct tttcctcctc tgtcaatttc    660
aggaaatgac tcaaaagtag acgggctggt caattttgag aagctaagga tgattgcaaa    720
agaaattcgt cacgttggcc gaatggcttc agtgaacatg gaccctgccc tcatgttcag    780
gactcggtga gtatgtcatc ttcagtggca cgtgtgagag tagagaaggt taaatttaga    840
gcttcccaat aaatgatttt tttaaagttt gagtatttat atttgtagta cggcagaaat    900
tatagtagga tgtgctgaga atcacc                                         926
```

<210> SEQ ID NO 7
<211> LENGTH: 904
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Probe 7b

<400> SEQUENCE: 7

```
tatagtagga tgtgctgaga atcacctgtg agctctaatt tggaataaat gtcttattct     60
gtataaagtg ttctttcggc tgtcagtaaa aacagtttgt ctttcagaca ttttcaatgt    120
aatagacaca attatgtgtt tcttatttct cagaacactg acttgtagag ctaaaactca    180
tagctagtag tatgcactaa aatatgtaaa taccccaaat agtcttgtct caatatccac    240
acaacaaatt tagctagcag tgtagtaaaa agtgattaat tcagtgaaag agagaaaagt    300
cagtcttaat tctagaacaa aaaatttaaa tgtatgtgtc ttttaagcca gaaaaatatt    360
tctagtaaag ttgcgtgtgt gaggtgatta tgcagtttaa tgtttgtggg cttctagaac    420
tgcttatcca gaagtctagt cctttctttc tgagcttgtg atctttctgt ctctctttct    480
acacccatgc ttcaatctcc atggctctca cttacaggaa gaagaaatgg cggagtttgg    540
ggtaagtggt ggagaccttg catacccaca cacagttctt attctgctca ttgcattgtt    600
ttcttacctg ctgtattttc tgatgctttg cattttgca ttttttttcct taaccctcgt    660
gctgtagcag aatttcagat ggcaaattga cttcaagttt aatctgttgg ggcttttgct    720
tttgaagtca tgatccatga gagctgtgaa atgattgatg attgttctgg ggaactacag    780
```

```
gccagttttt ctgagctctt agaaaaattt tattttcata taattggtgt gtctcgaaat    840
gcagaaagct caaagtaggg ggaggggagg aaggatatta gaagggaaaa gttgtgcaat    900
taaa                                                                 904
```

```
<210> SEQ ID NO 8
<211> LENGTH: 1043
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Probe 7c

<400> SEQUENCE: 8
cagtttactc actggaatga ggcatgtgac cttttgaaca tagactatta atatcagtct     60
tggcacattt taaatagata aagtactccc atgctagagt gagctgcata tgtacctttt    120
catcttccag gtctctcagc cagggtagta caaatgcaac agtgctagat gttgctcaga    180
caggtggtca taaaaagcgg gtacgtcgta gttcctttct caatgccaaa aagctttatg    240
aagatgccca atggctcga aaagtgaagc agtacctttc caatttggag ctagaaatgg     300
acgaggagag tcttcagaca ttatctctgc agtgtgagcc agcaaccaac acatgtgagt    360
ttttccttaa agtggctgca gactttggct aggatgcaga tttgtttcct gtgcagtggt    420
atgggcagtg acaaaataag gcttagtgca gaggggagc tagcaatcct gagatatact     480
agtcttttcc ttgaatgcta atatttaata ctgggtagca ctgtgcacgg ccaggccgtc    540
atgtcaactg ggttagtatg tggaagatga cactgtccac atctaaggca acccattact    600
ttagtttcac ctggacacaa ccagtacaca tgcaacagac gcatatatag atatggctcc    660
catttacatg tcttacgttc tcacaaagct accccaaag tatgggcaac ctgaggggag     720
tcagggcata aaattgggtg tgctggctgc cttttaacca ctagcccaga caacaccgaa    780
caacaaattc agctaccagt tagttagagc aatgattctg ctccacagtg aaccacaata    840
gcctttaaaa atctggttaa tctataaatg gggcagtttt ttttttttc taaatctgca     900 tcttgactta aaagacaaag gcattttcca ttcagtacac acctgtgtct tttatgggca    960
ggtttgaaga tgtcttctgt aggatttaat ttagataggt gatttgagaa gatttggatt   1020
attagattta cccaggatgc tgt                                           1043
```

```
<210> SEQ ID NO 9
<211> LENGTH: 1264
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Probe 7d

<400> SEQUENCE: 9
tattgtccta aattgctttg ccatttatct accacaaaat atatactcag tatgatactg     60
aagcattatt ggctactgtt tgcttgcata gataattcta cctcctagga atatggtagt    120
aaatagattg cagttgacag catttattaa ataaaaactt agcacataca tgtcaaacaa    180
tttgggacac cgtttagaa aaatagtgcc tgatgacttt tctgttgtag cttttatcac     240
gtatttgttt cttcatata catggatata acatattgaa ctaccacat ttttctatat      300 ttttaatggg gtgtttaata gtacaatcat cttttgagat tgctgacttc ataaagtaga    360
```

```
tacctttgtc ctgccacata tctaatattt tctgtaacta gggtccccca tccattttct    420
gtgcttcata aaggcaacag gaagaaaggt gtgcattaat ttagtattct aactgcagaa    480
aatgctcaca cagttctaga attatcttct acatacctac tagcatctaa aattctttgt    540
tctattttca aacccaaaca attatcagtg cctaagaatc ctggtgacaa aaagcctgtc    600
aaatccgaga cctctccagt agctccaagg gcagggtcac aacagaaagc tcagtccctg    660
ccacagcccc agcagcagcc accaccagca cataaaatca accagggact acaggttccc    720
gccgtgtccc tttatccttc acggaagaaa gtgcccgtaa aggatctccc accttttggt    780
aagtgattac attcatttct ttttttggtg ccattcactg tcatggtttg caaattagga    840
aaaaaatatt tgtcttggat aactttgtct aatatatttg agtttctctg taattattag    900
ctcctaataa aacatgaaca ctcagcaagt taaacctgac tttgccaatg aagggggttg    960
tttttataag taatatctcg tttagtcatg ctaatttgct acgacagggt gttaatagag   1020 aagtatgtg tctattaatt taattttgc taagcgcaga agatgctttg ttcatttaca     1080
ttatttaaac tggttttgct ttacaaccaa caaactgctg ggatttaagc agaatatttt   1140
taagttaaat gaattgtctg aaggtaaatt cttatttgtt gactcactga ttctataact   1200
tagagggaaa aataaaacaa ctaactcctg aatatgaagg agctaaatta cacttcatct   1260
ttcc                                                                1264

<210> SEQ ID NO 10
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: SITE
<222> LOCATION: (39)..(123)
<223> OTHER INFORMATION: This sequence may encompass 11 or 17 "tttta"
      repeating units

<400> SEQUENCE: 10
ttttatttta ttttatttta ttttatttta ttttattatt ttatttatt ttatttatt     60 ttattttatt ttattttatt ttattttatt ttattttatt ttattttatt ttattttatt   120
tta                                                                 123

<210> SEQ ID NO 11
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
ttttatttta ttttatttta ttttatttta ttttattatt ttatttatt ttatttatt     60 ttattttatt ttattttatt ttattttatt ttattttatt tta                     103

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 12
tgaaatgaaa tgaaatgaaa tgaaatgaaa tgaaatgaaa tgaaa                45

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tgaaatgaaa tgaaatgaaa tgaaatgaaa tgaaatgaaa tgaaatgaaa tgaaatgaaa     60

<210> SEQ ID NO 14
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tttcatttca tttcatttca tttcatttca tttcatttca tttcatttca tttcatttca     60

<210> SEQ ID NO 15
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
taaaataaaa taaaataaaa taaaataaaa taaaataaaa taaaataaaa taaaataaaa     60

<210> SEQ ID NO 16
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
taaaataaaa taaaataaaa taaaataaaa taaaataaaa taaaataaaa taaaataaaa     60
taaaataaaa taaaataaaa taaaataaaa                                     90

<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tgaaatgaaa tgaaatgaaa tgaaatgaaa tgaaatgaaa tgaaa                45

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 18
tgaaatgaaa tgaaatgaaa tgaaatgaaa tgaaatgaaa tgaaatgaaa tgaaatgaaa    60

<210> SEQ ID NO 19
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ttttatttta ttttatttta ttttatttta ttttatttta ttttatttta ttttatttta    60
ttttatttta ttttatttta ttttatttta                                     90

<210> SEQ ID NO 20
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ttttatttta ttttatttta ttttatatta ttttatttta ttttatttta ttttatttta    60
ttttatttta ttttatttta ttttatttta                                     90

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu His Phe Thr Ser
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Gln Phe Ser Ser
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Phe Tyr Phe Ile Leu
1               5

<210> SEQ ID NO 24

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Phe His Phe Ile Ser
1               5

<210> SEQ ID NO 25
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tttcatttca tttcatttca tttcatttca tttcatttca tttcatttca tttcatttca      60

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
taaaataaaa taaaataaaa taaaataaaa taaaataaaa taaaataaaa taaaataaaa      60

<210> SEQ ID NO 27
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
taaaataaaa taaaataaaa taaaataaaa taaaataaaa taaaataaaa taaaataaaa      60
taaaataaaa taaaataaaa taaaataaaa                                      90

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: See specification as filed for detailed
      description of substitutions and preferred embodiments

<400> SEQUENCE: 28
ttttatttca                                                            10

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<220> FEATURE:
<223> OTHER INFORMATION: See specification as filed for detailed
      description of substitutions and preferred embodiments

<400> SEQUENCE: 29
ttttatttca tttta                                                      15

<210> SEQ ID NO 30
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: See specification as filed for detailed
      description of substitutions and preferred embodiments

<400> SEQUENCE: 30
ttttatttta ttttatttta ttttatttta ttttatttta ttttatttta ttttatttta      60
ttttatttta ttttatttta ttttatttta ttttatttta ttttatttta tttcatttta     120

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: See specification as filed for detailed
      description of substitutions and preferred embodiments

<400> SEQUENCE: 31
ttttatttca tttta                                                      15

<210> SEQ ID NO 32
<211> LENGTH: 5280
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
ttttatttta ttttatttta ttttatttta ttttatttta ttttatttta ttttatttta      60
ttttatttta ttttatttta ttttatttta ttttatttta ttttatttta ttttatttta     120
ttttatttta ttttatttta ttttatttta ttttatttta ttttatttta ttttatttta     180
ttttatttta ttttatttta ttttatttta ttttatttta ttttatttta ttttatttta     240
ttttatttta ttttatttta ttttatttta ttttatttta ttttatttta ttttatttta     300
ttttatttta ttttatttta ttttatttta ttttatttta ttttatttta ttttatttta     360
ttttatttta ttttatttta ttttatttta ttttatttta ttttatttta ttttatttta     420
ttttatttta ttttatttta ttttatttta ttttatttta ttttatttta ttttatttta     480
ttttatttta ttttatttta ttttatttta ttttatttta ttttatttta ttttatttta     540
ttttatttta ttttatttta ttttatttta ttttatttta ttttatttta ttttatttta     600
ttttatttta ttttatttta ttttatttta ttttatttta ttttatttta ttttatttta     660
ttttatttta ttttatttta ttttatttta ttttatttta ttttatttta ttttatttta     720
ttttatttta ttttatttta ttttatttta ttttatttta ttttatttta ttttatttta     780
```

| | |
|---|---|
| ttttatttta ttttatttta ttttatttta ttttatttta ttttatttta ttttatttta | 840 |
| ttttatttta ttttatttta ttttatttta ttttatttta ttttatttta ttttatttta | 900 |
| ttttatttta ttttatttta ttttatttta ttttatttta ttttatttta ttttatttta | 960 |
| ttttatttta ttttatttta ttttatttta ttttatttta ttttatttta ttttatttta | 1020 |
| ttttatttta ttttatttta ttttatttta ttttatttta ttttatttta ttttatttta | 1080 |
| ttttatttta ttttatttta ttttatttta ttttatttta ttttatttta ttttatttta | 1140 |
| ttttatttta ttttatttta ttttatttta ttttatttta ttttatttta ttttatttta | 1200 |
| ttttatttta ttttatttta ttttatttta ttttatttta ttttatttta ttttatttta | 1260 |
| ttttatttta ttttatttta ttttatttta ttttatttta ttttatttta ttttatttta | 1320 |
| ttttatttta ttttatttta ttttatttta ttttatttta ttttatttta ttttatttta | 1380 |
| ttttatttta ttttatttta ttttatttta ttttatttta ttttatttta ttttatttta | 1440 |
| ttttatttta ttttatttta ttttatttta ttttatttta ttttatttta ttttatttta | 1500 |
| ttttatttta ttttatttta ttttatttta ttttatttta ttttatttta ttttatttta | 1560 |
| ttttatttta ttttatttta ttttatttta ttttatttta ttttatttta ttttatttta | 1620 |
| ttttatttta ttttatttta ttttatttta ttttatttta ttttatttta ttttatttta | 1680 |
| ttttatttta ttttatttta ttttatttta ttttatttta ttttatttta ttttatttta | 1740 |
| ttttatttta ttttatttta ttttatttta ttttatttta ttttatttta ttttatttta | 1800 |
| ttttatttta ttttatttta ttttatttta ttttatttta ttttatttta ttttatttta | 1860 |
| ttttatttta ttttatttta ttttatttta ttttatttta ttttatttta ttttatttta | 1920 |
| ttttatttta ttttatttta ttttatttta ttttatttta ttttatttta ttttatttta | 1980 |
| ttttatttta ttttatttta ttttatttta ttttatttta ttttatttta ttttatttta | 2040 |
| ttttatttta ttttatttta ttttatttta ttttatttta ttttatttta ttttatttta | 2100 |
| ttttatttta ttttatttta ttttatttta ttttatttta ttttatttta ttttatttta | 2160 |
| ttttatttta ttttatttta ttttatttta ttttatttta ttttatttta ttttatttta | 2220 |
| ttttatttta ttttatttta ttttatttta ttttatttta ttttatttta ttttatttta | 2280 |
| ttttatttta ttttatttta ttttatttta ttttatttta ttttatttta ttttatttta | 2340 |
| ttttatttta ttttatttta ttttatttta ttttatttta ttttatttta ttttatttta | 2400 |
| ttttatttta ttttatttta ttttatttta ttttatttta ttttatttta ttttatttta | 2460 |
| ttttatttta ttttatttta ttttatttta ttttatttta ttttatttta ttttatttta | 2520 |
| ttttatttta ttttatttta ttttatttta ttttatttta ttttatttta ttttatttta | 2580 |
| ttttatttta ttttatttta ttttatttta ttttatttta ttttatttta ttttatttta | 2640 |
| ttttatttta ttttatttta ttttatttta ttttatttta ttttatttta ttttatttta | 2700 |
| ttttatttta ttttatttta ttttatttta ttttatttta ttttatttta ttttatttta | 2760 |
| ttttatttta ttttatttta ttttatttta ttttatttta ttttatttta ttttatttta | 2820 |
| ttttatttta ttttatttta ttttatttta ttttatttta ttttatttta ttttatttta | 2880 |
| ttttatttta ttttatttta ttttatttta ttttatttta ttttatttta ttttatttta | 2940 |
| ttttatttta ttttatttta ttttatttta ttttatttta ttttatttta tttcatttca | 3000 |
| tttcatttca tttcatttca tttcatttca tttcatttca tttcatttca tttcatttca | 3060 |
| tttcatttca tttcatttca tttcatttca tttcatttca tttcatttca tttcatttca | 3120 |
| tttcatttca tttcatttca tttcatttca tttcatttca tttcatttca tttcatttca | 3180 |

| tttcatttca tttcatttca tttcatttca tttcatttca tttcatttca tttcatttca | 3240 |
| tttcatttca tttcatttca tttcatttca tttcatttca tttcatttca tttcatttca | 3300 |
| tttcatttca tttcatttca tttcatttca tttcatttca tttcatttca tttcatttca | 3360 |
| tttcatttca tttcatttca tttcatttca tttcatttca tttcatttca tttcatttca | 3420 |
| tttcatttca tttcatttca tttcatttca tttcatttca tttcatttca tttcatttca | 3480 |
| tttcatttca tttcatttca tttcatttca tttcatttca tttcatttca tttcatttca | 3540 |
| tttcatttca tttcatttca tttcatttca tttcatttca tttcatttca tttcatttca | 3600 |
| tttcatttca tttcatttca tttcatttca tttcatttca tttcatttca tttcatttca | 3660 |
| tttcatttca tttcatttca tttcatttca tttcatttca tttcatttca tttcatttca | 3720 |
| tttcatttca tttcatttca tttcatttca tttcatttca tttcatttca tttcatttca | 3780 |
| tttcatttca tttcatttca tttcatttca tttcatttca tttcatttca tttcatttca | 3840 |
| tttcatttca tttcatttca tttcatttca tttcatttca tttcatttca tttcatttca | 3900 |
| tttcatttca tttcatttca tttcatttca tttcatttca tttcatttca tttcatttca | 3960 |
| tttcatttca tttcatttca tttcatttca tttcatttca tttcatttca tttcatttca | 4020 |
| tttcatttca tttcatttca tttcatttca tttcatttca tttcatttca tttcatttca | 4080 |
| tttcatttca tttcatttca tttcatttca tttcatttca tttcatttca tttcatttca | 4140 |
| tttcatttca tttcatttca tttcatttca tttcatttca tttcatttca tttcatttca | 4200 |
| tttcatttca tttcatttca tttcatttca tttcatttca tttcatttca tttcatttca | 4260 |
| tttcatttca tttcatttca tttcatttca tttcatttca tttcatttca tttcatttca | 4320 |
| tttcatttca tttcatttca tttcatttca tttcatttca tttcatttca tttcatttca | 4380 |
| tttcatttca tttcatttca tttcatttca tttcatttca tttcatttca tttcatttca | 4440 |
| tttcatttca tttcatttca tttcatttca tttcatttca tttcatttca tttcatttca | 4500 |
| tttcatttca tttcatttca tttcatttca tttcatttca tttcatttca tttcatttca | 4560 |
| tttcatttca tttcatttca tttcatttca tttcatttca tttcatttca tttcatttca | 4620 |
| tttcatttca tttcatttca tttcatttca tttcatttca tttcatttca tttcatttca | 4680 |
| tttcatttca tttcatttca tttcatttca tttcatttca tttcatttca tttcatttca | 4740 |
| tttcatttca tttcatttca tttcatttca tttcatttca tttcatttca tttcatttca | 4800 |
| tttcatttca tttcatttca tttcatttca tttcatttca tttcatttca tttcatttca | 4860 |
| tttcatttca tttcatttca tttcatttca tttcatttca tttcatttca tttcatttca | 4920 |
| tttcatttca tttcatttca tttcatttca tttcatttca tttcatttca tttcatttca | 4980 |
| tttcatttca tttcatttca tttcatttca tttcatttca tttcatttca tttcatttca | 5040 |
| tttcatttca tttcatttca tttcatttca tttcatttca tttcatttca tttcatttca | 5100 |
| tttcatttca tttcatttca tttcatttca tttcatttca tttcatttca tttcatttca | 5160 |
| tttcatttca tttcatttca tttcatttca tttcatttca tttcatttca tttcatttca | 5220 |
| tttcatttca tttcatttca tttcatttca tttcatttca tttcatttca tttcatttca | 5280 |

<210> SEQ ID NO 33
<211> LENGTH: 2635
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 33

| | | | | | |
|---|---|---|---|---|---|
| ttttatttta | ttttatttta | ttttatttta | ttttatttta | ttttatttta | ttttatttta | 60
| ttttatttta | ttttatttta | ttttatttta | ttttatttta | ttttatttta | ttttatttta | 120
| ttttatttta | ttttatttta | ttttatttta | ttttatttta | ttttatttta | ttttatttta | 180
| ttttatttta | ttttatttta | ttttatttta | ttttatttta | ttttatttta | ttttatttta | 240
| ttttatttta | ttttatttta | ttttatttta | ttttatttta | ttttatttta | ttttatttta | 300
| ttttatttta | ttttatttta | ttttatttta | ttttatttta | ttttatttta | ttttatttta | 360
| ttttatttta | ttttatttta | ttttatttta | ttttatttta | ttttatttta | ttttatttta | 420
| ttttatttta | ttttatttta | ttttatttta | ttttatttta | ttttatttta | ttttatttta | 480
| ttttatttta | ttttatttta | ttttatttta | ttttatttta | ttttatttta | ttttatttta | 540
| ttttatttta | ttttatttta | ttttatttta | ttttatttta | ttttatttta | ttttatttta | 600
| ttttatttta | ttttatttta | ttttatttta | ttttatttta | ttttatttta | ttttatttta | 660
| ttttatttta | ttttatttta | ttttatttta | ttttatttta | ttttatttta | ttttatttta | 720
| ttttatttta | ttttatttta | ttttatttta | ttttatttta | ttttatttta | ttttatttta | 780
| ttttatttta | ttttatttta | ttttatttta | ttttatttta | ttttatttta | ttttatttta | 840
| ttttatttta | ttttatttta | ttttatttta | ttttatttta | ttttatttta | ttttatttta | 900
| ttttatttta | ttttatttta | ttttatttta | ttttatttta | ttttatttta | ttttatttta | 960
| ttttatttta | ttttatttta | ttttatttta | ttttatttta | ttttatttta | ttttatttta | 1020
| ttttatttta | ttttatttta | ttttatttta | ttttatttta | ttttatttta | ttttatttta | 1080
| ttttatttta | ttttatttta | ttttatttca | tttcatttca | tttcatttca | tttcatttca | 1140
| tttcatttca | tttcatttca | tttcatttca | tttcatttca | tttcatttca | tttcatttca | 1200
| tttcatttca | tttcatttca | tttcatttca | tttcatttca | tttcatttca | tttcatttca | 1260
| tttcatttca | tttcatttca | tttcatttca | tttcatttca | tttcatttca | tttcatttca | 1320
| tttcatttca | tttcatttca | tttcatttca | tttcatttca | tttcatttca | tttcatttca | 1380
| tttcatttca | tttcatttca | tttcatttca | tttcatttca | tttcatttca | tttcatttca | 1440
| tttcatttca | tttcatttca | tttcatttca | tttcatttca | tttcatttca | tttcatttca | 1500
| tttcatttca | tttcatttca | tttcatttca | tttcatttca | tttcatttca | tttcatttca | 1560
| tttcatttca | tttcatttca | tttcatttca | tttcatttca | tttcatttca | tttcatttca | 1620
| tttcatttca | tttcatttca | tttcatttca | tttcatttca | tttcatttca | tttcatttca | 1680
| tttcatttca | tttcatttca | tttcatttca | tttcatttca | tttcatttca | tttcatttca | 1740
| tttcatttca | tttcatttca | tttcatttca | tttcatttca | tttcatttca | tttcatttca | 1800
| tttcatttca | tttcatttca | tttcatttca | tttcatttca | tttcatttca | tttcatttca | 1860
| tttcatttca | tttcatttca | tttcatttca | tttcatttca | tttcatttca | tttcatttca | 1920
| tttcatttca | tttcatttca | tttcatttca | tttcatttca | tttcatttca | tttcatttca | 1980
| tttcatttca | tttcatttca | tttcatttca | tttcatttca | tttcatttca | tttcatttca | 2040
| tttcatttca | tttcatttca | tttcatttca | tttcatttca | tttcatttca | tttcatttca | 2100
| tttcatttca | tttcatttca | tttcatttca | tttcatttca | tttcatttca | tttcatttca | 2160
| tttcatttca | tttcatttca | tttcatttca | tttcatttca | tttcatttca | tttcatttca | 2220
| tttcatttca | ttttatttta | ttttatttta | ttttatttta | ttttatttta | ttttatttta | 2280

| ttttatttta ttttatttta ttttatttta ttttatttta ttttatttta ttttatttta | 2340 |
| ttttatttta ttttatttta ttttatttta ttttatttta ttttatttta ttttatttta | 2400 |
| ttttatttta ttttatttta ttttatttta ttttatttta ttttatttta ttttatttta | 2460 |
| ttttatttta ttttatttta ttttatttta ttttatttta ttttatttta ttttatttta | 2520 |
| ttttatttta ttttatttta ttttatttta ttttatttta ttttatttta ttttatttta | 2580 |
| ttttatttta ttttatttta ttttatttta ttttatttta ttttatttta tttta | 2635 |

<210> SEQ ID NO 34
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tttcatttca tttcatttca tttcatttca tttcatttca tttcatttca tttcatttca    60

<210> SEQ ID NO 35
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
ttttatttta ttttatttta ttttatttta ttttatttta ttttatttta ttttatttta    60
ttttatttta ttttatttta ttttatttta ttttatttta ttttatttta              110

<210> SEQ ID NO 36
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
ttttatttta ttttatttta ttttatttta ttttattatt ttattttatt ttattttatt    60
ttattttatt ttattttatt ttattttatt ttattttatt ttattttatt ttattttatt   120
tta                                                                  123

<210> SEQ ID NO 37
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ttttatttta ttttatttta ttttatttta ttttattatt ttattttatt ttattttatt    60
ttattttatt ttattttatt ttattttatt tta                                 93

<210> SEQ ID NO 38
<211> LENGTH: 85
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 38
ttttatttta ttttatttta ttttatttta ttttatttta ttttatttta ttttatttta        60
ttttatttta ttttatttta tttta                                              85

<210> SEQ ID NO 39
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ttttatttta ttttatttta ttttatttta ttttatttta ttttatttta tttta             55

<210> SEQ ID NO 40
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tttcatttca tttcatttca tttcatttca tttcatttca tttcatttca tttcatttca        60
ttgagacaga gtttcactct tgttgcccag g                                       91

<210> SEQ ID NO 41
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttttatttta ttttatttta ttttatttta ttttatttga gacagagttt cactcttgtt        60
gcccagg                                                                  67

<210> SEQ ID NO 42
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gttcattttt attttatttt attttatttt attttatttt attatttat tttatttat          60 tttatttat tttatttat tttatttat tttatttat tttatttat ttga                   114

<210> SEQ ID NO 43
<211> LENGTH: 950
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
```

```
gttcattttt attttatttt ttatttttatt ttatttttatt ttatttttatt ttatttttatt      60 ttatttttatt ttatttttatt ttatttttatt ttatttttatt ttatttttatt ttatttttatt    120 ttatttttatt ttatttttatt ttatttttatt ttatttttatt ttatttttatt ttatttttatt    180 ttatttttatt ttatttttatt ttatttttatt ttatttttatt ttatttttatt ttatttttatt    240 ttatttttatt ttatttttatt ttatttttatt ttatttttatt ttatttttatt ttatttttatt    300 ttatttttatt ttatttttatt ttatttttatt ttatttttatt ttatttttatt ttatttttatt    360 ttatttttatt ttatttttatt ttatttttatt ttatttttatt ttatttttatt ttatttttatt    420 ttatttttatt ttatttttatt ttatttttatt ttatttttatt ttatttttatt ttatttttatt    480 ttatttttatt ttatttttatt ttatttttatt ttatttttatt ttatttttatt ttatttttatt    540 ttatttattt tatttttattt tatttattttt attttattttt attttattttt attttatttt      600 attttatttt attttatttc atttcatttc atttcatttc atttcatttc atttcatttc          660
atttcatttc atttcatttc atttcatttc atttcatttc atttcatttc atttcatttc          720
atttcatttc atttcatttc atttcatttc atttcatttc atttcatttc atttcatttc          780
atttcatttc atttcatttc atttcatttc atttcatttc atttcatttc atttcatttc          840
atttcatttc atttcatttc atttcatttc atttcatttc atttcatttc atttcatttc          900
atttcatttc atttcatttc atttcatttc atttcatttc atttcattga                    950
```

<210> SEQ ID NO 44
<211> LENGTH: 1013
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

```
gttcattttt attttatttt attttttat tttattttat tttattttat tttattttat        60
tttattttat tttattttat tttattttat tttattttat tttattttat tttattttat       120
tttattttat tttattttat tttattttat tttattttat tttattttat tttattttat       180
tttattttat tttattttat tttattttat tttattttat tttattttat tttattttat       240
tttattttat tttattttat tttattttat tttattttat tttattttat tttattttat       300
tttattttat tttattttat tttattttat ttcatttcat ttcatttcat ttcatttcat       360
ttcatttcat ttcatttcat ttcatttcat ttcatttcat ttcatttcat ttcatttcat       420
ttcatttcat ttcatttcat ttcatttcat ttcatttcat ttcatttcat ttcatttcat       480
ttcatttcat ttcatttcat ttcatttcat ttcatttcat ttcatttcat ttcatttcat       540
ttcatttcat ttcatttcat ttcatttcat ttcatttcat ttcatttcat ttcatttcat       600
ttcatttcat ttcatttcat ttcatttcat ttcattttat tttattttat tttattttat       660
tttattttat tttattttat tttattttat tttattttat tttattttat tttattttat       720
tttattttat tttattttat tttattttat tttattttat tttattttat tttattttat       780
tttattttat tttattttat tttattttat tttattttat tttattttat tttattttat       840
tttattttat tttattttat tttattttat tttattttat tttattttat tttattttat       900
tttattttat tttattttat tttattttat tttattttat tttattttat tttattttat       960
tttattttat tttattttat tttattttat tttattttat ttatttttatt tga            1013
```

<210> SEQ ID NO 45

```
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ttttatttta ttttatttta ttttatatta ttttatttta ttttatttta ttttatttta      60
ttttatttta ttttatttta ttttatttta                                       90

<210> SEQ ID NO 46
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46 tatcccccctt tcatttttgt tcatttttat tttattttat tttattttat tttatttta      59

<210> SEQ ID NO 47
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47 tatcccccctt tcatttttgt tcatttttat tttatttttt tatttttattt ta            52

<210> SEQ ID NO 48
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48 tatcccccctt tcatttttgt tcatttttat tttatttttt tatttttattt tatttttattt   60 tatttttattt tatttttattt tatttttattt tatttttattt tatttttattt tatttttattt  120 tatttttattt tattt                                                      135

<210> SEQ ID NO 49
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tttcatttca tttcatttca tttcatttca tttcatttca tttcatttca tttcatttca      60
ttgagacaga gtttcactct tgttgcccag g                                     91

<210> SEQ ID NO 50
<211> LENGTH: 5346
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 50

```
ttttatttta ttttattttt attttattttt attttatttt tatttatttt tatttatttt          60
tatttatttt tatttatttt tatttatttt tatttatttt tatttatttt ttatttatt           120
tatttatt ttatttatt ttatttatt tttatttat tttatttat ttatttat                   180
ttatttat ttatttat tttgtttat ttgtttatt ttatttatt tttatttat                   240
ttattttaat tttattttat ttgtattttt cattttatt ttatttatt ttatttatt              300
tatttatt attttatttt attttatttt gtttttattt tatttatttt tatttatttt             360
tatttgttt tatttattt tatttatttt tatttatttt ccattttatt ttatttatt              420
ttatttgtt ttatttgtt tgttttatt atttatttta atttatttt atttgtttat               480
tttgttttat tttatttgt tttatttta ttttatttta ttttatttta tttatttt               540
atttaattt tatttatttt ttaatttat tttgttttat tttatttgtt tgtttatt               600
tgttttatt tatttattt tatttttatt ttattttatt ttatttatt ttatttatt               660
tttatttat ttatttta tttttatttt attttatttt attttatttt attttattt               720
tatttgttt tgtttattt tttatttat tttatttta ttttatttta ttttatttta               780
ttttatttta ttttatttgt tttatttat tttatttt attttatttt attttatttt              840
attttgttt tatttattt tatttgttt ttatttatt ttatttgat tttatttcca                900
ttttatttta ttttatttta ttttgtttta ttttattttt attttatttt attttgttt            960
atttattt attttaattt tatttatttt tatttatttt tatttatttt ttatttatttt           1020
tatttatttt cattttattt tatttatttt attttatttt gttttatttt attttatttt          1080
tatttatttt ttatttatt ttatttatt tatttatttt tatttatttt tatttatttt            1140
ttatttat tttatttta tttatttat tttatttat tttatttat tttatttat                 1200
tttgtttact gatttatt tatttgttt ccatttatt ttatttggtg atcatttat                1260
tttgttat ttttatttta ttttatttta tttgttat tttgttttta ttttatttta              1320
ttttatttta ttttatttta ttttatttta ttttatttta ttttattttt attttatttt          1380
atttatttt attttatttt gttttatttt tatttatttt tatttatttt ttatttatt            1440
tttatttaa tttttatttt attttatttt attttatttt tgttttatt tatttatttt            1500
tatttatttt attttatttt attttgtttt tatttatt ttatttatt tatttatt               1560
ttatttatt ttatttat tttgttgt tttatttat tttgttat ttaatttta                   1620
ttttatttta tttatttat tttatttat ttttatttta ttttgttta ttttatttta             1680
ttttatttta ttttatttta ttttatttta ttttatttta ttttatttt attttatttt           1740
atttatttt attttatttt attttatttt attttatttt attttgtttt aattttatttt          1800
tatttatttt tatttatttt tatttatt ttatttatt ttatttatt ttatttatt               1860
ttgtttatt aatttatttt ttatttatt ttatttatt ttatttatt ttatttatt               1920
ttatttatt ttatttatt ttatttatt ttatttatt tttatttaa ttttatttta               1980
ttttatttgt attttatta ttttatttta tttgtttt atttatttt attttatttt              2040
attttatttt attatttta tttatttta ttttatttt tatttatttt tatttgatt              2100
ttatttatt ttatttatt ttatttatt tttatttat tttatttta tttatttat                2160
tttatttat ttcatttat tttatttat tttgttgtt ttatttttat tttgatttta              2220
ttttatttta ttttattcat attttatttt attttatttt acatttat tttaatttta            2280
```

```
ttttatttta atttcatttt atttttattt attttattttt tatttttattt tattttattt   2340 atttttatttt gttttaattt tatttttattt tattttgttt tattttattt tattttattt   2400
tattttattt tattttattt tattttattt tatttttatt ttgttttatt ttatttttgtt   2460 ttatttttatt ttattttgtt tatttttattt tgtttatttg acattttatt ttaattttat   2520
tttattttat ttttgtttta ttttaattttt atttttattt atttttatttt taattttatt   2580 ttatttttatt ttattttttaa ttttttattt attttattttt gtatttttatt ttattttttat  2640 tttatttttat tttatttttgt tttaattttt attttgtttt gttttattttt attttattttt   2700 atcattattt tattttattt tacattttat tttgtatttt attttattttt attttattttt   2760 atttttattt tatttcattt tatttttattt tgttttatttt tatttttattt tatttttattt   2820 tgttttattt tgattttatt ttatttttatt ttatttttatt ttttatttttat ttttatttttat  2880 ttgttttatt ttatttttatt ttatttttatt ttatttttatt ttatttttatt ttgttttatt   2940 ttatttttatt tatttttatt tatttgtttt atttttattt atttttattt atttttatttta   3000 gatgatttta ttttatttta atttttattt atttttattt atttttattt atttttattt   3060
atttttattc atttcatttc atttcattttc atttcgtttc atttcgtttc atttcatttc   3120 atttcatttta tttcatttca tcatttcatt tcattcattt catttcatttt catttcatttt   3180 catttcatttt catttcattt catttcattt catttcattt catttcattt catttcattt   3240
catttcattt catttcattt catttcattt catttcattt catttcattt catttatttc   3300
atttcatttc atttcatttc atttcatttc atttctttca tttcatttca tttcatttca   3360
tttcatttca tttcattcgt ttcatttcat ttcatttcat ttcatttcat ttcatttcat   3420
ttcattttca tttcatttat ttcatttcat ttcatttcat ttcatttcat tttatttcgt   3480
ttcatttcat ttcatttcat ttcatttcat tcatttcatt tcattttttca tttcatttca   3540 tttatttttt catttcatttt catttcattt atttcatttc atttcatttc atttcatttc   3600
atttatttca tttcattcat ttatttcatt tcatttcatt tcatttattt catttcattt   3660
catttctgtt tcatttcatt tcatttcatt tcatttcatt tcattttcat ttcatttatt   3720
catttcattt catttcattc atttcatttc atttcatttc atttcatttc atttcatttc   3780
atttcatttc atttcatttt catttattttc atttcatttc atttcatttc atttcatttc   3840
atttcatttc atttcatttc atttcattca tttatttcat ttcatttcat ttcatttcat   3900
ttcatttcat ttcattcatt tcattttcat ttatttcatt tcatttcatt ttcatttcat   3960
ttcatttcat ttcatttcat ttcatttcat ttcatttcat ttcatttcat ttcatttcat   4020
ttcatttcat ttcatttatt tcatttcatt tcatttcatt ctttcatttc atttcatttc   4080
atttcatttc atttcatttc atttttcattt catttcattt catttgtttc atttcatttc   4140 atttcatttta tttcattttc attatttttca tttcatttca tttcatttca tttcatttca   4200
tttcatttca tttcatttca tttctatttt agtttcgttc atttcatttc gtttcattttt   4260 catttcattt catttcattt catttcattt catttcatttt cgtttcattt catttcattt   4320
catatttcat ttcatttcat ttcatttcgt ttcatttcat ttcatttcat ttcatttcat   4380
ttcatttcat tcgtttcatt ttcatttcat ttcatttcat ttcatttcat ttcatttcat   4440
ttcatttcat ttcatttcat ttcatttcat tttatttcat ttcattttca tttcatttca   4500
tttcatttaa tttcatttca ttcattttta tttcatttca tttcatttca tttcatttca   4560
tttcatttca tttcatttca tttcatttca tttcatttca tttcatttca tttcatttca   4620
tttcatttca tttcattcat ttcatttcat ttcatttcga tatttcattt catttttattt   4680
```

| | | | | | |
|---|---|---|---|---|---|
| ttcattttgt | tttcatttca | tttcatttca | tttcatttca | ttttcatttc | atttcatttc | 4740 |
| atttcatttc | atttcatttc | attttcattt | catttcattt | catttcattt | catttcattt | 4800 |
| cattttattt | tcatttcatt | tcatttcatt | tcatttcatt | tcattcattt | catttcattt | 4860 |
| catttcattt | catttcattt | catttcattt | catttcattt | catttcattc | attcatttca | 4920 |
| tttatttcat | ttcatttcat | ttcatttcat | ttcattttat | ttcatttcat | ttcatttcat | 4980 |
| ttcatttcat | tcgttcattt | catttcattt | catttcattt | catttcattt | catttcattt | 5040 |
| catttcattt | catttcattt | catttcattt | cattcatttc | atttcatttc | atttcatttc | 5100 |
| atttcatttc | atttcatttc | attttcatttc | atttcattca | tttcatttca | ttcatttcat | 5160 |
| ttggtcgatt | tcatttcatt | tcattctact | atttcatttc | atttgtttca | tttcatttca | 5220 |
| tttcatttca | tttcatttca | tttcatttca | tttattcatt | tcatttcatt | tcatttcact | 5280 |
| attttcattt | catttcattc | atttcatttc | atttcatttc | atttcatttc | atttcatttc | 5340 |
| atttca | | | | | | 5346 |

<210> SEQ ID NO 51
<211> LENGTH: 2630
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

| | | | | | |
|---|---|---|---|---|---|
| tttttatttt | attttatttt | tattttattt | tattttattt | tattttattt | tattttattt | 60 |
| tattttattt | tattttatttt | attttatttt | attttattta | ttttattttta | ttttatttta | 120 |
| ttttatttta | ttttatttta | ttttatttta | ttttatttta | ttttatttta | ttttatttta | 180 |
| ttttatttta | ttttatttta | ttttatttta | ttttatttat | ttatttttat | ttgtttatt | 240 |
| ttgttttgat | tttatttttat | tttatttttat | tttatttttat | ttgttttgtt | ttatttattt | 300 |
| tattttattt | tgtttattt | tatttatttt | gtttatttta | ttttatttta | ttttatttta | 360 |
| tttattttat | tttattttat | tttatttta | ttttatttt | atttgtttt | attttatttt | 420 |
| tattttgttt | attttatttt | tattttattt | tgtttatttt | attttatttt | attttatttt | 480 |
| tattttattt | tattttattt | tattttattt | tattttattt | tattttattt | tattttattt | 540 |
| tattttattt | tattttcaat | tttatttttta | ttttattttg | attttatttt | tattttatttt | 600 |
| tattttattt | tatttgtttt | tattttatttt | tattttgttt | attttatttt | atttatttat | 660 |
| tttgttttca | tttcttgttt | tattttattt | tattttattt | tattttattc | attttatttt | 720 |
| attttatttt | gttttatttt | attttatttt | gtttatttta | ttttgtttga | ttttatttttt | 780 |
| attttatttt | attttatttt | attttatttt | gtttcatttt | attttatttt | attttatttt | 840 |
| attttaattt | tattttattt | tattttattt | tattttattt | tattttattt | ttatttttatt | 900 |
| ttgttttatt | ttattttgtt | ttattttatt | tatttatttt | attttatttt | attttatttt | 960 |
| attttatttt | ttatttgttt | tattttatttt | attttatttt | attttatttt | attttatttt | 1020 |
| tattttgttt | tattttatttt | tattttattt | attttatttt | attttatttt | attttatttt | 1080 |
| attttattta | tttatttatt | tatttatttc | atttcattta | tcattcattt | catttgtttt | 1140 |
| catttcattt | catttcattt | catttcattt | cattcatttc | atttcatttc | atttcatttc | 1200 |
| atttatttca | tttcatttc | atttatttcg | tttcatttca | tttcatttca | tttcatttta | 1260 |
| tttcatttca | tttcatttca | tttcatttca | tttcatttca | tttcatttca | tttcatttca | 1320 |

```
tttttcatttc atttcatttc atttcatttc atttcatttc attcatttca tttatttcat    1380
ttcatttcat ttatttcatt tcattttcat tcatttttcat ttcattcatt tcagctgttt    1440
catttcattt catttctatt tcattcatt tcatttcatt tcatttcatt tcatttcatt      1500
tcatttattc atttcatttc atttcatttc atttcatttc atttatttca tttcatttta    1560
tttcatttca ttttatttca tttcatttct atttcatttc atttcattt atttcatttt     1620 catttatttc attcgtttca tttcatttca tttcatttca tttcatttca ttttcatttc    1680
atttcatttc atttcatttc atttcatttc atttcatttc atttcatttc atttcatttc    1740
atttcatttc atttcatttc attcatttca tttcattttc atttcaagtt tcatttcatt    1800
tcatttcatt tcatttcatt tcatttattt catttcattt catttcattt catttcattt    1860
catttcattt catttcattt catttcgttt catttcattt tatttcattt catttcattt    1920
catttcattt catttcattt atttcgtttc atttcattta tttcattcat ttcatttcat    1980
ttcatttcat ttcatttcat ttcatttcat ttcatttcat tttgtttcat ttcatttatt    2040
tcattccttt ctctattttc atttcatttc attcatttca tttattcatt tcattttatt    2100
tcatttattt catttcattt cttttcattt catttcattt catttcattt catttcattt    2160
catttcattt catttcattt catttcattt catttcattt catttctcat ttcatttttca   2220 tttcgactt catttatttt tatttattttt attttatttt attttgtttat tttatttttat  2280 tttatttttat tttatttttat tttatttttat tttatttgtt tattttatt attttatttt  2340 attttattta ttttatttta ttttatttta ttttatttta ttttatttta ttttatttt     2400 attttatttt attttattt attttatttt attttattt attttattt ttttattttat     2460 tttatttttat tttatttttat tttatttttat ttatttttat ttattttatt ttattttga  2520 tgatttttat ttattttttat tttatttttat tttatttttat tttatttttat tttatttttat 2580 tttatttttat tttatttttat tttatttttgt tttatttttta tttttgttttta          2630

<210> SEQ ID NO 52
<211> LENGTH: 247
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52 attttattt attttattt attttattt attttattt attttattt attttattt            60 attttattt attttattt attttattt attttattt attttattt attttattt           120 attttattt attttattt attttattt tattttattt tattttattt tattttattt         180
tattttattt tattttattt tattttattt tattttattt tattttattt acttatttat     240
ttagaga                                                                247

<210> SEQ ID NO 53
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53 tttatttat tttatttat tttatttat tttatttat tttatttat ttatttttat           60 tttatttttat tttatttttat tttatttttat tttatttttat ttacttattt atttagaga  119
```

<210> SEQ ID NO 54
<211> LENGTH: 269
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
caatgagcaa ctattaaagc attttatttt attttatttt attttatttt attttatttt      60
attttatttt attttatttt attttatttt attttatttt attttatttt attttatttt     120
attttatttt atttcatttc atttcatttc atttcatttc atttcatttc atttcatttc     180
atttcatttc atttcatttc atttcatttc atttcatttc atttcatttc atttcatttc     240
atttcatttc atttcatttc atttcattt                                       269

<210> SEQ ID NO 55
<211> LENGTH: 265
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
tattaaagca ttttatttta ttttatttta ttttatttta ttttatttta ttttatttta      60
ttttatttta ttttatttta ttttatttta ttttatttta ttttatttta ttttatttta     120
tttcatttca tttcatttca tttcatttca tttcatttca tttcatttca tttcatttca     180
tttcatttca tttcatttca tttcatttca tttcatttca tttcatttca tttcatttca     240
tttcatttca tttcatttca tttca                                           265

<210> SEQ ID NO 56
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tcatttcatt tcatttcatt tcatttttatt actagaggat a                         41

<210> SEQ ID NO 57
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ttcatttcat ttcatttcat ttcatttcat ttcattttat tttattttat tactagagga      60
ta                                                                    62

<210> SEQ ID NO 58
<211> LENGTH: 127
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
ttcatttcat ttcatttcat ttcatttcat ttcatttcat ttcatttcat ttcatttcat     60
ttcatttcat ttcatttcat ttcatttcat ttcatttcat tttatttat tttattacta     120 gaggata                                                                127

<210> SEQ ID NO 59
<211> LENGTH: 146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
cattactatc atagctttta ttttatttta ttttatttta ttttatttta ttttatttta     60
ttttatttta ttttatttta ttttatttta ttttatttta ttttatttta ttttatttta     120
ttttatttta ttttatttta tttat                                            146

<210> SEQ ID NO 60
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
attactatca tagcttttat tttattttat tttattttat tttattttat tttattttat     60
tttattttat tttattttat tttattttat tttattttat tttattttat tttattttat     120
tttattttat tttattttat tttattttat                                       150

<210> SEQ ID NO 61
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
ttttatttta ttttatttta ttttatttta ttttatatta ttttatttta ttttatttta     60
ttttatttta ttttatttta ttttatttta ttttatttta ttttatttta                110

<210> SEQ ID NO 62
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ttttatttta ttttatttta ttttatatta ttttatttta ttttatttta ttttatttta     60
ttttatttta ttttatttta tttta                                            85

<210> SEQ ID NO 63
<211> LENGTH: 10
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: See specification as filed for detailed
      description of substitutions and preferred embodiments

<400> SEQUENCE: 63
tttcatttta                                                              10

<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
tgtaaaacga cggccagtca gttcaaagtg cgtaaagtac                             40

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
caagtagagc tcacgattag taac                                              24

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tgtaaaacga cggccagt                                                     18

<210> SEQ ID NO 67
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
tgtaaaacga cggccagtat aaatggctgc atgctag                                37

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ctcagataat ggaatgaaga ctaa                                              24

<210> SEQ ID NO 69
<211> LENGTH: 36
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 69
tgtaaaacga cggccagtga aaacaaaaca ggctcc                                  36

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
tgaccaaaca actagacacc                                                    20

<210> SEQ ID NO 71
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tgtaaaacga cggccagttt ccacccccaa aaga                                    34

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
caaaggtttt taacatccca                                                    20

<210> SEQ ID NO 73
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
tgtaaaacga cggccagttg gttctgcttt ttctctcc                                38

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
tttaacagac aaatgacaaa tctg                                               24

<210> SEQ ID NO 75
<211> LENGTH: 38
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 75
tgtaaaacga cggccagtgg tgacataggc atcacaca                                38

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
tctccaattc agagagctgc                                                    20

<210> SEQ ID NO 77
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tgtaaaacga cggccagtcc aagatcacac tactgccc                                38

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
agcctcctct gtcaaggagt                                                    20

<210> SEQ ID NO 79
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tgtaaaacga cggccagtgc agaagcctgg tcat                                    34

<210> SEQ ID NO 80
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80 tcagccccctt aatcaca                                                      17

<210> SEQ ID NO 81
<211> LENGTH: 37
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 81
tgtaaaacga cggccagtcc tcaaggtatc aggctgc                              37

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ttaagtacat ggtccgtccc                                                 20

<210> SEQ ID NO 83
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
tgtaaaacga cggccagtcc agtcaacccc aacac                                35

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gaaatgaaac atgatgacac c                                               21

<210> SEQ ID NO 85
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
tgtaaaacga cggccagttg cctttaagaa tgcaatg                              37

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
tggtgtcaac gcagtaaat                                                  19

<210> SEQ ID NO 87
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 87
cttgagcccc agacaagaat                                                    20

<210> SEQ ID NO 88
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
caggaaacag ctatgaccaa aataaaataa aataaaat                                38

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
caggaaacag ctatgacc                                                      18

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
tgctactgta aaaagataaa caaaatg                                            27

<210> SEQ ID NO 91
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
caggaaacag ctatgacctt tcatttcatt tcatttcatt tca                          43

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tgtggagctc caaagccctg                                                    20

<210> SEQ ID NO 93
<211> LENGTH: 43
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 93
tgtaaaacga cggccagttg aaatgaaatg aaatgaaatg aaa                         43

<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
tgtaaaacga cggccagt                                                    18

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ccaagtatgc tccttcccta ctt                                              23

<210> SEQ ID NO 96
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
tgtaaaacga cggccagttt ttattttatt ttattttatt tta                        43

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ttagtcattt tctctgtctg ggag                                             24

<210> SEQ ID NO 98
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tgtaaaacga cggccagtta aaataaaata aaataaaata aaa                        43

<210> SEQ ID NO 99
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 99
gcagtatgta cacatagcag tgc                                              23

<210> SEQ ID NO 100
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tgtaaaacga cggccagttt tcatttcatt tcatttcatt tca                        43

<210> SEQ ID NO 101
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
aaaggatgag gg                                                          12

<210> SEQ ID NO 102
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
aatatatata tg                                                          12

<210> SEQ ID NO 103
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
aaagttcatg gt                                                          12

<210> SEQ ID NO 104
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
atttcatttc atttcatttc atttcatttc atttcatttc atttcatttc atttcatttc      60
at                                                                     62

<210> SEQ ID NO 105
<211> LENGTH: 54
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 105
aaatgaaatg aaatgaaatg aaatgaaatg aaatgaaatg aaatgaaatg aaat            54

<210> SEQ ID NO 106
<211> LENGTH: 237
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
tttattttat tttattttat tttattttat tttattttat tttattttat tttattttat     60
tttattttat tttattttat tttattttat tttattttat tttattttat tttattttat    120
tttattttat tttattttat tttattttat tttattttat tttattttat tttattttat    180
tttattttat tttattttat tttattttat tttattttat tttattttat tttattt       237

<210> SEQ ID NO 107
<211> LENGTH: 306
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
aaataaaata aaataaaata aaataaaata aaataaaata aaataaaata aaataaaata     60
aaataaaata aaataaaata aaataaaata aaataaaata aaataaaata aaataaaata    120
aaataaaata aaataaaata aaataaaata aaataaaata aaataaaata aaataaaata    180
aaataaaata aaataaaata aaataaaata aaataaaata aaataaaata aaataaaata    240
aaataaaata aaataaaata aaataaaata aaataaaata aaataaaata aaataaaata    300
aaataa                                                                306

<210> SEQ ID NO 108
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
tttattttat tttattttat tttattttat tttattttat tttattttat tttatttt       58

<210> SEQ ID NO 109
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
tttattttat tttattttat tttattttat tttattttat tttattttat tttattttat     60
tttatttt                                                              68
```

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
tacaggggtt tttgccagac                                                20

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
ccaacctcaa atgcattgac cac                                            23

<210> SEQ ID NO 112
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
ggatcattcc tgatagaaaa agtcc                                          25

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
agcggctaat ggtagataag g                                              21

<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
attcacatac ctttctgtct ccc                                            23

<210> SEQ ID NO 115
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gcattctaca ctgtcttagt ga                                             22

```
<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
tcactaagac agtgtagaat gc                                              22

<210> SEQ ID NO 117
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
tcacaattca catttggctt cc                                              22

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
actagaggat atttgctcag tcgg                                            24

<210> SEQ ID NO 119
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ggtgattctc agcacatcct actata                                          26

<210> SEQ ID NO 120
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
tatagtagga tgtgctgaga atcacc                                          26

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tttaattgca caactttcc cttc                                             24

<210> SEQ ID NO 122
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
aactttactc actggaatga ggc                                             23

<210> SEQ ID NO 123
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
acagcatcct gggtaaatct aataatc                                         27

<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
tattgtccta aattgctttg cc                                              22

<210> SEQ ID NO 125
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ggaaagatga agtgtaattt agctcc                                          26

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
cacatcttgc taactaatag ctgg                                            24

<210> SEQ ID NO 127
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
cccagccctc attttgttta tc                                              22

<210> SEQ ID NO 128
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
tgctggctag aggaaccatt                                              20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
tccttaagat ttcccccgac                                              20

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
cacacaagca tcatctgagg g                                            21

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
gcagtgccat gggttagtct                                              20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
aacctcctcc ttttccaagc                                              20

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gcagtacctg tttagccacg a                                            21

<210> SEQ ID NO 134
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 134
ggtgccccat cattttgcag c                                            21

<210> SEQ ID NO 135
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
caactgttct tcttcttgca ctaaatcc                                     28
```

METHOD AND KIT FOR DETERMINING HYPEREXCITABILITY IN SUBJECT

CROSS-REFERENCE TO RELATED PATENT APPLICATIONS

This application is a national stage filing under 35 U.S.C. § 371 of International Application No. PCT/JP2019/004916, filed Feb. 12, 2019, which is based upon and claims priority to U.S. Provisional Application No. 62/628,324, filed Feb. 9, 2018. Each of the above-referenced applications is incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 26, 2022, is named 05905_0344-00000_SL.txt and is 67,380 bytes in size.

TECHNICAL FIELD

A method and a kit for determining a hyperexcitability in a subject are disclosed.

BACKGROUND ART

Benign adult familial myoclonic epilepsy (BAFME) is an autosomal dominant disorder characterized by myoclonic tremor (cortical tremor) and infrequent epilepsy with a benign clinical course (MIM601068). The disease has been variously called including familial essential myoclonus and epilepsy (FEME), cortical tremor, benign adult familial myoclonic epilepsy (BAFME), familial adult myoclonic epilepsy (FAME), autosomal dominant cortical tremor, myoclonus, and epilepsy (ADCME), and familial cortical myoclonic tremor with epilepsy (FCMTE). To date, at least 60 families have been reported in Japan. All the Japanese families and a Chinese family examined to date have been shown to be linked to 8q24. On the other hand, families of Italian, French, and Thai origins with similar clinical presentations with an autosomal dominant inheritance have been shown linkages to 2p (FAME2/FCMTE2), 5p (FAME3/FCMTE3), and 3q (FAME4/FCMTE4), respectively, indicating locus heterogeneity. Uyama et al. estimated the prevalence of BAFME to be 1/35,000 in Kumamoto Prefecture of Japan, suggesting a high prevalence of BAFME in Japan.

SUMMARY OF INVENTION

Technical Problem

Despite the comprehensive mutational analyses of all the exons of the 38 genes located within the candidate region including copy-number analysis, the causative mutations have not been identified.

Solution to Problem

The present inventors identified noncoding TTTCA and TTTTA pentanucleotide repeat expansions in an intron of SAMD12 as the causative mutations in BAFME linked to 8q24. Moreover, the present inventors identified similar TTTCA and TTTTA repeat expansions in TNRC6A and RAPGEF2 in BAFME families in which repeat expansions in SAMD12 were excluded. These findings strongly indicate that the TTTCA and TTTTA pentanucleotide repeat expansions, irrespective of the genes where the expanded repeats are located, play essential roles in the pathogenesis of hyperexcitability including BAFME, presumably through RNA-mediated toxicity mechanisms.

An aspect of the present disclosure relates to a method for determining or diagnosing a hyperexcitability in a subject comprising detecting a repeat expansion of TTTCA, TTTTA, or a complementary sequence thereof in a nucleic acid sample from the subject. Expansions of TTTCA repeats are present exclusively in patients with BAFME, while expansions are infrequently also present in a limited proportion of healthy individuals.

An aspect of the present disclosure relates to a method for treating a hyperexcitability in a subject comprising detecting a repeat expansion of TTTCA, TTTTA, or a complementary sequence thereof in a nucleic acid sample from the subject, and if the repeat expansion is detected, administering a pharmaceutical composition for treating the hyperexcitability to the subject.

In the above method, the nucleic acid sample may be a chromosome DNA. In the above method, TTCA and TTTTA may be in an intron of a gene from the subject. In the above method, the gene may be at least one of SAMD12 gene, TNRC6A gene, and RAPGEF2 gene. In the above method, the repeat expansion may be greater than 50 repeats. The above method may further comprises calculating an anticipated age at onset of the hyperexcitability based on the size of the repeat expansion. In the above method, the hyperexcitability may be a hyperexcitability in the brain. In the above method, the hyperexcitability may be a hyperexcitability in the cerebrum. In the above method, the hyperexcitability may be a hyperexcitability of cortical neurons. In the above method, the hyperexcitability may be an epilepsy. In the above method, the hyperexcitability may be a benign adult familial myoclonic epilepsy.

An aspect of the present disclosure relates to a method for determining or diagnosing a hyperexcitability in a subject comprising detecting RNA foci which have a repeat expansion of UUUCA in a sample from the subject.

An aspect of the present disclosure relates to a method for treating a hyperexcitability in a subject comprising detecting RNA foci which have a repeat expansion of UUUCA in a sample from the subject, and if the RNA foci is detected, administering a pharmaceutical composition for treating the hyperexcitability to the subject.

In the above method, the sample may be a neuron. In the above method, the RNA foci may be in a nucleus of the neuron. In the above method, the hyperexcitability may be a hyperexcitability in the brain. In the above method, the hyperexcitability may be a hyperexcitability in the cerebrum. In the above method, the hyperexcitability may be a hyperexcitability of cortical neurons. In the above method, the hyperexcitability may be an epilepsy. The hyperexcitability may be a benign adult familial myoclonic epilepsy.

An aspect of the present disclosure relates to a kit for determining or diagnosing a hyperexcitability in a subject comprising a nucleic acid reagent configured to detect a repeat expansion of TTTCA, TTTTA, or a complementary sequence thereof in a nucleic acid sample from the subject.

In the above kit, the nucleic acid reagent may comprise a PCR primer configured to detect the repeat expansion of TTTCA, TTTTA, or the complementary sequence thereof. In the above kit, the PCR primer may comprise a complementary sequence of TTTCA, TTTTA, or a complementary sequence thereof. In the above kit, the nucleic acid reagent may comprise a hybridization probe configured to detect the repeat expansion of TTTCA, TTTTA, or the complementary sequence thereof. In the above kit, the hybridization probe may comprise a complementary sequence of TTTCA, TTTTA, or a complementary sequence thereof. In the above kit, the hybridization probe may comprise a complementary sequence of a neighboring sequence of TTTCA, TTTTA, or a complementary sequence thereof. In the above kit, the size of the neighboring sequence may be below 20 kb.

An aspect of the present disclosure relates to a kit for determining or diagnosing a hyperexcitability in a subject comprising a probe configured to detect a repeat expansion of UUUCA in a sample from the subject.

In the above kit, the probe may comprise TGAAA. In the above kit, the probe may be labeled with a fluorescent dye.

BRIEF DESCRIPTION OF DRAWINGS

FIG. 1

Refinement of a candidate region for BAFME. (a) Pedigree trees of BAFME families used for linkage analysis and haplotype analysis. Squares and circles indicate males and females, respectively. Affected individuals are indicated by filled symbols. A diagonal line through a symbol indicates a deceased individual. (b) Parametric linkage analysis revealing a single peak with a cumulative multipoint LOD score of 3.1. Candidate regions identified in previous studies are also shown. (c) Detailed haplotypes of the six families. A shared haplotype among the families is shown in gray (d) The minimum candidate region defined by the haplotype analysis. This includes a single exon (exon 4 of SAMD12) and the flanking introns.

FIG. 2a

Figure 2A:
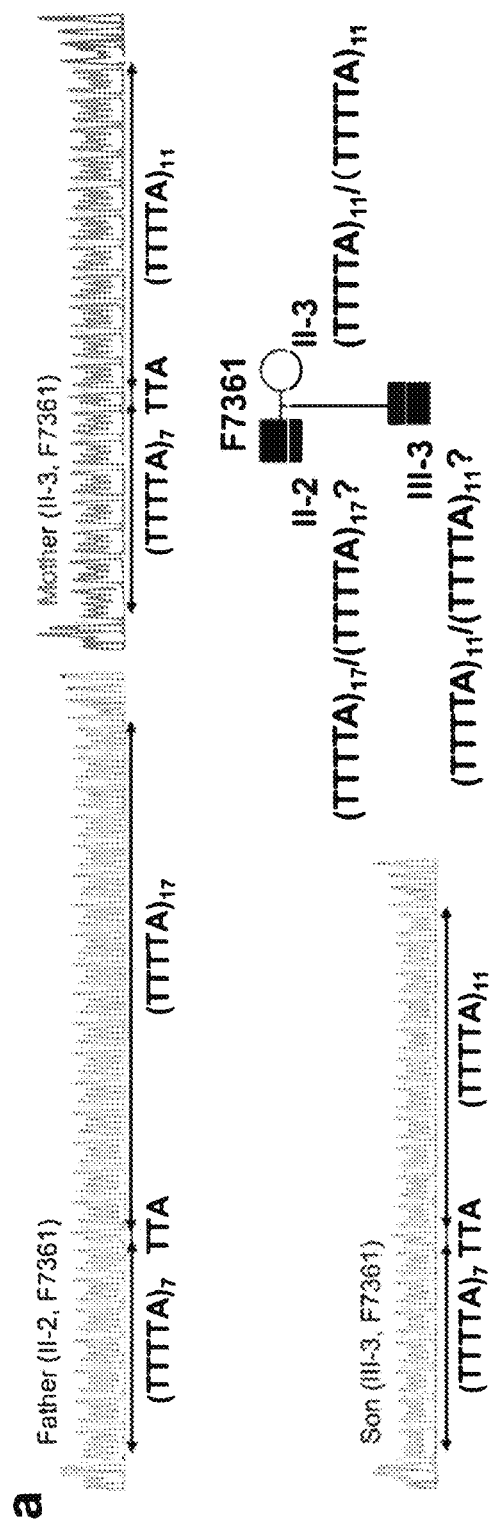

Identification of repeat expansion mutations in SAMD12. Sanger sequencing of the PCR products in intron 4 of SAMD12 in a trio (II-2, II-3, and III-3 in F7361) containing $(TTTTA)_7(TTA)(TTTTA)_{11 \text{ or } 17}$ (SEQ ID NO: 10). The numbers of the TTTTA repeat units located downstream of the TTA interruption are apparently 17/17 in the father, 11/11 in the mother, and 11/11 in the son, which is inconsistent with Mendel's law. FIG. 2a discloses SEQ ID NOS 36, 37, 37, 38, 38, 39, 39, 39, and 39, respectively, in order of appearance.

FIG. 2b

Figure 2B:
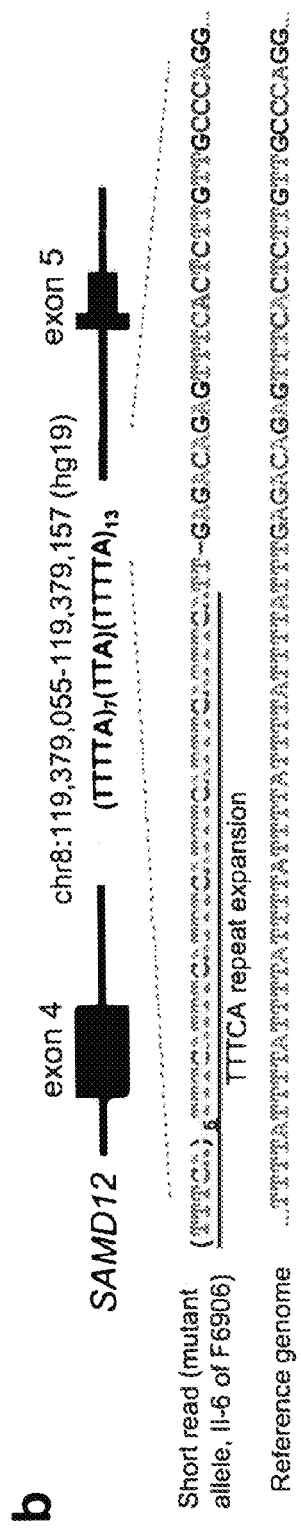

Identification of repeat expansion mutations in SAMD12. Manual alignment of short reads from the patient (II-6 in F6906) around the TTTTA repeat. Whereas the reference sequence of the repeat is $(TTTTA)_7(TTA)(TTTTA)_{13}$ (SEQ ID NO: 11) in the minus strand (chr8:119, 379, 055-119, 379, 157 in hg19), manual alignment of representative short reads reveals abnormal TTTCA repeat expansion in the downstream of the repeat. The other paired reads that are not shown in the Figure are uniquely aligned to this region, further supporting the presence of expanded TTTCA repeats. FIG. 2b discloses SEQ ID NOS 11, 40, and 41, respectively, in order of appearance.

FIG. 2c

Identification of repeat expansion mutations in SAMD12. Schematic representation of exon 4, intron 4, and exon 5 of SAMD12. The primer sets ("P1, P2, and P3 anchors" and "P3, P4, and P4 anchors") are designed to detect the expanded TTTTA and TTTCA repeats, respectively, assuming that TTTTA repeat expansion is located upstream of the TTTCA repeat expansion in intron 4 of SAMD12. Probes 1a and 1b are designed to contain sequences (FIG. 8) and used for Southern blot analysis.

FIG. 2d

Identification of repeat expansion mutations in SAMD12. Representative results of repeat-primed PCR analysis. Two independent experiments revealed similar results. In 82 patients from 48 families, both the TTTTA and TTTCA repeat expansions were demonstrated, similarly as shown in results for II-6 in F6906 (upper panel). In family F6115, repeat-primed PCR analysis showed only the TTTTA repeat expansion (middle panel). In controls, only short TTTTA repeats corresponding to those in the reference sequence are detected (lower panel).

FIG. 2e

Identification of repeat expansion mutations in SAMD12. Repeat expansions confirmed by Southern blot analysis. Using digoxigenin-labeled probes 1a and 1b, an affected individual (II-6 in F6906) showed an expanded allele, whereas an unaffected individual (II-7 in F6906) did not. Two independent experiments revealed similar results.

FIG. 2f

Identification of repeat expansion mutations in SAMD12. Southern blot analysis of F6115. Genomic DNAs were digested by SacI and subjected to Southern blot analysis using the digoxigenin-labeled probes 1a and 1b or digoxigenin-labeled $(TGAAA)_9$(SEQ ID NO: 17) (FIG. 8a). In affected individuals (I-2, II-1, and II-2 in F6115), the digoxigenin-labeled probes 1a and 1b revealed extra bands corresponding to expanded repeats in addition to the 2.3 kb bands derived from the normal allele (left panel). Southern blot analysis using digoxigenin-labeled $(TGAAA)_9$ (SEQ ID NO: 17) FIG. 8a and FIG. 8d) revealed that TTTCA repeats are contained in the expanded alleles (right panel) despite the fact that repeat-primed PCR targeting TTTCA failed as shown in FIG. 2d. This finding indicates that the expanded alleles in patients in F6115 have repeat configurations different from those in others including patients in F6906. The experiment was performed once.

FIG. 3a

Two repeat configurations of abnormal repeat expansions in SAMD12. Nucleotide sequences of BAC-cloned DNA fragments including the repeat expansions determined by SMRT sequencing. The analysis determined the exact repeat configurations in II-6 of F6906. In family F6115, in which the present inventors failed to detect TTTCA repeat expansions by repeat-primed PCR analysis, SMRT sequencing revealed TTTCA repeat expansions between two TTTTA repeat expansions. FIG. 3a discloses SEQ ID NOS 42-44, respectively, in order of appearance.

FIG. 3b

Figure 3B:
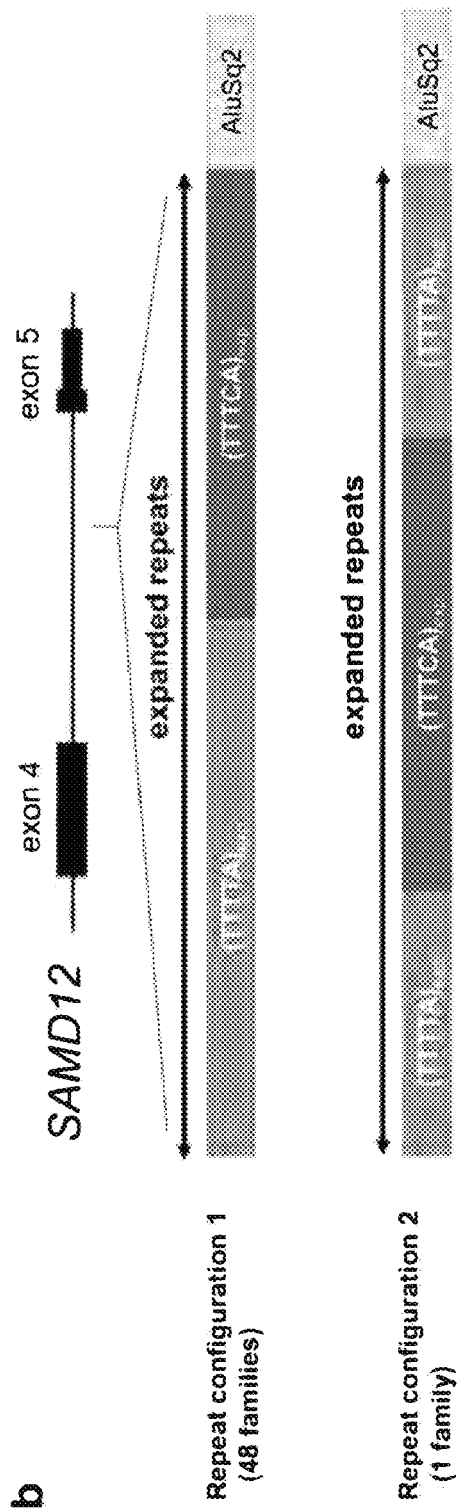

Two repeat configurations of abnormal repeat expansions in SAMD12. Schematic representation of repeat configurations in SAMD12 in BAFME1 families. Most families showed results compatible with repeat configuration 1, in which the TTTTA expansion is located upstream and the TTTCA expansion is located downstream. The present inventors found only one family (F6115) with repeat configuration 2, in which the TTTCA repeat expansion is located between two TTTTA repeat expansions. FIG. 3b discloses SEQ ID NOS 28-29, respectively, in order of appearance.

FIG. 4a

Repeat lengths inversely correlate with the age at onset of epilepsy and show intergenerational instabilities. The sizes of the expanded TTTCA and TTTTA repeats (repeat configuration 1) in SAMD12 estimated by Southern blot analysis and the ages at onset of epilepsy. Patients with heterozygous mutations whose genomic DNAs were extracted from peripheral blood leukocytes (50 patients) and lymphoblastoid cell lines (LCLs) (4 patients) are indicated by black circles and black squares, respectively. The data of expanded repeats in F6115 (repeat configuration 2) is not included in this analysis. The dotted line indicates a linear regression line for patients with heterozygous repeat expansions (n=54). The lengths of expanded repeats of patients with heterozygous repeat expansions inversely correlated significantly with the ages at onset of epilepsy (p=3.5×10−4, test for the significance of the correlation coefficient). It should be noted that the inverse correlation is still observed when the single outlier with the repeat length of 18.4 kb was omitted (p=8.9×10−4, test for the significance of the correlation coefficient). Of the four patients with homozygous mutations, the sizes of expanded repeats in peripheral blood leukocytes from the three patients are indicated by white circles, excluding an autopsied patient (V-3 in F8140) whose peripheral blood leukocytes or LCLs were unavailable. The ages at onset of epilepsy in patients with homozygous repeat expansions tended to be younger, as shown by the plots of their average repeat length against the age at onset of epilepsy, suggesting a possibility of an additive genetic effect on the age at onset in homozygous patients.

FIG. 4b

Repeat lengths inversely correlate with the age at onset of epilepsy and show intergenerational instabilities. A representative Southern blot analysis using genomic DNAs from peripheral leukocytes showing unstable repeat lengths across generations. In this family (F8398), the repeat expansions are larger in the successive generations. The experiment was performed once.

FIG. 5

Neuropathological study of BAFME1 patients. (a-d) Histopathologic features of the brains of autopsied patients with BAFME with TTTCA pentanucleotide repeat expansions (repeat configuration 1) in SAMD12. Cerebellar cortex of the patient with homozygous mutations (a-c: V-3 in F8140) and that of a patient with heterozygous mutations (d: II-7 in F8138). (a) A residual Purkinje cell showing halo-like amorphous materials around the cell body (somatic sprouts) and a deformed nucleus. (b) Another example of a Purkinje cell with somatic sprouts, demonstrated by silver impregnation. (c) The halo-like amorphous materials of two Purkinje cells are immunopositive for calbindin protein D-28k. The experiments were performed six times with similar, reliable results. (d) Three Purkinje cells without somatic sprouts. (a, d) Hematoxylin and eosin stain, (b) Bodian stain, and (c) immunostained and then counterstained with hematoxylin. Bar=25 μm for a, b and d, and 50 μm for c. (e) Fluorescence in situ hybridization analysis revealing RNA foci in large cortical neurons in the autopsied brains of patients with TTTCA pentanucleotide repeat expansions (repeat configuration 1) in SAMD12. Because RNA foci were observed when using a Cy3-labeled $(TGAAA)_{12}$ probe (SEQ ID NO: 13), RNA foci are considered to consist of UUUCA repeats. Similar results were obtained in other four heterozygous patients and three controls. No RNA foci were detected in the affected brains using the antisense Cy3-$(TTTCA)_{12}$ probe (SEQ ID NO: 14). RNase A pretreatment produced no fluorescent signals in affected brains, while fluorescent signals remained with DNase I pretreatment (data not shown). The present inventors did not observe RNA-foci using Cy3-$(TAAAA)_{12}$ (SEQ ID NO: 15) or Cy3-$(TAAAA)$ is probe (SEQ ID NO: 16) targeting UUUUA repeat expansion. FIG. 5e discloses SEQ ID NOS 14 and 18, respectively, in order of appearance.

FIG. 6a

Figure 6A:
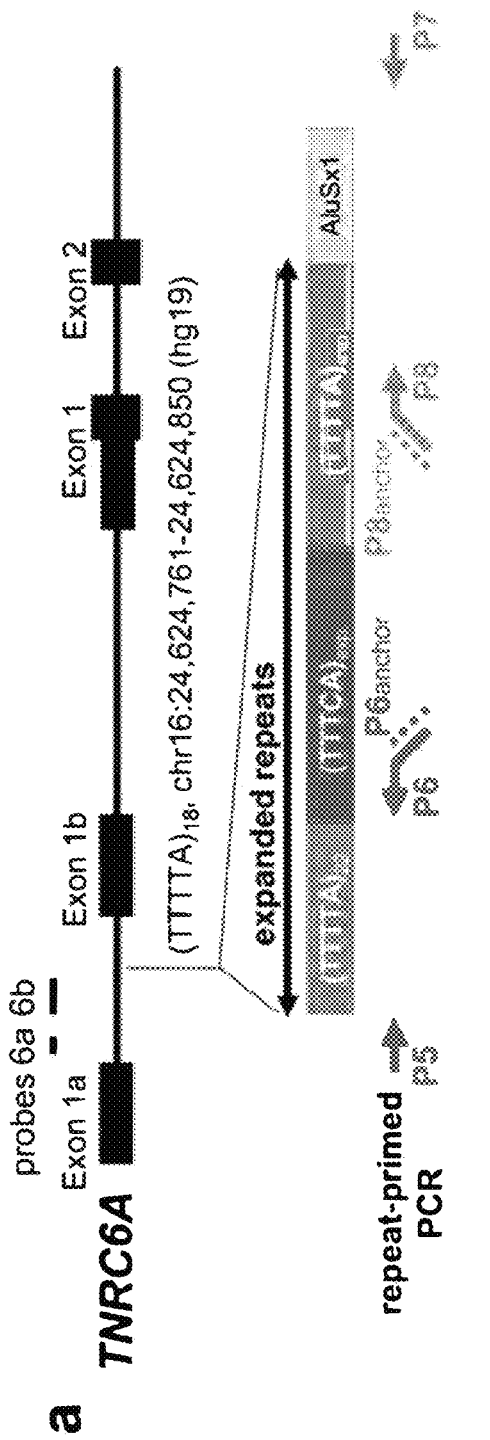

Identification of TTTCA and TTTTA repeat expansion mutations in TNRC6A (BAFME6) and RAPGEF2 (BAFME7). Schematic representation of repeat expansion mutations in TNRC6A. The primer sets "P5, P6, and P6 anchors" and "P7, P8, and P8 anchors" designed to detect the TTTCA and TTTTA repeat expansions, respectively, are shown beneath the schematic diagram of the expanded repeats. Probes 6a and 6b are designed to contain sequences (FIG. 8b) and used for Southern blot analysis. FIG. 6a discloses SEQ ID NOS 19 and 30, respectively, in order of appearance.

FIG. 6b

Identification of TTTCA and TTTTA repeat expansion mutations in TNRC6A (BAFME6) and RAPGEF2 (BAFME7). Representative results of repeat-primed PCR analysis. The figure shows the existence of TTTTA and TTTCA repeat expansions in a patient (upper panel). In all the five affected individuals in F9283, both TTTTA and TTTCA repeat expansions are detected. The experiments were independently performed twice with similar results.

FIG. 6c

Identification of TTTCA and TTTTA repeat expansion mutations in TNRC6A (BAFME6) and RAPGEF2 (BAFME7). Southern blot analysis of F9283. Using digoxigenin-labeled probes 6a and 6b, Southern blot analysis revealed 10 kb bands that corresponds to expanded alleles (arrow) in the affected individuals (left panel). The experiments were independently performed twice with similar results. Southern blot analysis using the digoxigenin-labeled $(TGAAA)_9$ (SEQ ID NO: 17) probe shows that the expanded alleles (arrow) in the affected individuals contain TTTCA repeat expansions (right panel). The lengths of the expanded repeats in TNRC6A are less unstable than those in SAMD12. The experiment was performed once.

FIG. 6d

Figure 6D:
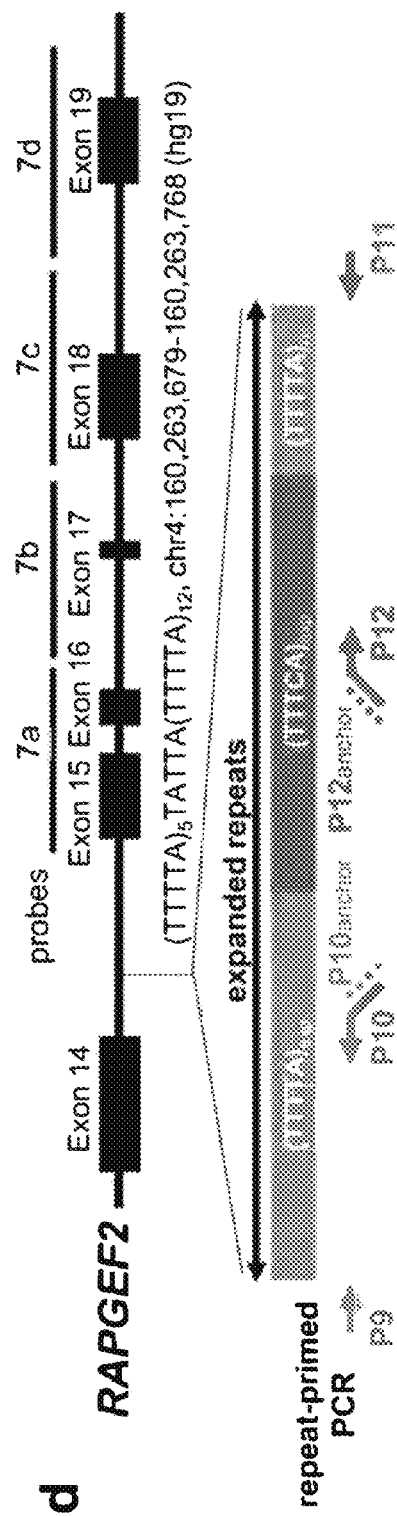

Identification of TTTCA and TTTTA repeat expansion mutations in TNRC6A (BAFME6) and RAPGEF2 (BAFME7). Schematic representation of abnormal repeat expansion in RAPGEF2. The primer sets "P9, P10, and P10 anchors" and "P11. P12, and P12 anchors" designed to detect the TTTTA and TTTCA repeat expansions, respectively, are shown beneath the schematic diagram of the expanded repeats. Probes 7a-d are designed to contain sequences (FIG. 8c) and used for Southern blot analysis. FIG. 6d discloses SEQ ID NOS 45 and 31, respectively, in order of appearance.

FIG. 6e

Identification of TTTCA and TTTTA repeat expansion mutations in TNRC6A (BAFME6) and RAPGEF2 (BAFME7). Results of repeat-primed PCR analysis of F8241. The figure shows the existence of both TTTTA and TT TCA repeat expansions in III-2 (upper panel). In the unaffected sibling (III-1), the TTTTA repeat expansion was detected, while the TTTCA repeat expansion was not (middle panel). In the mother (II-2), only a normal, short TTTTA repeat is detected (lower panel). The experiments were independently performed twice with similar results.

FIG. 6f

Identification of TTTCA and TTTTA repeat expansion mutations in TNRC6A (BAFME6) and RAPGEF2 (BAFME7). Southern blot analysis of F8241. Using digoxigenin-labeled probes 7a-d, Southern blot analysis (left panel) revealed a 20 kb band corresponding to the expanded allele (arrow) in the affected patient (III-2). Southern blot analysis using the digoxigenin-labeled $(TGAAA)_9$ probe (SEQ ID NO: 17) (right panel) shows that the expanded allele (arrow) in the affected patient (III-2) contains TTTCA repeat expansions. In an unaffected sibling (III-1), a 10.1 kb band corresponding to a short expansion is observed in addition to an 8.9 kb band corresponding to the normal allele. Southern blot analysis using the digoxigenin-labeled (TGAAA)$_9$ probe (SEQ ID NO: 17) (right panel), however, did not reveal the 10.1 kb band, indicating that the short expansion in III-1 does not contain the TTTCA repeat expansion. These experiments were independently performed twice with similar results.

FIG. 7

Short read aligned to upstream region of repeat in SAMD12 showing TTTTA repeat expansion. Top: Results of whole-genome sequence analysis of two affected individuals suggest mutant alleles containing TTTTA repeat expansion in the upstream region. Bottom: Results of whole-genome sequence analysis of an affected individual suggest TTTCA repeat expansion in the downstream region. The bottom diagram is the same as that in FIG. 2b. FIG. 7 discloses SEQ ID NOS 46-48, 11, 49, and 41, respectively, in order of appearance.

FIG. 8

Schematic representations of the positions of the repeat, the probes used for Southern blot analysis, and the restriction sites. (a-c). Schematic representations of probes used in the study. Physical positions are based on hg19. Digoxigenin (DIG)-labeled probe synthesis are performed using PCR, with subcloned genomic fragments prepared for templates. Primers used for probe synthesis are listed in FIG. 27. When indicated, multiple probes were mixed in hybridization buffer (Roche DIG Easy-Hyb) to increase hybridization signals. (d) A schematic representation of (TGAAA)$_9$ probes (SEQ ID NO: 12). DIG-labeled probes made from genomic fragments are hybridized to both normal and expanded alleles, whereas DIG-(TGAAA)$_9$ probe (SEQ ID NO: 17) is hybridized exclusively to expanded alleles containing TTTCA repeat expansions. FIG. 8d discloses SEQ ID NOS 17 and 28, respectively, in order of appearance.

FIG. 9

Families with repeat expansion mutations in SAMD12 (repeat configuration 1). Affected individuals are indicated by filled symbols. A diagonal line through a symbol indicates a deceased individual. Symbols with red dots represents individuals whose genomic DNA samples were available.

FIG. 10

Disease haplotypes of families with repeat configurations 1 and 2 in SAMD12. Haplotypes were determined by SNPtyping, sequencing of BAC clones using PacBio RSII, and sequencing of genomic DNAs using 10× GemCode technology. Between rs3900767 and rs62533397, all the sequence variants matched except the repeat expansion mutations. Thus, it is likely that a common founder was present and one configuration derived from another configuration.

FIG. 11

Dot plot of assembled Nanopore reads indicating the repeat expansion. Dot plots between the assembled contig with the STR expansion for each of the two samples (X-axis) and its corresponding hg19 region surrounding the STR site (chr8:119, 379, 052-119, 379, 172) without an expansion (Y-axis). Below the X-axis, the interleaved patterns of four colors show genomic sequence compositions, the red bars represent STR expansions in the two samples, and the respective red and blue-colored bars show nanopore read alignments in the plus and minus strands. Raw nanopore reads with STR expansions were aligned to the assembled contigs in the x-axis, supporting the presence of the STR expansions. In contrast, reads without STR expansions were aligned with the hg19 reference genome in the y-axis. These alignments are shown to the right of the y-axis, indicating the heterozygosity of the STR expansions. (a) II-6 in F6906 (repeat configuration 1 in SAMD12). (b) II-1 in F6115 (repeat configuration 2 in SAMD12).

FIG. 12

Nanopore reads indicating the repeat expansion in SAMD12 using 1D2 technology. Raw Nanopore 1D2 reads of repeat configuration 1 (II-6 in F6906, a) and repeat configuration 2 (II-1 in F6115, d) of SAMD12 are shown. The number of TTTCA and TTTTA motifs counted using Tandem Repeat. Finder (Version4.09) are shown in (b) and (e), respectively. Care has to be taken to interpret these numbers of motifs because they may still include errors. The match ratios between observed read and estimated pure repeats are around 90% (c and f, respectively). FIG. 12 discloses SEQ ID NOS 50, 32, 51, and 33, respectively, in order of appearance.

FIG. 13

Somatic instability of the repeat expansion in SAMD12 in various tissues/cells. All the experiments were performed after SacI digestion of genomic DNA and hybridization was performed using probes 1a and 1b. (a) Lengths of the repeat expansion of leukocytes and those of lymphoblastoid cell lines, which were comparable. (b-d) Length of the repeat expansions in various part of the brains and other tissues. II-5 of F8138, II-3 of F8135, II-7 of F8138, and II-5 of F8136 show smear patterns, whereas a homozygous patient (V-3 of F8140) shows rather discrete bands. Genomic DNAs from cerebellum tend to show less somatic instability. The experiment was performed once. Hetero, heterozygote; homo, homozygote; LCL, lymphoblastoid cell line; NC, non-carrier.

FIG. 14

Intergenerational instability of repeat lengths in SAMD12. (a) Intergenerational instability in parent-offspring pairs. The average increase in the lengths of expanded repeats observed in parent-offspring pairs (n=20) was +0.89 kb (95% confidence interval, +0.12–+1.48 kb). (b) Intergenerational instability of repeat lengths in father-offspring pairs and mother-offspring pairs. Expansions tended to be larger in maternal transmissions (n=11) (+1.2 kb, 95% confidence interval, −0.03–+2.5 kb) than in paternal transmission (n=9) (+0.28 kb, 95% confidence interval, −0.38–+0.94 kb), although the difference was not statistically significant (p=0.29, two-tailed Wilcoxon rank sum test).

FIG. 15

RNA foci observed in cerebella of patients carrying expanded repeats in homozygous or heterozygous state. Fluorescent in situ hybridization (FISH) analysis using oligonucleotides (Cy3-(TGAAA)$_{12}$ (SEQ ID NO: 18) and Cy3-(TTTCA)$_{12}$ (SEQ ID NO: 14)) revealed RNA foci in cerebella of the patients carrying expanded repeats in the homozygous or heterozygous state, whereas no RNA foci were observed in the control cerebellum. The experiments were performed twice with similar results.

FIG. 16

Abortive transcription in the brain was suggested by RNA-seq analysis. (a-c) Aligned short reads visualized using Integrative Genomic Viewer. Schematic representations of SAMD12 transcripts are shown above. In homozygous (one patient) and heterozygous patients (two representative patients), read coverages increased in the region upstream of the expanded repeats (region 1) compared with those of the region downstream of the expanded repeats (region 2). This increase is presumably due to the abortive transcription at the expanded repeats. No such increase occurred in the liver (b) and lymphoblastoid cell lines (c) of the patients. Similar results were independently obtained in six BAFME1 brains, eight control brains, six BAFME1 lymphoblastoid cell lines, two control cell lines, and three BAFME1 livers. (d) Quantification of average read coverages of regions 1 and 2. The read coverage ratios of brains of a homozygous BAFME1 patient (n=1), heterozygous BAFME1 patients (n=5), and controls (n=8), those of lymphoblastoid cell lines of homozygous BAFME1 patients (n=2), heterozygous BAFME1 patients (n=4), and unaffected family members (n=2), and those of livers of a homozygous patient (n=1) and heterozygous BAFME1 patients (n=2) are shown. All the patients have repeat expansion mutations in SAMD12 (repeat configuration 1). The lines in the figure indicate the mean of the ratios. Wilcoxon's rank sum test was used for statistical analysis. "*" indicates that there is a significant difference (p<0.05). (e) A model of abortive transcription. An increase in the read coverage ratio of region 1 compared with that of region 2, observed only in the affected brain, was supposed to be caused by abortive transcription due to abnormal repeat expansions (Ameur et al. Nat. Struct. Mol. Biol. 18, 1435-1440 (2011)). E1-4 indicates exons 1-4. (f) Expression levels of SAMD12 transcript 1 in the brain (heterozygous BAFME1 patients (n=4) and controls (n=5)) determined by qRT-PCR analysis, using primers on exon 4/5 junctions and exon 5. The expression level of RPL13A was used as the endogeneous control. The data are shown as means and standard errors of the mean. The expression level of SAMD12 transcript 1 was not altered in the affected brain (two-tailed Student's t-test) even when abortive transcription products are present. Note that the exact quantification of SAMD12 transcript 2 is difficult in the presence of abortive transcription products. Homo, homozygous; hetero, heterozygous; LCL, lymphoblastoid cell line; n.s., not significant.

FIG. 17

Expression levels of SAMD12 protein in brains. (a) The upper panel is the image of western blot of SAMD12 protein (isoform 1) of BAFME1 brains (occipital lobe, a homozygous patient (n=1) and heterozygous patients (n=5)) and controls (occipital lobe, n=5). The lower panel is the image of western blot of β-actin. (b) The graphic representation of the relative expression of SAMD12 protein (isoform 1) with respect to β-actin expression in each brain. (c) The bar graph of relative expression levels of SAMD12 isoform 1 (a homozygous patient (n=1), heterozygous patients (n=5), and controls (n=5)). The expression levels of SAMD12 isoform 1 in brains of patients with heterozygous repeat expansions were lower than those of the control brains (two-tailed t-test, p=0.0074, 95% confidence interval, 0.59-1.57 vs. 1.59-2.58). The data are shown as means and standard errors of the mean. "*" indicates that there is a significant difference (p<0.05). The experiment was independently repeated twice with similar results.

FIG. 18

TTTCA repeat expansions are identified in TNRC6A and RAPGEF2 in F9283 and F8241, respectively. One family (F9283) had a TTTCA repeat expansion mutation in TNRC6A, whereas the other family (F8241) had a TTTCA repeat expansion mutation in RAPGEF2.

FIG. 19

TTTCA and TTTTA repeat expansion in TNRC6A. Manual alignment of short reads revealed that the mutant allele consists of expanded TTTCA repeats between the short. (22) and expanded TTTTA repeats. There is (TTTTA)18 (SEQ ID NO: 19) in the reference genome sequence (chr16:24, 624, 761-24, 624, 850 in hg19). FIG. 19 discloses SEQ ID NOS 52, 53, 30, 54, and 55, respectively, in order of appearance.

FIG. 20

Localization of expanded TTTCA repeats in TNRC6A. The repeat expansion was identified in the upstream region of exon 1 of TNRC6A registered in the RefSeq database. Brain RNA-seq data indicate that there are spliced transcripts flanking the repeat, which is also registered as spliced EST (HY329817). (a) The transcript is further confirmed to be expressed in the brain, placenta, kidney, and pancreas by RT-PCR analysis. (b) These findings indicate that the expanded repeats are located in an intron (designated as intron 1a) of a transcript of TNRC6A expressed in the brain. The experiment was performed twice with similar results.

FIG. 21

Parametric linkage analysis of BAFME6 family. Parametric linkage analysis of all chromosomes (a) and known loci of BAFME (b). The double-headed arrows indicate the known candidate regions. The analysis excludes other loci of BAFME1, BAFME2, BAFME3, and BAFME4.

FIG. 22

TTTCA and TTTTA repeat expansion in RAPGEF2. Manual alignment of short reads revealed that the mutant allele consists of expanded TTTCA repeats between the expanded and short (designated as "n") TTTTA repeats. There is (TTTTA)$_5$(TATTA)(TTTTA)$_{12}$ (SEQ ID NO: 20) in the reference genome sequence (chr4:160, 263, 679-160, 263, 768 in hg19). FIG. 22 discloses SEQ ID NOS 56-58, 29, 59, and 60, respectively, in order of appearance.

FIG. 23

Haplotype analysis of F8241. (a) Haplotype analysis suggests that III-1 and III-2 in F8241 have the same paternal allele. This is also confirmed by dense SNP data analysis (data not shown).

FIG. 23a discloses SEQ ID NOS 61, 62, 61, 63, and 62, respectively, in order of appearance. (b) The expanded repeat of the proband (III-2) shows a massive expansion (>20 kb) and somatic instability. The expanded allele of the unaffected sister consists only of TTTTA repeat, raising the possibility that the expanded TTTCA repeats could have been deleted when transmitted from the father, who also had tremulous movements in his hands. FIG. 23b discloses SEQ ID NOS 29 and 29, respectively, in order of appearance.

FIG. 24

Primers used for analysis of microsatellites. FIG. 24 discloses SEQ ID NOS 64-68, 66, 69, 70, 66, 71, 72, 66, 73, 74, 66, 75, 76, 66, 77, 78, 66, 79, 80, 66, 81, 82, 66, 83, 84, 66, 85, 86, and 66, respectively, in order of appearance.

FIG. 25

Primer list used for repeat-primed PCR analysis. FIG. 25 discloses SEQ ID NOS 87-91, 89, 92-96, 94, 97-98, 94, 99, 100, and 94, respectively, in order of appearance.

FIG. 26

Number of reads filled with 5'-TTTCA/5'-TGAAA, 5'-CTTCA/5'-TGAAG, and 5'-GTTCA/5'-TGAAC motifs in RNA-seq and whole-genome sequence analyses.

FIG. 27

The number of reads containing various repeat motifs shown by whole-genome sequence analysis using TRhist. In the probands of F9283 and F8241, large numbers of reads containing 5'-AAATG (equivalent to 5'-TTTCA in the opposite strand) were similarly observed as in the two BAFME patients with TTTTCA repeat expansions in SAMD12 (F8135 and F8140). Neither AAATG (=TTTCA), AACTG (=GTTCA), nor AAGTG (=CTTCA) repeat expansions were observed in the seven controls. FIG. 27 discloses SEQ ID NOS 101-103, respectively, in order of appearance.

FIG. 28

TTTCA/TGAAA or TTTTA/TAAAA repeats in the reference sequence (hg19). (a) The number of $(TTTCA)_{>9}/(TGAAA)_{>9}$ or $(TTTTA)_{>9}/(TAAAA)_{>9}$ repeat in the reference sequence (hg19) are shown. Of these, those located in the candidate regions of BAFME2, BAMFE3, and BAFME4 and those located in introns are shown. (b) The longest intronic TTTTA/TAAAA or TTTCA/TGAAA repeats in the reference sequence. (c) $(TTTCA)_{>9}/(TGAAA)_{>9}$ or $(TTTTA)_{>9}/(TAAAA)_{>9}$ repeat located in introns of the candidate regions of BAFME were shown. FIG. 28 discloses SEQ ID NOS 104, 104-109, and 108, respectively, in order of appearance.

FIG. 29

Primers used for generation of digoxigenin-labeled probes used in Southern blot hybridization analysis. FIG. 29 discloses SEQ ID NOS 110-125, respectively, in order of appearance.

FIG. 30

Primer sequences used for BAC cloning. FIG. 30 discloses SEQ ID NOS 126-129, respectively, in order of appearance.

FIG. 31

The ages at death and the causes of death of autopsied patients.

FIG. 32

Primer sequences used for RT-PCR. FIG. 32 discloses SEQ ID NOS 130-135, respectively, in order of appearance.

FIG. 33

RNA-seq analysis of four heterozygous BAFME patients with repeat expansion mutations in SAMD12 and eight control subjects. All the data are calculated by Cufflinks, Cuffquant, and Cuffdiff (v2.2.1) with default settings (Trapnell, C. et al. Nat. Biotechnol. 28, 511-515 (2010)).

DESCRIPTION OF EMBODIMENTS

Epilepsy is a common neurological disorder, in which mutations in ion channels or neurotransmitter receptors are the frequent causes of monogenic forms of epilepsy. As described in the below examples, the present inventors found that abnormal TTTCA and TTTTA repeat expansions in intron 4 of SAMD12 cause benign adult familial myoclonic epilepsy (BAFME). Single-molecule, real-time sequencing of BAC clones and nanopore sequencing of genomic DNAs revealed two repeat configurations in SAMD12. Intriguingly, in the two families with the clinical diagnosis of BAFME where no repeat expansions in SAMD12 were observed, similar TTTCA and TTTTA repeat expansions were further identified in introns of TNRC6A and RAPGEF2, indicating that expansions of the same repeat motifs are involved in the pathogenesis of hyperexcitability including BAFME regardless of the genes where the expanded repeats are located. These findings that noncoding repeat expansions lead to neuronal dysfunction responsible for myoclonic tremor and epilepsy further expand our scope of understanding of noncoding repeat expansion diseases.

As described in the below examples, the present inventors found two configurations of TTTCA and TTTTA repeat expansions in SAMD12 as the cause of BAFME (designated as BAFME1). The repeat expansions of either of the two repeat configurations were confirmed in 49 of the 51 families, indicating that BAFME1 is by far the most common form among various forms of BAFME. Nanopore sequencing of genomic DNAs revealed that the expanded TTTTA repeats are comparable to the expanded TTTCA repeats in length, indicating the necessity of investigating how TTTCA and TTTTA repeat expansions are involved in the pathogenesis of BAFME.

The present inventors furthermore found TTTCA and TTTTA repeat expansions in TNRC6A (designated as BAFME6) and RAPGEF2 (designated as BAFME7) in the two BAFME families where repeat expansions in SAMD12 were excluded. The gene products of SAMD12, TNRC6A, and RAPGEF2 are expressed in the brain. The repeat sequences of these genes in the reference genome consist of short stretches of mainly TTTTA repeats, two of which are located at poly A tails of Alu sequences.

While no TTTCA repeat expansions in SAMD12, TNRC6A, and RAPGEF2 were found in control subjects, the RP-PCR analysis targeting TTTTA repeats in the three loci revealed that 5.9%, 0.9%, and 0.5% of the control subjects carry TTTTA repeat expansions in SAMD12, TNRC6A, and RAPGEF2, respectively. The presence of TTTTA repeats ranging from 0.2-3 kb to even larger sizes in the control subjects suggests that expanded TTTTA repeats are unlikely to contribute to the disease. Similar phenomenon has also been described in SCA31.

Western blot analysis showed that SAMD12 protein levels were slightly but significantly decreased in the brains with expanded repeats in SAMD12, raising the possibility that decreased SAMD12 protein levels contribute to the disease. The finding that identical expanded repeat motifs have been identified in separate genes, however, strongly argue for that the expression of RNA molecules containing UUUCA and UUUUA repeat expansions per se are involved in the pathogenesis of BAFME rather than the altered physiological functions of each individual gene. As described above, expansions of TTTTA repeats are also observed in a limited proportion of control subjects, supporting that expanded TTTCA repeats are primarily involved in the pathogenesis of BAFME. Presence of RNA foci with UUUCA repeats but not with UUUUA repeats in nuclei of neuronal cells in autopsied brains with expanded repeats in SAMD12 further support this notion. RNA foci have been observed in several neurodegenerative disorders with noncoding repeat expansions and considered to be a hallmark neuropathological finding in them. Although it remains to be elucidated how UUUCA repeats were preferentially included in the RNA foci, these lines of evidence strongly suggest that RNA-mediated toxicity, in particular, expanded UUUCA repeat-mediated toxicity, is the mechanism underlying the pathogenesis of BAFME.

Epilepsy is a common neurological disorder in which familial occurrence is not infrequent. In contrast to the previous findings that mutations in ion channels or neurotransmitter receptors are the causes of monogenic forms of epilepsy, the present inventor's findings highlight the role of noncoding repeat expansions in epilepsy. Of note, clinical observations revealed only an extremely slow progression of myoclonic tremor of the hands over decades, and neuropathological examinations revealed mild loss of Purkinje cells only in the patient with homozygous mutations, while such changes are inconspicuous in the patients with heterozygous mutations, and otherwise, there were no evident alterations in other regions of the central nervous system in the patients with either homozygous or heterozygous mutations. These findings are in a striking contrast to other diseases caused by noncoding repeat expansions, suggesting that the main disease mechanism in BAFME is a functional impairment leading to hyperexcitability of cortical neurons. Close clinical observations on BAFME patients, however, indicate that cortical tremor in the hands slowly progresses and the amplitude of somatosensory evoked potentials gets bigger over decades, raising the possibility that the epilepsy could be due to neurodegeneration, resultant disruption of the neural network, and/or disturbance of proteins key to maintaining proper electrophysiological network.

The present inventors found accumulation of altered repeat motifs in the RNA-seq data of affected brains. Intriguingly, CUUCA and GUUCA repeats were not observed in those from LCLs or livers from the patients. In contrast, the present inventors only observed trace amounts of sequences filled with CTTCA and/or GTTCA repeats in the whole genome sequence data from the three autopsied patients (FIG. 26b). The CUUCA and/or GUUCA repeats were observed only in affected brains, supporting the interpretation that the CUUCA and GUUCA repeat sequences are derived from the mutant alleles of SAMD12. The findings raise the possibility of RNA editing, but other mechanisms are also conceivable. Although the exact mechanisms leading to altered RNA sequences need to be further investigated, these findings should be taken into account in investigating disease mechanisms of noncoding repeat expansion diseases. The present inventors need to consider broader ranges of RNA-binding proteins including those specific to CUUUA or GUUCA repeats in addition to those specific to UUUCA and UUUUA repeats. The present inventors might also need to consider broader ranges of repeat-associated non-ATG translated proteins including poly-(LHFTS) (SEQ ID NO: 21), poly-(VQFSS) (SEQ ID NO: 22), poly-(FYFIL) (SEQ ID NO: 23), and poly-(FHFIS) (SEQ ID NO: 24), predicted from CUUCA, GUUCA, UUUUA, and UUUCA repeats, respectively.

Detection of noncoding repeat expansions is difficult by short-read sequencers. The present inventors previously developed a method, direct identification of repeat expansion and cloning technique (DIRECT), to directly identify expanded CAG repeats using probes specifically designed for hybridization with expanded CAG repeats and cloned the gene for SCA2. Here, the present inventors have devised an in silico version of DIRECT for direct identification of expanded repeat motifs using paired-end reads obtained by whole-genome sequencing. This strategy enabled us to discover the TTTCA and TTTTA repeat expansions in TNRC6A and RAPGEF2. The present inventors believe this strategy will accelerate the search for noncoding repeat expansions in broad ranges of neurological diseases. Furthermore, the discovery of identical expanded repeat motifs derived from three independent genes emphasizes the possibility that additional genes may well be involved even for diseases previously identified to be caused by noncoding repeat expansions. In particular, whereas no TTTCA repeat with more than 9 repeat units are registered in the reference sequence (hg19) in the candidate regions of BAFME2 (2q), BAFME3 (5p), and BAFME4 (3q), TTTTA repeats in intron 1 of STARD7 located in the candidate region of BAFME2 and TTTTA repeats in intron 1 of MARCH6 and in intron 34 of TRIO located in the candidate region of BAFME3 are potentially good candidates for these diseases (FIG. 28).

The present inventors found that the noncoding TTTCA repeat expansions in SAMD12, TNRC6A, and RAPGEF2 cause BAFME, which should expand our insights into the molecular bases of epilepsies and lead to the development of efficacious therapeutic measures for hyperexcitability including BAFME based on the elucidated molecular mechanisms of the diseases. The present inventors expect the present invention will further accelerate discovery of other diseases caused by noncoding repeat expansions.

Based on the above findings by the present inventors, a method for determining or diagnosing a hyperexcitability in a subject according to the embodiment of the present invention comprises detecting a repeat expansion of TTTCA, TTTTA, or a complementary sequence thereof in a nucleic acid sample from the subject. The presence of the repeat expansion in the nucleic acid sample indicates that the subject has the hyperexcitability or is at risk of having the hyperexcitability. The method can be used for determining whether the subject has or is at risk of having the hyperexcitability.

The hyperexcitability may be a hyperexcitability in the brain, a hyperexcitability in the cerebrum, a hyperexcitability of cortical neurons, an epilepsy, or a benign adult familial myoclonic epilepsy (BAFME).

The subject is a human being or a non-human animal. The subject may be a patient who may have the hyperexcitability. The nucleic acid sample may be collected from the subject prior to the detection of the repeat expansion. The method may be carried out in vivo. The nucleic acid sample may be DNA, such as chromosome DNA, or alternatively, the nucleic acid sample may be RNA.

The TTTCA repeat expansion may be greater than 50 repeats, 100 repeats, greater than 150 repeats, greater than 200 repeats, greater than 250 repeats, greater than 300 repeats, greater than 350 repeats, or greater than 400 repeats.

The size of the expanded TTTCA may be greater than 150 base pairs, 500 base pairs, greater than 750 base pairs, greater than 1,000 base pairs, greater than 1,250 base pairs, greater than 1,500 base pairs, greater than 1,750 base pairs, or greater than 2,000 base pairs.

The size of the expanded TTTTA may be greater than 500 base pairs, greater than 750 base pairs, greater than 1,000 base pairs, greater than 1,250 base pairs, greater than 1,500 base pairs, greater than 1,750 base pairs, or greater than 2,000 base pairs.

The TTCA and TTTTA may be in an intron of any gene from the subject. The gene may be at least one of SAMD12 gene, TNRC6A gene, and RAPGEF2 gene, for example.

The method for determining or diagnosing the hyperexcitability in the subject according to the embodiment may further comprise calculating an anticipated age at onset of the hyperexcitability based on the size of the repeat expansion.

The present inventors found that the size of the repeat expansion, including the repeat lengths, inversely correlates with the ages at onset of the hyperexcitability. Therefore, for example, by using an equation expressing the inverse correlation between the size of the repeat expansion and the ages at onset of the hyperexcitability, it is possible to calculate the anticipated age at onset of the hyperexcitability based on the size of the detected repeat expansion.

A kit for determining or diagnosing a hyperexcitability in a subject according to the embodiment of the present invention comprises a nucleic acid reagent configured to detect the repeat expansion of TTTCA, TTTTA, or the complementary sequence thereof in the nucleic acid sample from the subject.

The kit can be used for the method for determining or diagnosing the hyperexcitability in the subject according to the embodiment of the present invention. The kit may be used in vivo.

The nucleic acid reagent may comprise a PCR primer configured to detect the repeat expansion of TTTCA, TTTTA, or the complementary sequence thereof. The PCR primer may comprise a complementary sequence of TTTCA, TTTTA, or a complementary sequence thereof.

The PCR may be a repeat-primed PCR and a long-range PCR. The repeat-primed PCR and the long-range PCR can detect the repeat expansion. An application on the repeat-primed PCR is described in Neuron 72, 257-268, Oct. 20, 2011. In the repeat-primed PCR, nucleic acids are amplified between a forward primer and a reverse primer at an initial stage. Since the concentration of the forward primer is low, the forward primer is wasted. Thereafter, the nucleic acids are amplified between an anchor primer and the reverse primer. If the anchor primer does not present, a repeat sequence is randomly annealed. In such case, only short PCR products are produced, and it is difficult to detect a repeat expansion. If the anchor primer presents, PCR products are produced between the anchor primer and the reverse primer so that they reflect the distribution of PCR products produced at the initial stage by the annealing of the forward primer. A comb-like distribution of the PCR product can be obtained. It should be noted that the anchor primer is not limited to any specific sequence.

Alternatively, the nucleic acid reagent in the kit may comprise a hybridization probe configured to detect the repeat expansion of TTTCA, TTTTA, or the complementary sequence thereof. The hybridization probe can be used for a southern blotting, for example. The southern blotting can detect the repeat expansion. The hybridization probe is configured to detect fragmented nucleic acids that contain the expanded repeat sequence. The fragmented nucleic acids are prepared by using a restriction enzyme. The restriction enzyme is appropriately selected. A restriction site neighboring the expanded repeat sequence is preferably selected. The size of the fragmented nucleic acids prepared by the restriction enzyme may be less than 20 kb, less than 10 kb, or less than 5 kb.

The hybridization probe may comprise a complementary sequence of TTTCA, TTTTA, or a complementary sequence thereof. The hybridization probe may comprise a complementary sequence of a genome sequence around the expanded repeat sequence. The hybridization probe may comprise a complementary sequence of a neighboring sequence of TTTCA, TTTTA, or a complementary sequence thereof. The size of the neighboring sequence may be below 20 kb, below 10 kb, or below 5 kb. The hybridization probe may comprise a complementary sequence of a genome sequence of a partial sequence of the fragmented nucleic acids that contain the expanded repeat sequence.

A method for determining or diagnosing the hyperexcitability in the subject according to the embodiment of the present invention comprises detecting RNA foci which have a repeat expansion of UUUCA in a sample from the subject. The presence of the RNA foci which have the repeat expansion of UUUCA in the sample indicates that the subject has the hyperexcitability or is at risk of having the hyperexcitability. The method can be used for determining whether the subject has the hyperexcitability or is at risk of having the hyperexcitability.

The sample may be collected from the subject prior to the detection of the RNA foci which have the repeat expansion of UUUCA. The method may be carried out in vivo. The sample may be a neuron. The RNA foci may be in a nucleus of the neuron.

The repeat expansion may be greater than 50 repeats, 100 repeats, greater than 150 repeats, greater than 200 repeats, greater than 250 repeats, greater than 300 repeats, greater than 350 repeats, or greater than 400 repeats.

The size of the expanded UUUCA may be greater than 150 base pairs, 500 base pairs, greater than 750 base pairs, greater than 1,000 base pairs, greater than 1,250 base pairs, greater than 1,500 base pairs, greater than 1,750 base pairs, or greater than 2,000 base pairs.

A kit for determining or diagnosing the hyperexcitability in the subject according to the embodiment of the present invention comprises a probe configured to detect the repeat expansion of UUUCA in the sample from the subject.

The kit can be used for the method for determining or diagnosing the hyperexcitability in the subject according to the embodiment of the present invention. The kit may be used in vivo.

The probe in the kit may comprise TGAAA. The probe may be labeled with a fluorescent dye, such as Cy-3, or radioactive materials.

Example 1: Patients

Ninety-one affected patients and nine unaffected family members from 51 families were enrolled in this study after obtaining written informed consent. All the 51 families were multiplex families consistent with autosomal dominant inheritance. Patients showed myoclonic tremor and/or epilepsy with a benign clinical course. Patients with sporadic disease or obvious progressive disease suggesting neurodegenerative diseases were excluded. The study was approved by the institutional review boards of the University of Tokyo, Niigata University, and other participating institutions. Genomic DNAs were extracted from peripheral blood leukocytes, LCLs, or autopsied tissues using standard procedures. The causes of death are shown in FIG. 31.

Example 2: SNP Genotyping

SNP genotyping using Genome-Wide Human SNP array 6.0 (Affymetrix) was conducted in accordance with the manufacturer's instructions. SNPs were called and extracted using Genotyping Console 3.0.2 (Affymetrix). Only SNPs with p values of >0.05 in the Hardy-Weinberg test in the control samples, call rates of >0.98, and minor allele frequencies of >0.05 were used for further analysis.

Example 3: Genome-Wide Linkage Study

Genome-wide linkage study was performed using the pipeline software SNP-HiTLink and Allegro version 2 with intermarker distances from 80 kb to 120 kb using an autosomal dominant model with complete penetrance. The disease allele frequency was set to $10^{-6}$. Haplotype was reconstructed using Allegro. SNPs identified by sequence analysis of the BAC clones using PacBio RSII and droplet digital PCR analysis of the genomic DNA samples from the affected individuals were also used for the haplotype reconstruction.

Example 4: Microsatellite Typing

Microsatellite markers were typed using primer pairs shown in FIG. 24, an ABI PRISM 3130xl or 3730 sequencer (Life Technologies), and GeneScan software (Life Technologies). Haplotypes were reconstructed manually to minimize recombination events.

Example 5: Whole-Genome Sequence Analysis

Whole-genome sequence analysis of patients or controls was performed using HiSeq2000 or HiSeq2500 (Illumina, 100, 101, or 150 bp paired end) in accordance with the manufacturer's instructions. Short reads were aligned to NCBI37/hg19 using BWA (v0.5.9) with default parameters. Multiply aligned or duplicated reads were removed, and variants were called using the SAMtools (v0.1.12) mpileup command. Variants were annotated using RefSeq (http://www.ncbi.nlm.nih.gov/projects/RefSeq/), dbSNP134 (http://www.ncbi.nlm.nih.gov/projects/SNP/), 1000 genomes database (http://www.1000genomes.org/), and ExAC database (http://exac.broadinstitute.org/).

Example 6: Repeat-Primed PCR Analysis

Repeat-primed PCR analysis was performed using the primers shown in FIG. 25. Fragment analysis was performed using an ABI PRISM 3130xl or 3730 sequencer (Life Technologies).

Example 7: Southern Blot Analysis

Ten micrograms of genomic DNA were digested with restriction enzymes, followed by electrophoresis in 0.8% agarose gels. Separated DNA fragments were transferred to positively charged nylon membranes (Roche Applied Science) by capillary blotting and crosslinked by exposure to ultraviolet light. Digoxygenin (DIG)-labeled probes were prepared by PCR amplification of a genomic fragment cloned into a plasmid (the primer pairs and restriction enzymes are shown in FIG. 29). Probes were designed to avoid repetitive sequences, and the ratios of DIG-dUTP: dTTP were adjusted to 0.7:1.3 and 0.35:1.65 for the size ranges of <600 bp and 600-1,500 bp, respectively, to optimize incorporation of digoxygenin in the labeling reaction by PCR. Combination of multiple probes was employed to accomplish high sensitivity of the probes in Southern blot analysis. DIG-labeled $(TGAAA)_9$ (SEQ ID NO: 17) was purchased from Eurofins Genomics. After prehybridization, hybridization was carried out at 42° C. overnight using Roche's protocols. Membranes were finally washed two times for 15 min each time in 0.5×SSC and 0.1% SDS at 65° C. for probes prepared by PCR amplification or 60° C. for the DIG-labeled $(TGAAA)_9$ oligonucleotide probe (SEQ ID NO: 17). The probes were detected using an anti-DIG-AP antibody, Fab fragments (Roche), CDP-star (Roche), and LAS3000 mini (Fujifilm).

Example 8: Construction of BAC Libraries, Isolation of Clones Containing Genomic DNA Fragments with Expanded Repeats, and Single-Molecule, Real-Time (SMRT) Sequencing Using PacBio RSII Bacterial artificial chromosome (BAC) clones containing the repeat expansions were isolated from the BAC libraries that were constructed from the lymphoblastoid cell lines (LCLs) derived from two patients (II-6 in F6906 harboring repeat configuration 1 in SAMD12 and II-1 in F6115 harboring repeat configuration 2 in SAMD12). In brief, genomic DNA fragments were ligated into the pKS145 vector after partial digestion with SacI. Unlike the standard BAC-library construction/screening procedure, candidate clones were directly isolated from the pools of the original transfectants without arraying through repeated direct PCR amplification using primer pairs for unique sequences around the repeat region (FIG. 30). Finally, one clone from II-6 in F6906 and two clones from I-2 in F6115 were confirmed to have repeat expansion mutations by repeat-primed PCR analysis. Three clones were subjected to SMRT sequencing by a Pacific Biosciences RSII sequencer using P4-C2 chemistry.

Example 9: Whole Genome Sequence Analysis Employing MinION Sequencers

Whole genome sequence analysis was performed using MinION sequencers (Oxford Nanopore Technologies) with R9.4 and R9.5 flowcells. Alignment to the reference genome hg19 was performed using NGM-LR. Assembly of the reads with the repeat expansion mutation in SAMD12 into contigs was performed using miniasm assembler. Tandem Repeat Finder (version 4.09) was used for counting the number of TTTCA and TTTTA motifs.

Example 10: Haplotype Analysis Using GemCode Technology

To elucidate whether a founder chromosome was present in F6906 and F6115, the disease haplotype was compared between F6906 and F6115. In I-2 in F6115, two BAC clones were obtained. One clone covered a 118 kb region centromeric to the repeat expansion and another clone covered an 89 kb region telomeric to the repeat. On the other hand, only a single BAC clone covering a 100 kb region centromeric to the repeat expansion and the expanded repeat sequences was obtained in II-6 in F6906. To determine disease haplotype in the telomeric region in F6906, Gemcode Technology (10× Genomics) was used. After preparing of a barcoded library using GemCode Gel Bead and Library Kit (10× Genomics), sequencing was performed with 3 lanes of HiSeq2500 (100 bp, paired end) to generate linked reads. Short-read data of the barcoded library, along with precalled variant data (a vcf file), were analyzed using Long Ranger pipelines v2.1.2 (10× Genomics). Phased haplotypes were visualized using Loupe software v2.1.1 (10× Genomics).

Example 11: Neuropathological Examination

A general autopsy of six patients with BAFME1 from four families (one homozygous patient: V-3 in F8140, and five heterozygous patients: I-2 and II-3 in F8135, II-5 in F8136, and II-5 and II-7 in F8138, as shown in FIG. 9 and FIG. 31) was performed within six hours after death. The brain and spinal cord were fixed with 20% buffered formalin, and multiple tissue blocks were embedded in paraffin. Histopathological examinations were performed on 4-μm-thick sections using several stains, including hematoxylin and eosin, and Bodian. The sections were immunostained with a mouse monoclonal antibody against calbindin protein D-28k (CaBP, Swant, 1:50). Bound antibodies were visualized by the peroxidase-polymer-based method using a Histofine Simple Stain MAX-PO kit (Nichirei) with diaminobenzidine as the chromogen.

Example 12: Fluorescence In Situ Hybridization for Detection of RNA Foci

Formalin-fixed paraffin-embedded brain tissues from six affected patients (one homozygous and five heterozygous mutation carrier) and six control subjects were examined. Cy3-labeled 60mer oligonucleotide probes ($[TGAAA]_{12}$ (SEQ ID NO: 13), $[TTTCA]_{12}$ (SEQ ID NO: 25), $[TAAAA]_{12}$ (SEQ ID NO: 26), and $[TAAAA]_{18}$ (SEQ ID NO: 27)) were purchased from Eurofins Genomics. Deparaffinization, fixation (RiboPrep, 37° C. for 30 minutes), pretreatment (37° C. for 10 min), protease treatment (Protease 2 [Roche], 37° C. for 4 min), hybridization (100 pmol of probe per slide, 37° C. for 12 h), and washing (3 times with 2× RiboWash, 37° C. for 6 min) were performed using a Ventana XT system and a RiboMap kit (Roche). Nuclei were counterstained with TOTO-3 (Invitrogen) at 1.2 µM in PBS for 30 minutes. To reduce autofluorescent signals, tissues were treated with 0.1% Sudan Black B in 70% ethanol for 5 minutes. Slides were coverslipped with a mounting medium with DAPI (VectaShield) and images were captured by confocal laser microscopy (Zeiss LSM510).

Example 13: RNA-Seq Analysis

Total RNAs were extracted from autopsied brains (occipital lobes) from five affected individuals and seven controls, the liver from three affected individuals, and LCLs from six affected individuals and two unaffected family members. After DNase treatment, rRNA was depleted using Ribo-Zero Gold (Epicentre). Libraries were constructed using TruSeq RNA Sample Preparation kit v2 (Illumina) and subjected to sequence analysis (101 bp paired end, HiSeq2000). Short reads were aligned to a reference genome NCBI37/hg19 using TopHat2 (v2.0.8b). For identification of reads filled with simple motifs, TRhist was used. For detection of differentially expressed genes, short reads were aligned to reference genome (hg19) and transcriptome sequence (GENCODE version 14, https://www.gencodegenes.org/) using TopHat v2.0.8b. Transcript quantification and detection of differentially expressed genes were performed using Cufflinks, Cuffquant, and Cuffdiff (v2.2.1) using default settings. To explore transcriptional dysregulation in BAFME brains with the TTTCA and TTTTA repeat expansions in SAMD12, RNA-seq data of 4 heterozygous BAFME1 brains and 8 control brains (occipital lobes) were subjected to the transcriptome analysis. RNA samples from one brain with a heterozygous mutation in SAMD12 was not used, because of the low RIN score (<3) assessed by Bioanalyzer (Agilent).

Example 14: SAMD12 mRNA Expression Levels Determination by Quantitative RT-PCR Analysis cDNA was synthesized using a PrimeScript first-strand cDNA synthesis kit (TaKaRa) in a total volume of 10-µl containing oligo dT primers and 0.4 µg of total RNA extracted from brains. Quantitative PCR was performed using Power SYBR Green PCR master mix (Thermo Fisher Scientific) according to the manufacturer's protocol. Primer sets used for qPCR are listed in FIG. 32. cDNA was amplified using two-step PCR as follows: 40 or 45 cycles with denaturation at 95° C. for 15 s and annealing and elongation at 65° C. for 50 s using a StepOne instrument (Thermo Fisher Scientific). Data were analyzed by the comparative CT method using StepOne Software v2.1. PCR products were also sequenced to confirm specific PCR reactions.

Example 15: Western Blotting

For western blot analysis, autopsied brain tissue samples (occipital lobes) of 6 BAFME patients with expanded repeats in SAMD12 (one homozygous patient and 5 heterozygous patients) and 5 control subjects were dissected and lysed with 10 volumes of radioimmunoprecipitation assay buffer (RIPA buffer). After adding Laemmli sample buffer containing 2-mercaptoethanol and boiling at 80° C. for 5 minutes, sixty micrograms of total protein were separated through 15% SDS-polyacrylamide gel (E-T15S, ATTO, Japan), followed by electroblotting onto a PVDF membrane (Merck KGaA). After blocking with EZblock-CAS (ATTO) for 45 min, the membrane was incubated with primary antibodies (anti-human SAMD12 rabbit antibody (ab121831, Abcam) at 1:6000 dilution and anti-human β-actin mouse antibody (C-4, Santa-Cruz) at 1:1000 dilution) overnight at 4° C. After incubation with the primary antibodies, the membranes were washed for 20 min and then incubated with HRP-linked secondary antibodies (anti-mouse IgG antibody (NA931, GE healthcare) at 1:5000 dilution or anti-rabbit IgG antibody (NA934, GE healthcare) at 1:5000 dilution at room temperature for 1 h. Membranes were washed for 150 min in Tris-buffered saline (pH 7.4) with 0.05% Tween 20 (TBS-T) followed by visualization with EzWestLumi plus (ATTO). Signals of SAMD12 bands were normalized to those of the corresponding β-actin bands as internal controls. Signals were quantified using a densitometry software (ImageJ ver1.51k).

Example 16: Search for Repeat Sequences

For whole-genome sequence and RNA-seq analyses, short-read sequences harboring repeat sequences were counted using the TRhist program. Only the reads completely filled with repeat motifs of no more than 13 bases without mismatches were counted. In the FIG. 27, four BAFME patients and seven control subjects are listed in whom whole genome sequence analysis using 150 bp paired end reads are performed. Repeat motifs in which less than nine reads were observed in all the 11 subjects were omitted.

Example 17: Statistical Analyses

Pearson's correlation coefficient of the repeat lengths and the ages at onset of epilepsy or myoclonic tremor and two-tailed p values were calculated (FIG. 4a). Changes in the repeat lengths in maternal versus in paternal transmission was compared using Wilcoxon's rank sum test (FIG. 14). The read coverage ratios of regions 1 and 2 of RNA-seq data (FIG. 16d) was compared using Wilcoxon's rank sum test. The relative expression of SAMD12 transcript 1 versus RPL13A (FIG. 16f) was compared with two-tailed Student's t test. Statistical analysis of the results of the western blot analysis was performed with two-tailed Student's t test after confirmation of equality of variances (FIG. 17). P values less than 0.05 were considered to be significant.

Example 18: Identification of Pentanucleotide Repeat Expansions

Linkage analysis revealed a single peak with a cumulative multipoint LOD score of 3.1 at 8q22.1-8q24.13 encompassing 30 Mb, confirming the previous studies (FIG. 1a and FIG. 1b and FIG. 21). The haplotype analysis (FIG. 1a and FIG. 21) revealed the core haplotype (rs2325945-rs7464659-rs6994270-rs9643124-rs4876828-rs2514991) shared among all the six families (FIG. 1c). The region, delimited by D8S0379i and rs4876833, contains only exon 4 and the portions of flanking introns of SAMD12 (sterile alpha motif domain containing 12) (FIG. 1d).

Figure 2C:
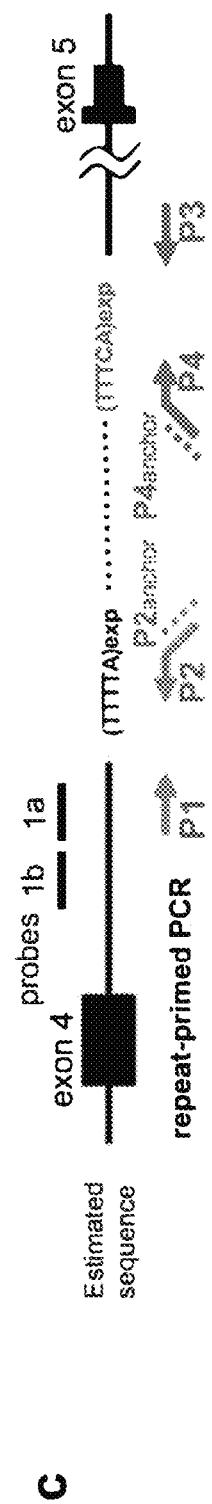

Whole-genome sequence analysis of a patient (II-6 in F6906) revealed no nonsynonymous variations in the exon 4. The present inventors noted a TTTTA pentanucleotide repeat located in intron 4 of SAMD12, whose repeat configuration in the reference genome is (TTTTA)₇(TTA)(TTTTA)₁₃ (SEQ ID NO: 11) in the transcribed strand. The repeat lengths in the family trio were apparently inconsistent with Mendelian inheritance (FIG. 2a), which immediately raised the possibility that the disease alleles of the affected father and offspring were not amplified by PCR. Intriguingly, by inspecting the paired reads from the patient with either of the reads aligned to the unique sequences of intron 4 of SAMD12, the present inventors found "extra" TTTCA repeat sequences that were not present in the reference genome (FIG. 2b). Furthermore, the present inventors observed sequences indicating the presence of TTTTA repeat expansions upstream of the extra TTTCA repeat expansions in affected individuals (II-3 in F8135 and II-6 in F6906) (FIG. 7). Based on these findings, the present inventors postulated the structure of expanded repeats (FIG. 2c) and designed the primer sets for the repeat-primed PCR (RP-PCR) analysis targeting the TTTCA and TTTTA repeats (FIG. 25). The RP-PCR analysis indeed demonstrated PCR products consistent with this postulated repeat configuration containing expanded TTTCA and TTTTA repeats in II-6 in F6906 (FIG. 2d). Southern blot analysis (FIG. 8a) further confirmed the presence of the expanded allele (FIG. 2e).

[Table 1] Table 1 discloses SEQ ID NOS 11, 28, 11, 29, 19, 30, 20, and 31, respectively, in order of appearance.

using the unique probes near the repeat (1a and 1b, FIG. 8a) or the digoxigenin-labeled (TGAAA)₉ oligonucleotide probe (SEQ ID NO: 17), however, suggested that expanded alleles were present in the affected individuals and TTTCA repeat expansions were contained inside the expanded alleles (FIG. 2f). Neither expanded TTTCA repeats nor expanded TTTTA repeats in SAMD12 were found in the remaining two families (F9283 and F8241).

Example 19: Structures of Expanded Repeats Determined by Single-Molecule, Real-Time (SMRT) Sequencing To further delineate the expanded repeat configurations, the present inventors cloned mutant alleles into a bacterial artificial chromosome (BAC) from the two patients (II-6 in F6906 and I-2 in F6115). The entire nucleotide sequences of the BAC clones were determined by SMRT sequencing employing a Pacific Biosciences RSII sequencer.

Sequence analysis of a BAC clone from patient II-6 in F6906 revealed that the TTTCA repeat expansion is located downstream of the TTTTA repeat expansion (repeat configuration 1, FIG. 3a).

SMRT sequencing of a BAC clone from another patient (I-2 in F6115) indeed revealed a TTTCA repeat expansion

TABLE 1

Summary of genetic analysis of BAFME families

| Disease | Chromosome | Gene | Number of affected members (families) | Reference sequences in hg19 | Configuration of expanded repeats |
|---|---|---|---|---|---|
| BAFME1 | 8q24.11-24.12 | SAMD12 (repeat configuration 1) | 82 (48 families) | (TTTTA)₇(TTA)(TTTTA)₁₃ | (TTTTA)$_{exp}$(TTTCA)$_{exp}$ |
|  |  | SAMD12 (repeat configuration 2) | 3 (1 family) | (TTTTA)₇(TTA)(TTTTA)₁₃ | (TTTTA)$_{exp}$(TTTCA)$_{exp}$ (TTTTA)$_{exp}$ |
| BAFME6 | 16p21.1 | TNRC6A | 5 (1 family) | (TTTTA)₁₈ | (TTTTA)₂₂(TTTCA)$_{exp}$ (TTTTA)$_{exp}$ |
| BAFME7 | 4q32.1 | RAPGEF2 | 1 (1 family) | (TTTTA)₅(TATTA)(TTTTA)₁₂ | (TTTTA)$_{exp}$(TTTCA)$_{exp}$ (TTTTA)₀ |

Abbreviation; exp, expansions

The RP-PCR analysis targeting the TTTCA and TTTTA repeats of SAMD12 was performed for the patients from the 51 families, which confirmed the presence of the both repeat expansions in 82 patients from the 48 families (FIG. 9) except the three families (F6115, F9283, and F8241).

TTTCA repeat expansions as analyzed by the RP-PCR targeting the TTTCA repeat in SAMD12 were not observed in 1,000 control subjects. In contrast, the RP-PCR analysis targeting the TTTTA repeat in SAMD12 revealed that 5.9% of control subjects (59/1,000) had expansions of TTTTA repeats. Based on the PCR-based analysis employing the primers flanking the repeats, the sizes of the TTTTA repeat expansions were approximately 0.5-1.5 kb corresponding to 100-300 TTTTA repeat units in 28 control subjects. In 31 control subjects (3.1%), however, PCR amplification failed, suggesting that substantially large TTTTA expansions are present in a small proportion of the control subjects.

Of note, three patients (I-2, II-1, and II-2) in F6115 did not show repeat expansions, as determined by the RP-PCR analysis targeting the TTTCA repeats, but only showed repeat expansions, as determined by the RP-PCR analysis targeting TTTTA repeats (FIG. 2d). Southern blot analyses between the two TTTTA repeat expansions (repeat configuration 2, FIG. 3a and FIG. 3b). It was concluded that the failure of the RP-PCR analysis targeting the TTTCA repeat (FIG. 2d) was due to the long distance between the TTTCA repeat and the primer P3.

Haplotype analyses employing SNP typing, SMRT sequencing, and 10× GemCode Technology (10× Genomics) revealed that all the variants found in disease haplotypes of F6906 (repeat configuration 1) and F6115 (repeat configuration 2) perfectly matched in the 111.7 kb region except the repeat expansion mutations, raising the possibility of a common ancestral founder for the two haplotypes (FIG. 10).

Example 20: Structures of Expanded Repeats Determined by Nanopore Sequencing

Since the sizes of expanded repeats determined by SMRT sequencing of BAC clones (0.94 kb in II-6 in F6906 and 1.0 kb in I-2 in F6115) were shorter than those determined by Southern blot analysis (5.9 kb in II-6 in F6906 and 3.9 kb in I-2 in F6115), suggesting contractions of expanded repeats during the BAC cloning, the present inventors further sequenced two genomic DNAs extracted from the peripheral blood leukocytes of II-6 in F6906 and II-1 in F6115 employing MinION sequencers (Oxford Nanopore Technologies). We collected reads that mapped to genomic sequences flanking the expanded repeats and assembled those with repeat expansions into a contig using the miniasm assembler14 (FIG. 11). Although the present inventors found substantial variation in the repeat lengths possibly reflecting error reads in nanopore sequencing and/or somatic instability of the expanded repeats, the present inventors found one pair of two reads from the plus and minus strands of an identical DNA fragment using the $1D^2$ sequencing kit (Oxford Nanopore Technologies) for each of II-6 (F6906) and II-1 (F6115). The present inventors could partly correct errors in one strand by using sequence information in the opposite strand, yielding the sequences of the mutant allele for the two samples (FIG. 12). The present inventors then partitioned the repeat expansion into two motifs and counted the number of TTTCA and TTTTA motifs using Tandem Repeat Finder. The analysis estimated the expanded repeats as $(TTTTA)_{598}(TTTCA)_{458}$ (SEQ ID NO: 32) (II-6 in F6906) and $(TTTTA)_{221}(TTTCA)_{225}(TTTTA)_{81}$ (SEQ ID NO: 33) (II-1 in F6115) (FIG. 12b and FIG. 12e).

Example 21: Expanded Repeats Exhibit Somatic Instability

Presence of expanded repeats was further confirmed by Southern blot analysis using the genomic DNAs of 77 patients from 41 families extracted from peripheral blood leukocytes, lymphoblastoid cell lines (LCLs), or autopsied tissues. The sizes of expanded TTTCA and TTTTA repeats in SAMD12 were estimated to be in the range of 2.2-18.4 kb corresponding to 440-3,680 repeat units. The lengths of expanded repeats are similar between the peripheral blood leukocytes and the LCLs from the same individuals, indicating the stability of expanded repeats in these cells (FIG. 13a). In the majority of autopsied tissues including brains, livers, and kidneys of the patients, however, Southern blot analysis revealed broad smearing patterns (FIGS. 13b-d), indicating increased somatic instabilities of expanded repeats in these tissues compared to those in peripheral blood leukocytes or LCLs.

Example 22: Repeat Lengths Inversely Correlate with the Ages at Onset of Epilepsy and Show Intergenerational Instabilities To investigate correlations between the expanded repeat lengths and the ages at onset of epilepsies, the expanded repeat lengths were determined by Southern blot analysis of genomic DNAs extracted from peripheral blood leukocytes (n=50) or LCLs (n=4). In the 54 patients with heterozygous mutations (repeat configuration 1) whose ages at onset of epilepsy were available, the lengths of the expanded repeats inversely correlated with the ages at onset of epilepsy (FIG. 4a, r=−0.47, p=3.5×10−4). Similarly, repeat lengths also inversely correlated with the age at onset of myoclonic tremor (r=−0.34, p=0.013, n=53, data not shown).

The present inventors identified four patients with homozygous expansions (one patient in F8115, two patients in F8140, and one patient in F8398). Considering the average repeat lengths of the two alleles obtained from peripheral leukocytes (n=3), their ages at onset of epilepsy tended to be earlier than those of heterozygous patients with similar sizes of expanded repeats (FIG. 4a). In some of the patients with homozygous mutations, myoclonus also appeared in the leg, which prevented them from walking in their 60s, and cognitive decline accompanied with brain atrophy was observed, showing severer clinical presentations than in patients with heterozygous mutations.

The lengths of expanded repeats tended to be unstable over successive generations, consistent with previous clinical observation of genetic anticipation (FIG. 4b and FIG. 14).

Example 23: Neuropathological Findings of Patients with Repeat Expansions in SAMD12

Neuropathological examination was conducted in six autopsied brains of patients with repeat expansions in SAMD12 (repeat configuration 1). The most striking feature was observed in the cerebellar cortex of the patient with homozygous mutations, where mild and diffuse loss of Purkinje cells and halo-like amorphous materials around the cytoplasm of several Purkinje cells were evident (FIG. 5a and FIG. 5b). These materials were clearly immunopositive for calbindin D-28k (FIG. 5c). This degenerative feature of a subset of the residual Purkinje cells was similar to that of the somatic sprouts observed in patients with spinocerebellar ataxia type 31 (SCA31, MIM117210), a disease with pentanucleotide repeat expansions, and early-onset neurodegenerative encephalopathy caused by biallelic TBCD mutations (MIM617193). On the other hand, in the cerebellum of the patients with heterozygous mutations, this feature was inconspicuous (FIG. 5d). There were no evident alterations in other brain regions in the patients with either heterozygous or homozygous mutations.

Example 24: RNA Foci are Observed in Neurons

To determine whether RNA foci are present in the brains of patients with expanded repeats in SAMD12, fluorescence in situ hybridization (FISH) was carried out in the autopsied brains from six patients and five controls using Cy3-labeled $(TGAAA)_{12}$ (SEQ ID NO: 18) or $(TTTCA)_{12}$ oligonucleotide probes (SEQ ID NO: 34). When the Cy3-$(TGAAA)_{12}$ probe (SEQ ID NO: 18) targeting the UUUCA repeat was used RNA foci were clearly observed in cortical neurons and to a lesser extent in Purkinje cells in affected brains, whereas no RNA foci were observed in the control brains using Cy3-$(TGAAA)_{12}$ (SEQ ID NO: 18) (FIG. 5e and FIG. 15).

Example 25: Global Trascriptome Analysis and Abortive Transcription in Brains

RNA-seq analysis of autopsied brains revealed 84 differentially expressed (40 down-regulated and 44 up-regulated) genes (FIG. 33) but did not detect any differentially spliced transcripts. By looking at the SAMD12 locus, however, the present inventors found excess of intronic reads located upstream of repeats, presumably due to abortive transcription at the expanded repeats (FIG. 16a, FIG. 16d, FIG. 16e). No such excesses in the number of reads were observed in LCLs or livers (FIGS. 16b-d).

Example 26: RNA-Seq Analysis Revealed Accumulation of Altered Repeat Motifs in Affected Brains When the present inventors searched for short reads filled with the particular repeat motifs, the present inventors found short reads filled with 5'-TTTCA or 5'-TGAAA repeats exclusively in the patients' brains, which correspond to the transcript of SAMD12 with TTTCA repeat expansions (Table 2). Quite intriguingly, short reads filled with 5'-CTTCA or 5'-TGAAG repeats and those filled with 5'-GTTCA or 5'-TGAAC repeats were also found in affected brains, while such sequences were neither observed in the livers (n=3) or LCLs (n=6) from the patients, nor in the brains (n=8) or LCLs (n=2) from control subjects (FIG. 26). The observations suggest presence of altered repeat motifs in the expanded repeats specifically in the affected brains.

families (F9283 and F8241, FIG. 18), which led to a hypothesis that similar TTTCA and TTTTA repeat expansions in other genes are involved in the pathogenic mutations. A search for repeat motifs using data from whole-genome sequence analysis (FIG. 27) and Southern blot analysis using the digoxigenin-labeled (TGAAA)$_9$ probe (SEQ ID NO: 17) (FIG. 6c and FIG. 6f) showed that the two families (F9283 and F8241) also had abnormal TTTCA and TTTTA repeat expansions in TNRC6A (trinucleotide repeat-

TABLE 2

Numbers of ENA-seq reads filled with TTTCA or similar motifs

| ID | Disease | Number of reads | Number of reads filled with 5'-TTTCA or 5'-TGAAA motif | Number of reads filled with 5'-CTTCA or 5'-TGAAG motif | Number of reads filled with 5'-GTTCA or 5'-TGAAC motif |
|---|---|---|---|---|---|
| F8135 II-3 | BAFME1 | 132,069,952 | 33 | 22 | 6 |
| F8136 II-5 | BAFME1 | 135,211,228 | 80 | 17 | 0 |
| F8140 V-3 | BAFME1 homozygous | 136,299,864 | 77 | 41 | 3 |
| F8135 I-2 | BAFME1 | 146,889,548 | 134 | 743 | 2 |
| F8138 II-7 | BAFME1 | 149,510,198 | 8 | 99 | 0 |
| F8138 II-5 | BAFME1 | 154,403,248 | 11 | 241 | 2 |
| Control 1 | Control | 181,071,998 | 0 | 0 | 0 |
| Control 2 | Control | 151,656,944 | 0 | 0 | 0 |
| Control 3 | Control | 163,716,120 | 0 | 0 | 0 |
| Control 4 | Control | 160,802,998 | 0 | 0 | 0 |
| Control 5 | Control | 143,280,196 | 0 | 0 | 0 |
| Control 6 | Control | 155,292,716 | 0 | 0 | 0 |
| Control 7 | Control | 162,726,784 | 0 | 0 | 0 |
| Control 8 | Control | 152,417,170 | 0 | 0 | 0 |

BAFME1: benign adult familial myoclonic epilepsy caused by TTTCA pentanucleotide repeat expansion in SMAD12.

Example 27: Analyses of SAMD12 Transcript and SAMD12 Protein Levels in Brains To examine the expression levels of SAMD12 transcripts in autopsied brains, quantitative reverse transcription-PCR analysis was performed, which did not reveal significant changes in the level of SAMD12 transcript 1 in affected brains (FIG. 16f). Note that the exact quantification of SAMD12 transcript 2 was difficult in the presence of abortive transcription products. Western blot analysis, however, showed slightly but significantly decreased levels of SAMD12 protein in affected brains (FIG. 17).

Example 28: TTTCA and TTTTA Pentanucleotide Repeat Expansions in TNRC6A and RAPGEF2 in Other Families As described above, TTTCA and TTTTA pentanucleotide repeat expansions in SAMD12 were not observed in the two containing gene 6A) and RAPGEF2 (Rap guanine nucleotide exchange factor 2), respectively.

Based on alignment, the present inventors assumed that the expanded TTTCA repeats are located between (TTTTA)$_{22}$ (SEQ ID NO: 35) and expanded TTTTA repeats in the upstream noncoding region of exon 1 of TNRC6A (FIG. 19, FIG. 20 and FIG. 6a), which was confirmed by RP-PCR (FIG. 6b) and Southern blot analyses using the probes near the repeat (6a and 6b, FIG. 8b) or the digoxigenin-labeled (TGAAA)$_9$ probe (SEQ ID NO: 17) (FIG. 6c). Cosegregation of expanded repeats was further confirmed in the five affected and one unaffected individuals in the F9283 family (FIG. 18). TTTCA repeat expansions in TNRC6A were neither found in 1,000 control subjects nor in the patients with repeat expansions in SAMD12. The RP-PCR analysis targeting the TTTTA repeat in TNRC6A revealed that 0.9% of the control subjects (9/1,000) had TTTTA repeat expansions. PCR analysis employing the primers flanking the repeats revealed that the sizes of the expanded TTTTA repeats ranged approximately 0.2-0.6 kb in 7 control subjects. In 2 control subjects (0.2%), however, PCR amplification failed, suggesting that substantially large TTTTA expansions are present in a very small proportion of the control subjects.

In the F8241 family, TTTCA repeat expansions were similarly identified in intron 14 of RAPGEF2 on chromosome 4q32.1 using paired reads anchored to the unique sequences (FIG. 22, and FIG. 6d). RP-PCR (FIG. 6e) and Southern blot analyses (FIG. 6f) using the probes near the repeat (7a-d, FIG. 8c) and the digoxigenin-labeled (TGAAA)$_9$ probe (SEQ ID NO: 17) confirmed the presence of TTTCA repeat expansions in the affected patient (III-2) that were not found in the unaffected mother. Southern blot analysis using the probes 7a-d revealed an extra band in the unaffected sibling (III-1, FIG. 6f). The existence of TTTCA repeats in III-1, however, was excluded by Southern blot analysis using the digoxigenin-labeled (TGAAA)$_9$ probe (SEQ ID NO: 17) (FIG. 6f). Sanger sequencing of the subcloned larger fragment of PCR-amplified products (III-1) revealed only a simple TTTTA repeat. Intriguingly, haplotype analysis revealed that the unaffected sibling (III-1) has the haplotype identical to that of the proband transmitted from the father who also showed tremulous movements (FIG. 23a). Taken together, the expanded TTTCA repeat located between the TTTTA repeats could have been deleted when the expanded allele was transmitted from the father (II-1) to the offspring (III-1) (FIG. 23b). These observations further support the pathogenicity of TTTCA repeat expansions in RAPGEF2. TTTCA repeat expansions in RAPGEF2 were neither found in 1,000 control subjects nor in the patients with repeat expansions in SAMD12. The RP-PCR analysis targeting the TTTTA repeat in RAPGEF2 revealed that 0.5% of the control subjects (5/1,000) had expansions. PCR analysis revealed that the sizes of the expanded TTTTA repeats ranged approximately 0.3-3 kb in 3 control subjects. In 2 control subjects (0.2%), however, PCR amplification of the expanded TTTTA repeats failed, suggesting that substantially large TTTTA expansions are present in a very small proportion of the control subjects.

```
Repeat probe
                                                                 (SEQ ID NO: 1)
Digoxigenin labeled-5'-TGAAATGAAATGAAATGAAATGAAATGAAATGAAA TGAAATGAAA Probe 1a
>chr8: 118367130 + 118367637 508 bp
                                                                 (SEQ ID NO: 2)
5'-TACAGGGGTTTTTGCCAGACaccgagaattggtggtcccccaaaaaaggccacagagaaattagttaata tgcaatattagggacagaagtcctaaagcacacagatggcatattttctgtttcttcttagaaaagccagaac atctcagtgcatctctgaaagtggctttgatttcttcttatccagtccacatgtcaatgttctaaatcaactga ctctctaaaaatcccataggacatttgaacaccgcacatattagactgtagggtctatacttatcctcaagaat aaaaccaatatcaattgttgaaaacctgtaactcatctttcttcaatgtaacattagtaatttaagatccttca aatccacagtcaagccacaaggtcaaggtgacataacaatgcaaccttatgaccatcttaaattgtccaaacaa gagatatcacatatattgtttcacctagtacatttaaatgcaaaGTGGTCAATGCATTTGAGGTTGG Probe 1b
>chr8: 118367753 + 118368385 633 bp
                                                                 (SEQ ID NO: 3)
5'-GGATCATTCCTGATAGAAAAAGTCCatattagacaaataatgtgtagacatgtctcccatatgctggctag aggaaccattaggggcgctacaaaaggcagatattttctaccatgaacaatgtaacagacaagaatcatgagt ccatgtcaagccttaaacaaaactccttcttggattaaatgacctaatggattcccagaataaaaacgaaacag gaaaagatgctaatcaggatatacatctcataattctaactgctactgataaactgacatatgattttaataat tccctcaaaaaacatgtcttttggccttta aatataaagctcattccaaggagaatttctctgatggcttaaag acttgataaaattagaaatattcctggccacaacatttctgcaagggtgcgaagattttgaaatgtgtcggggg aaatcttaaggaggtagcagttcgagaaaatgtggacttggaggaaattgagaagggacacgtgattcgcagat cataatcaaataaggttgaatgaagaagtagtaacaaaagaccctagctacagaagaataatctgttcagattc ctattaggttactcatccaaaatCCTTATCTACCATTAGCCGCT Probe 6a
>chr16: 24611127 + 24611328 202 bp
                                                                 (SEQ ID NO: 4)
5'-ATTCACATACCTTTCTGTCTCCCactgatttttcttaggagttcctctcatcctctaacctcgcttttaa aattattttctggatacctagattttgtcctttctggccagagcctgaaagaacagcttctaaggacttggt gattggaaatgtaccttctaaaaaaaattcttttttTCACTAAGACAGTGTAGAATGC
```

-continued

Probe 6b
>chr16: 24611307 + 24611798 492 bp (SEQ ID NO: 5)

5'-TCACTAAGACAGTGTAGAATGCccagttcccgctgtgtgtacgtgcgtgcacatatgtgttaaaggagatg gatacattgcttggggccatcagaactgttcctgggaggtggtttcttggctccacaccccagctcagcaagg gaatgatcaagtgataggaggcacagttacagcagtcaggagacaaggcactcggaccccaaacgtctgactct ctgtgggagaaaccagggctcaaagcaggagcaaaaaatctagtgctggatgcgctcgggcatcgagaggcatc tcgtagagctggctccgagtttgaggccacacctttgcagaatgaggcagcatgtgagcgatttagttcaatgt aattgcagtggagatggacaggagaggacagattagaatgatgtttaagggatagaaataacaagtcttgcag atatattacatatattagttgaaccatggGGAAGCCAAATGTGAATTGTGA Probe 7a
>chr4: 159342619 + 159343544 926 bp (SEQ ID NO: 6)

5'-ACTAGAGGATATTTGCTCAGTCGGttttatcaaatggccgctatgggctaagcactgctatgtgtacatac tgctgtgtatggaaacaaagcatcaatacttacattcaggtggttttactgatagtaaacagatgaggtaggtc tatacggaagagaagagtaaaacgccttggcttgaccctgaccctacttccctgtgccatctcattccccagaa ttatcatgaacagtttcttatgcagccttctgtaaattgttatgcatataaagcataaacatagagatgttata tgtcaataaataatctgtacactattttacttttagttgttataccatgtttcttttctcctctcagtggccta aacctggcaccagtggcaagactgcgaacgacctgggagaaacttcccaataaatacgaaaaactatttcaaga tctccaagacctgtttgatccttccagaaacatggcaaaatatcgtaatgttctcaatagtcaaaatctacaac ctcccataatccctctattcccagttatcaaaaaggatctcaccttccttcacgaaggtaaacataaggcagag ggtttccatctttgcttgaagaagcacagaataaatgccatgtgatttccttttcctcctctgtcaatttcagg aaatgactcaaaagtagacgggctggtcaattttgagaagctaaggatgattgcaaaagaaattcgtcacgttg gccgaatggcttcagtgaacatggaccctgccctcatgttcaggactcggtgagtatgtcatcttcagtggcac gtgtgagagtagagaaggttaaatttagagcttcccaataaatgattttttaaagtttgagtatttatatttg tagtacggcagaaatTATAGTAGGATGTGCTGAGAATCACC Probe 7b
>chr4: 159343519 + 159344422 904 bp (SEQ ID NO: 7)

5'-TATAGTAGGATGTGCTGAGAATCACCtgtgagctctaatttggaataaatgtcttattctgtataaagtgt tctttcggctgtcagtaaaaacagtttgtctttcagacattttcaatgtaatagacacaattatgtgtttctta tttctcagaacactgacttgtagagctaaaactcatagctagtagtatgcactaaaatatgtaaataccccaaa tagtcttgtctcaatatccacacaacaaatttagctagcagtgtagtaaaaagtgattaattcagtgaaagaga gaaaagtcagtcttaattctagaacaaaaaatttaaatgtatgtgtcttttaagccagaaaaatatttctagta aagttgcgtgtgtgaggtgattatgcagtttaatgtttgtgggcttctagaactgcttatccagaagtctagtc ctttctttctgagcttgtgatctttctgtctctcttttctacacccatgcttcaatctccatggctctcacttac aggaagaagaaatggcggagtttggggtaagtggtggagaccttgcatacccacacagttcttattctgctc attgcattgttttcttacctgctgtattttctgatgctttgcatttttgcattttttccttaaccctcgtgct gtagcagaatttcagatggcaaattgacttcaagtttaatctgttgggcttttgcttttgaagtcatgatcca tgagagctgtgaaatgattgatgattgttctggggaactacaggccagttttctgagctcttagaaaaatttt attttcatataattggtgtgtctcgaaatgcagaaagctcaaagtaggggggaggggaggaaggatattaGAAGG

GAAAAGTTGTGCAATTAAA

-continued

Probe 7c
>chr4: 159344976 + 159346018 1043 bp (SEQ ID NO: 8)

5'-cAgTTTACTCACTGGAATGAGGCatgtgacctttttgaacatagactattaatatcagtcttggcacatttt aaatagataaagtactcccatgctagagtgagctgcatatgtaccttttcatcttccaggtctctcagccaggg tagtacaaatgcaacagtgctagatgttgctcagacaggtggtcataaaaagcgggtacgtcgtagttcctttc tcaatgccaaaaagctttatgaagatgcccaaatggctcgaaaagtgaagcagtacctttccaatttggagcta gaaatggacgaggagagtcttcagacattatctctgcagtgtgagccagcaaccaacacatgtgagttttcct taaagtggctgcagactttggctaggatgcagatttgtttcctgtgcagtggtatgggcagtgacaaaataagg cttagtgcagagggggagctagcaatcctgagatatactagtcttttccttgaatgctaatatttaatactggg tagcactgtgcacggccaggccgtcatgtcaactgggttagtatgtggaagatgacactgtccacatctaaggc aacccattactttagtttcacctggacacaaccagtacacatgcaacagacgcatatatagatatggctcccat ttacatgtcttacgttctcacaaagctaccccaaagtatgggcaacctgaggggagtcagggcataaaattgg gtgtgctggctgccttttaaccactagcccagacaacaccgaacaacaaattcagctaccagttagttagagca atgattctgctccacagtgaaccacaatagcctttaaaaatctggttaatctataaatggggcagtttttttt ttttctaaatctgcatcttgacttaaaagacaaaggcattttccattcagtacacacctgtgtcttttatgggc aggtttgaagatgtcttctgtaggatttaatttagataggtgatttgagaagatttgGATTATTAGATTTACCC

AGGATGCTGT

Probe 7d
>chr4: 159346221 + 159347484 1264 bp (SEQ ID NO: 9)

5'-TATTGTCCTAAATTGCTTTGCCatttatctaccacaaaatatatactcagtatgatactgaagcattattg gctactgtttgcttgcatagataattctacctcctaggaatatggtagtaaatagattgcagttgacagcattt attaaataaaaacttagcacatacatgtcaaacaatttgggacaccgttttagaaaaatagtgcctgatgactt ttctgttgtagcttttatcacgtatttgtttctttcatatacatggatataacatattgaactacccacatttt tctatatttttaatggggtgtttaatagtacaatcatcttttgagattgctgacttcataaagtagataccttt gtcctgccacatatctaatattttctgtaactagggtcccccatccattttctgtgcttcataaaggcaacagg aagaaaggtgtgcattaatttagtattctaactgcagaaaatgctcacacagttctagaattatcttctacata cctactagcatctaaaattctttgttctattttcaaacccaaacaattatcagtgcctaagaatcctggtgaca aaaagcctgtcaaatccgagacctctccagtagctccaagggcagggtcacaacagaaagctcagtccctgcca cagcccagcagcagccaccaccagcacataaaatcaaccagggactacaggttcccgccgtgtcccttatcc ttcacggaagaaagtgcccgtaaaggatctcccaccttttggtaagtgattacattcattctttttttggtgc cattcactgtcatggtttgcaaattaggaaaaaaatatttgtcttggataactttgtctaatatatttgagttt ctctgtaattattagctcctaataaaacatgaacactcagcaagttaaacctgactttgccaatggaaggggt tgttttataagtaatatctcgtttagtcatgctaatttgctacgacagggtgttaatagagaagttatgtgtc tattaatttaattttgctaagcgcagaagatgctttgttcatttacattatttaaactggttttgctttacaa ccaacaaactgctgggatttaagcagaatattttaagttaaatgaattgtctgaaggtaaattcttatttgtt gactcactgattctataacttagagggaaaaataaaacaactaactcctgaatatgaaGGAGCTAAATTACACT

TCATCTTTTCC

Nucleotide positions are based on hg38.

SEQUENCE LISTING

Citation List

Non Patent Literature

[NPL 1]
Uyama, E., Fu, Y. H., & Ptácek, L. J. Familial adult myoclonic epilepsy (FAME). In: Delgado-Escueta, A. V., Guerrini, R., Medina, M. T., Genton, P., Bureau, M., Dravet, C., eds. Advances in neurology, Vol. 95: Myoclonic Epilepsies. Philadelphia, Lippincott Willams & Wilkins. 281-288 (1995).

The invention claimed is:

1. A method for detecting a repeat expansion of nucleic acid, comprising:
   providing a nucleic acid sample comprising an intron of a SAMD12 gene from a human subject; and
   detecting at least one repeat expansion in the intron of the SAMD12 gene, wherein the repeat expansion comprises:
   greater than 2.2 kb of TTTCA repeats or TGAAA repeats;
   greater than 2.2 kb of TTTTA repeats or TAAAA repeats; or
   greater than 2.2 kb of TTTCA repeats or TGAAA repeats and TTTTA repeats or TAAAA repeats.

2. The method of claim 1, wherein the repeat expansion comprises TTTCA repeats with flanking TTTTA repeats, or TGAAA repeats with flanking TAAAA repeats.

3. The method of claim 1, wherein the intron comprises intron 4 of the SAMD12 gene.

4. The method of claim 2, wherein the intron comprises intron 4 of the SAMD12 gene.

5. The method of claim 1, wherein the repeat expansion comprises less than 18.4 kb of TTTCA repeats or TGAAA repeats.

6. The method of claim 1, wherein the repeat expansion comprises less than 18.4 kb of TTTTA repeats or TAAAA repeats.

* * * * *